(12) United States Patent
Apodaca et al.

(10) Patent No.: US 8,530,476 B2
(45) Date of Patent: *Sep. 10, 2013

(54) PIPERAZINYL AND PIPERIDINYL UREAS AS MODULATORS OF FATTY ACID AMIDE HYDROLASE

(75) Inventors: Richard Apodaca, San Diego, CA (US); J. Guy Breitenbucher, Escondido, CA (US); Kanaka Pattabiraman, Los Altos, CA (US); Mark Seierstad, San Diego, CA (US); Wei Xiao, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 443 days.

This patent is subject to a terminal disclaimer.

(21) Appl. No.: 12/557,650

(22) Filed: Sep. 11, 2009

(65) Prior Publication Data

US 2010/0004261 A1    Jan. 7, 2010

Related U.S. Application Data

(63) Continuation of application No. 11/321,710, filed on Dec. 29, 2005, now Pat. No. 7,598,249.

(60) Provisional application No. 60/640,869, filed on Dec. 30, 2004.

(51) Int. Cl.
    *A61K 31/497* (2006.01)
    *C07D 403/00* (2006.01)
    *C07D 405/06* (2006.01)
    *C07D 401/06* (2006.01)

(52) U.S. Cl.
    USPC ............ 514/252.14; 514/253.01; 514/253.13; 544/295; 544/364; 544/367

(58) Field of Classification Search
    None
    See application file for complete search history.

(56) References Cited

U.S. PATENT DOCUMENTS

| | | | |
|---|---|---|---|
| 3,813,395 A | 5/1974 | Nakanishi et al. | |
| 6,096,784 A | 8/2000 | Lerner et al. | |
| 6,100,279 A | 8/2000 | Vaccaro et al. | |
| 6,462,054 B1 | 10/2002 | Boger | |
| 7,598,249 B2 * | 10/2009 | Apodaca et al. | 514/252.12 |
| 2003/0187040 A1 | 10/2003 | Pevarello et al. | |
| 2004/0220191 A1 | 11/2004 | Schwink et al. | |
| 2006/0014830 A1 | 1/2006 | Abouabdellah et al. | |
| 2006/0089344 A1 | 4/2006 | Abouabdellah et al. | |
| 2006/0178399 A1 | 8/2006 | Nishizawa et al. | |

FOREIGN PATENT DOCUMENTS

| | | |
|---|---|---|
| CN | 1145620 A | 3/1997 |
| DE | 2123784 | 5/1970 |
| EP | 0 285 219 A2 | 3/1988 |
| EP | 0 285 219 A3 | 3/1988 |
| EP | 0 285 219 B1 | 3/1988 |
| JP | 48010160 | 3/1973 |
| JP | 15456 80 A | 2/1980 |
| JP | 51176495 A | 7/1996 |
| JP | 2000511949 A | 11/1997 |
| JP | 2000513009 A | 8/1998 |
| JP | 11139969 | 5/1999 |
| WO | WO 93/00342 A1 | 1/1993 |
| WO | WO 96/09817 A1 | 4/1996 |
| WO | WO 96/21648 A1 | 7/1996 |
| WO | 97 23458 A1 | 7/1997 |
| WO | WO 97/23458 A1 | 7/1997 |
| WO | WO 97/42230 A1 | 11/1997 |
| WO | WO 97/49667 A1 | 12/1997 |
| WO | WO 98/37077 A1 | 8/1998 |
| WO | WO 99/24421 A1 | 5/1999 |
| WO | WO 99/26584 A1 | 6/1999 |
| WO | WO 99/42107 A1 | 8/1999 |
| WO | 02 26203 | 5/2000 |
| WO | 01 36386 A1 | 5/2001 |
| WO | WO 01/36386 A1 | 5/2001 |
| WO | WO 02/08221 A2 | 1/2002 |
| WO | WO 0240466 A2 | 5/2002 |
| WO | WO 0250061 * | 6/2002 |
| WO | WO 02/087569 A1 | 11/2002 |
| WO | 03 037271 A2 | 5/2003 |
| WO | WO 03/047569 A1 | 6/2003 |
| WO | WO 03/065989 A2 | 8/2003 |
| WO | WO 2004/033652 A2 | 4/2004 |
| WO | WO 2004/067498 A2 | 8/2004 |
| WO | WO 2004/072025 A2 | 8/2004 |
| WO | 2004 080966 A1 | 9/2004 |
| WO | WO 2004/080966 A1 | 9/2004 |
| WO | WO 2004/099176 A1 | 11/2004 |
| WO | WO 2004110451 A1 | 12/2004 |

OTHER PUBLICATIONS

International Preliminary Report on Patentability for Corresponding International Application No. PCT/US05/47329, Mailed Nov. 16, 2009, 6 pgs.

Bagshawe et al. "Antibody-Directed Enzyme Prodrug Therapy: A Review" Drug ev res 1995 vol. 34 pp. 220-230.

Baker et al., "Cannabinoids controls spasticity and tremor in a multiple sclerosis model," *Nature* 2000, 404, 84-87.

Baker et al., "Endocannabinoids control spasticity in a multiple sclerosis model," *FASEB J.* 2001, 15(2), 300-302.

Baker et al., "The Therapeutic Potential of Cannabis in Multiple Sclerosis," Expert Opin Investig Drugs. 2003, 12, 561-567.

Barann et al., "Direct Inhibition by Cannabinoids of Human 5-HT3A Receptors: Probable Involvement of an Allosteric Modulatory Site," Br J Pharmacol. 2002, 137, 589-596.

(Continued)

*Primary Examiner* — Noble Jarrell
(74) *Attorney, Agent, or Firm* — Michael J. Atkins

(57) ABSTRACT

Certain piperazinyl and piperidinyl urea compounds are useful as FAAH inhibitors. Such compounds may be used in pharmaceutical compositions and methods for the treatment of disease states, disorders, and conditions mediated by fatty acid amide hydrolase (FAAH) activity. Thus, the compounds may be administered to treat, e.g., anxiety, pain, inflammation, sleep disorders, eating disorders, or movement disorders (such as multiple sclerosis).

24 Claims, No Drawings

(56) References Cited

OTHER PUBLICATIONS

Berge et al Pharmaceutical Salts J Pharm Sci 1977 vol. 66 pp. 1-19.
Bertolini et al "A New Rational Hypothesis for the Pharmacophore of the Active Metabolite of Leflunomid, a Potent Immunosuppressive Drug" J Med Chem 1997 vol. 40 pp. 2011-2016.
Bisogno et al., "Fatty Acid Amide Hydrolase, an Enzyme with Many Bioactive Substrates. Possible Therapeutic Implications," Curr Pharm Des. 2002, 8, 533-47.
Bodor et al "Novel Approaches to the Design of Safer Drugs: Soft Drugs and Site Specific Chemical Delivery Systems" Advances in Drug Res 1984 vol. 13 pp. 255-331.
Boger et al., "Trifluoromethyl ketone inhibitors of fatty acid amide hydrolase: A probe of structural and conformational features contributing to inhibition," *Bioorg. Med. Chem. Lett.* 1999, 9, 265-270.
Boger et al "Exceptionally Potent Inhibitors of Fatty Acid Amide Hydrolase: The Enzyme Responsible for Degradation of Endogenous Oleamide and Anandamide" Proc Nat Acad Sci USA 2000 vol. 97(10) pp. 5044-5049.
Boger et al., "Oleamide: an endogenous sleep-inducing lipid and prototypical member of a new class of biological signaling molecules," Curr Pharm Des. 1998, 4, 303-314.
Boger et al "α-Keto Heterocycle Inhibitors of Fatty Acid Amide Hydrolase: Carbonyl Group Modification and α Substitution" Bioorg Med Chem Lett 2001 vol. 11 pp. 1517-1520.
Bracey et al., "Structural adaptations in a membrane enzyme that terminates Endocannabinoid Signaling," Science 2002, 298, 1793-96.
Bundgaard et al Design of Prodrugs Elsevier Press 1985.
Cravatt et al., "Molecular characterization of an enzyme that degrades neuromodulatory fatty-acid amides," *Nature* 1996, 384(6604), 83-86.
Cravatt et al., "Supersensitivity to anandamide and enhanced endogenous cannabinoid signaling in mice lacking fatty acid amide hydrolase," *Proc. Natl. Acad. Sci. USA* 2001, 98(16), 9371-9376.
Cravatt et al Science 1995 vol. 268(5216) pp. 1506-1509.
Croxford, "Therapeutic potential of cannabinoids in CNS Disease," CNS Drugs 2003, 17, 179-202.
Devane et al., "Isolation and structure of a brain constituent that binds to the cannabinoid receptor," *Science* 1992, 258(5090), 1946-1949.
Dinh et al., "Brain monoglyceride lipase participating in endocannabinoid inactivation," PNAS, 2002, 99, 10819-24.
Fleisher et al "Improved Oral Drug Delivery: Solubility Limitations Overcome by the Use of Prodrugs" Adv Drug Del Rev 1996 vol. 19 pp. 115-130.
Fowler et al., "Fatty acid amide hydrolase: biochemistry, pharmacology, and therapeutic possibilities for an enzyme hydrolyzing anandamide, 2-arachidonoylglycerol, palmitoylethanolamide, and oleamide," Biochem Pharmacol. 2001, 62, 517-26.
Giang et al., "Molecular characterization of human and mouse fatty acid amide hydrolases," PNAS 1997, 94, 2238-42.
Goya et al., "Recent advances in cannabinoid receptor agonists and antagonists," *Exp. Opin. Ther. Patents* 2000, 10(10), 1529-1538.
Hertzog et al "Recent Advances in the Cannabinoids" Expert Opin in Therapeutics Patents 2004 vol. 14(10) pp. 1435-1452.
Howlett et al., "International Union of Pharmacology. XXVII. Classification of Cannabinoid Receptors," Pharmacol Rev. 2002, 54, 161-202.
Kathuria et al., "Modulation of anxiety through blockade of anandamide hydrolysis," Nat. Med. 2003, 9(1), 76-81.
Kirkham et al., "Endocannabinoid levels in rat limbic forebrain and hypothalamus in relation to fasting, feeding and satiation: stimulation of feeding by 2-arachidonyl glycerol," *Br. J. Pharmacol.* 2002, 136, 550-557.
Jantzen et al "Prodrugs" Modern Pharmaceutics 1996 pp. 596.

Lambert et al., "The palmitoylethanolamide family: A new class of anti-inflammatory agents?" *Curr. Med. Chem.* 2002, 9(6), 663-674.
Lambert et al., "The palmitoylethanolamide and oleamide enigmas : are these two fatty acid amides cannabimimetic?," Curr Med Chem. 1999, 6, 757-73.
Larsen et al Design and Application of Prodrugs Drugs Design and Development Krogsgaard-Larsen et al. Eds. Harwood Academic Publishers 1991.
Mendelson et al., "The hypnotic actions of the fatty acid amide, oleamide," *Neuropsychopharmacology* 2001, 25(S5), S36-S39.
Metabolite Encyclopedia.Com—http://www.encyclopedia.com/doc/1E1-metabolit.html, accessed Jan. 25, 2008.
Olah et al., "Anandamide activates vanilloid receptor 1 (VR1) at acidic pH in dorsal root ganglia neurons and cells ectopically expressing VR1," J Biol Chem. 2001, 276, 31163-70.
Piomelli, "The molecular logic of endocannabinoid signalling," *Nat. Rev. Neurosci.* 2003, 4(11), 873-884.
Quistad et al., "Selective inhibitors of fatty acid amide hydrolase relative to neuropathy target esterase and acetylcholinesterase: toxicological implications," Toxicol Appl Pharmacol. 2002, 179, 57-63.
Robinson et al "Discovery of the Hemifumarate and (α-L-Alanyloxy)Methyl Ether as Prodrugs of an Antirheumatic Oxindole: Prodrugs for the Enolic OH Group" J Med Chem 1996 vol. 39 pp. 10-18.
Robson, "Therapeutic aspects of cannabis and cannabinoids," *Br. J. Psychiatry* 2001, 178, 107-115.
Rodriguez de Fonseca et al., "An anorexic lipid mediator regulated by feeding," Nature 2001, 414, 209-12.
Savinainen et al., "Despite substantial degradation, 2-arachidonoylglycerol is a potent full efficacy agonist mediating CB(1) receptor-dependent G-protein activation in rat cerebellar membranes," Br J Pharmacol. 2001, 134, 664-72.
Shan et al "Pharmaceutical Strategies Based on Intramolecular Cyclization Reactions" J Pharm Sci 1997 vol. 86(7) pp. 765-767.
Stahl et al Handbook of Pharmaceutical Salts Properties Selection and Use Stahl PH Wermuth CG Eds. Wiley-VCH- and VHCA Zurich 2002.
Stamer et al., "Cannabinoid CB(1) receptor expression, activation and detection of endogenous ligand in trabecular meshwork and ciliary process tissues," Eur J Pharmacol. 2001, 431, 277-86.
Sugiura et al., "Evidence that 2-arachidonoylglycerol but not N-palmitoylethanolamine or anandamide is the physiological ligand for the cannabinoid CB2 receptor. Comparison of the agonistic activities of various cannabinoid receptor ligands in HL-60 cells," J Biol Chem. 2000, 275, 605-12.
Svendsen et al., "Does the cannabinoid dronabinol reduce central pain in multiple sclerosis? Randomised double blind placebo controlled crossover trial," *Br. Med. J.* 2004, 329(7460), 253-260.
Tarzia et al., "Design, synthesis, and structure-activity relationships of alkylcarbamic acid aryl esters, a new class of fatty acid amide hydrolase inhibitors," *J. Med. Chem.* 2003, 46, 2352-2360.
Ueda et al., "Purification and characterization of an acid amidase selective for N-palmitoylethanolamine, a putative endogenous anti-inflammatory substance," *J. Biol. Chem.* 2001, 276(38), 35552-35557.
Vaccaro et al., "Novel Histamine $H_3$ Receptor Antagonists Based on the 4-[(1 H-imidazol-4-yl)methyl]piperidine scaffold," *Bioorg. Med. Chem. Lett.* 2006, 16(2), 395-399.
Van der Stelt et al., "Exogenous anandamide protects rat brain against acute neuronal injury in vivo," J Neurosci. 2001, 21, 8765-71.
Inflammation http://www,nlm,nih.gov/cgi/mesh/2008/MB_cgi, Accessed Feb. 20, 2008.
Sleep Disorders http://www.nlm.nih.gov/cgi/mesh/2008/MB_cqi?mode=&index=12386&field=all&HM=&II=&PA=&form=&input Accessed Dec. 8, 2008.

* cited by examiner

PIPERAZINYL AND PIPERIDINYL UREAS AS MODULATORS OF FATTY ACID AMIDE HYDROLASE

CROSS-REFERENCE TO RELATED APPLICATION

This application is a continuation of U.S. Ser. No. 11/321,710 filed on Dec. 29, 2005, now U.S. Pat. No. 7,598,249, granted on Oct. 6, 2009, which claims the benefit under 35 USC §119(e) of the following provisional application: U.S. Ser. No. 60/640,869 filed on Dec. 30, 2004. The complete disclosures of the aforementioned related U.S. patent applications are hereby incorporated herein by reference for all purposes.

FIELD OF THE INVENTION

The present invention relates to certain piperazinyl and piperidinyl urea compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

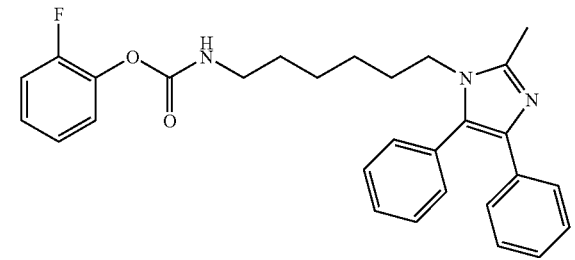

BMS-1

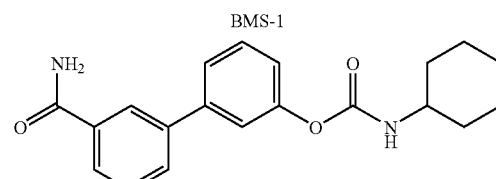

URB-597

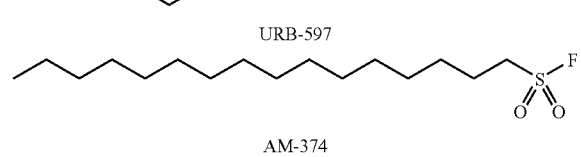

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

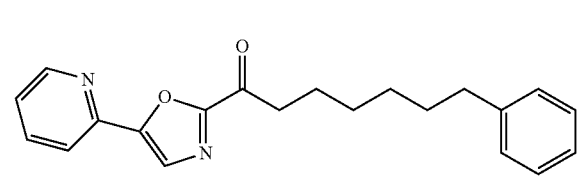

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reported to have been initiated in Germany in May 2002.

A number of individuals with multiple sclerosis have claimed a benefit from cannabis for both disease-related pain and spasticity, with support from small controlled trials (Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD).

Reports of small-scale controlled trials have been conducted to investigate other potential commercial uses of cannabinoids have been made. Trials in volunteers have been reported to have confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation, immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36).

Certain piperazinyl or piperidinyl derivatives have been disclosed in the literature for different uses. For example, JP 11139969 describes certain phenol derivatives as antioxidants and ACAT inhibitors; WO 96/21648 discloses various piperazine derivatives as antitumor agents; JP 48010160 describes certain piperazine derivatives as anti-inflammatory agents; WO 04/072025 discloses certain substituted N-arylheterocycles as obesity, diabetes, and drug abuse agents; DE 2123784 and U.S. Pat. No. 3,813,395 disclose various piperazinylthieno-benzothiazepines as psychotropics and anesthetics; and WO 98/37077 and WO 99/42107 describe certain piperazine-based compounds as calcitonin mimetics for treatment of bone deficits. Additionally, WO 97/42230 describes a solid-phase synthesis of certain piperazine ureas. WO 97/23458 discloses certain piperidine derivatives as intermediates toward NMDA receptor ligands. In addition, various small-molecule FAAH modulators have been reported, e.g., in WO 04/033652, U.S. Pat. No. 6,462,054, U.S. Pat. No. 6,096,784, WO 99/26584, WO 97/49667, and WO 96/09817. However, there is still a need for other potent FAAH modulators with desirable pharmaceutical properties.

SUMMARY OF THE INVENTION

Certain piperazinyl or piperidinyl derivatives have now been found to have FAAH-modulating activity.

In particular, in one general aspect the invention relates to compounds of the following Formula (I):

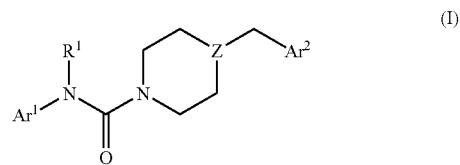

wherein:
  Z is —N— or >CH;
  $R^1$ is —H or —$C_{1-4}$alkyl;
  $Ar^1$ is 2-thiazolyl, 2-pyridyl, 3-pyridyl, 4-pyridyl, 2-pyrimidinyl, 4-pyrimidinyl, 5-pyrimidinyl, or phenyl, each unsubstituted or substituted at a carbon ring member with one or two $R^a$ moieties;
    where each $R^a$ moiety is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are each independently —H or —$C_{1-4}$alkyl; and
  $Ar^2$ is:
    (a) unsubstituted 1-naphthyl; or phenanthrenyl, pyrenyl, fluorenyl, 2-naphthyl, or N—$R^d$-9H-carbazolyl moieties, wherein $R^d$ is selected from the group consisting of —H, —$C_{1-4}$alkyl, and phenyl, each said moiety unsubstituted or substituted with one, two, or three $R^e$ substituents,
      wherein each $R^e$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined (each independently —H or —$C_{1-4}$alkyl);
    (b) phenyl fused at two adjacent ring carbon atoms to a group selected from the group consisting of —$(CH_2)_{3-5}$— having 0 or 1 double bonds, —$(CH_2)_{2-3}$O—, —$OCH_2CH_2O$—, and —$OCF_2O$— to form a fused ring structure; or phenyl substituted on adjacent ring carbon atoms with —$OCH_2O$— (to form 4-benzo[1,3]dioxolyl); each phenyl moiety further unsubstituted or substituted with one, two, or three $R^e$ substituents as previously defined;
    (c) $Ar^6$, where $Ar^6$ is a 6-membered monocyclic heteroaryl having carbon as a point of attachment, with one or two nitrogen heteroatoms (—N=), unsubstituted or substituted with one, two, or three $R^e$ substituents as previously defined;

(d) $Ar^5$, where $Ar^5$ is a 5-membered monocyclic heteroaryl having carbon as a point of attachment, with one heteroatom selected from the group consisting of O, S, >NH, and >NR$^f$, wherein R$^f$ is $C_{1-8}$alkyl or $C_{0-3}$phenalkyl, having zero, one, two, or three additional nitrogen heteroatoms (—N=), unsubstituted or substituted with one, two, or three R$^e$ substituents as previously defined;

(e) a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two, or three R$^e$ substituents as previously defined;

(f) phenyl substituted at the 3- or 4-position with R$^g$, and optionally further substituted with one, two, or three substituents R$^h$, wherein each R$^g$ is independently selected from the group consisting of —$C_{2-8}$alkyl, —$C_{2-8}$alkenyl, —$OC_{3-8}$cycloalkyl, —$OC_{3-8}$heterocycloalkyl, and —O—$C_{2-10}$alkyl optionally substituted with —NR$^i$R$^j$, wherein R$^i$ and R$^j$ are each independently —H or —$C_{1-8}$alkyl, or R$^i$ and R$^j$ are taken together with the nitrogen ring atom of attachment to form a 5-, 6-, or 7-membered heterocycloalkyl ring optionally having one additional carbon ring atom replaced with O, S, >NH, or >NC$_{1-4}$alkyl; and each R$^h$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —N(R$^b$)R$^c$, —$SO_2NR^bR^c$, —NR$^b$SO$_2$R$^c$, —C(=O)NR$^b$R$^c$, —$NO_2$, and —CN, wherein R$^b$ and R$^c$ are as previously defined;

(g) phenyl substituted at the 3- or 4-position with -L-Ar$^3$, wherein:

L is a linker selected from the group consisting of —(CH$_2$)$_{1-3}$—, —CH=CH—, —O—, —OCH$_2$—, —CH$_2$O—, —NH—, >NC$_{1-4}$alkyl, >S(=O)$_{0-2}$, —OSO$_2$—, —C≡C—, —C(=O)—, and a covalent bond; and Ar$^3$ is a moiety selected from the group consisting of:

(1) phenyl, naphthyl, and phenanthrenyl, (2) Ar$^{6'}$, where Ar$^{6'}$ is a 6-membered monocyclic heteroaryl having carbon as a point of attachment, having one or two nitrogen heteroatoms (—N=), (3) Ar$^{5'}$, where Ar$^{5'}$ is a 5-membered monocyclic heteroaryl having carbon as a point of attachment, with one heteroatom selected from the group consisting of O, S, >NH, and >NR$^f$, wherein R$^f$ is —$C_{1-8}$alkyl or —$C_{0-3}$phenalkyl, and having zero, one, two, or three additional nitrogen heteroatoms (—N=), and (4) a 9- or 10-membered fused bicyclic heteroaryl, having one heteroatom selected from the group consisting of N, O, and S, with a carbon as point of ring attachment, and optionally having up to four additional carbon ring atoms replaced with nitrogen, said fused bicyclic heteroaryl having not more than five heteroatoms;

where each of the moieties (1) through (4) is optionally di-substituted on adjacent carbons with —$OC_{1-4}$alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)-, or —(CH$_2$)$_{1-2}$N(C$_{1-4}$alkyl) (CH$_2$)— to form a fused ring structure, and is further optionally substituted with one, two, or three substituents R$^k$, wherein each R$^k$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —N(R$^b$)R$^c$, —$SO_2NR^bR^c$, —NR$^b$SO$_2$R$^c$, —C(=O)NR$^b$R$^c$, —$NO_2$, and —CN, wherein R$^b$ and R$^c$ are as previously defined;

(h) 2-hydroxyphenyl or 2-methoxyphenyl, unsubstituted or substituted with one, two, or three substituents R$^l$, wherein each R$^l$ substituent is independently selected from the group consisting of —$CH_3$, 6-$C_{2-4}$alkyl, 6-$C_{2-4}$alkenyl, —OH, —$OCH_3$, 6-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —N(R$^b$)R$^c$, —$SO_2NR^bR^c$, —NR$^b$SO$_2$R$^c$, —C(=O)NR$^b$R$^c$, —$NO_2$, and —CN, wherein R$^b$ and R$^c$ are as previously defined;

(i) 4-halophenyl, unsubstituted or substituted with one, two, or three substituents R$^m$, wherein each R$^m$ substituent is independently selected from the group consisting of —$CH_3$, 2-$C_{2-4}$alkyl, 2-$C_{2-4}$alkenyl, 3-hydroxy, 4-hydroxy, —$OCH_3$, 2-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —N(R$^b$)R$^c$, —$SO_2NR^bR^c$, —NR$^b$SO$_2$R$^c$, —C(=O)NR$^b$R$^c$, —$NO_2$, and —CN, wherein R$^b$ and R$^c$ are as previously defined; or (j) 2-bromophenyl, 3-methylphenyl, 3-methoxyphenyl, 4-methoxyphenyl, or 3,4-dimethoxyphenyl;

where when Ar$^2$ is 4-fluorophenyl, 3,4-difluorophenyl, 4-chlorophenyl, or 3-methoxyphenyl, Ar$^1$ is not unsubstituted phenyl or phenyl substituted with 4-Cl, —$NO_2$, —$CF_3$, or 4-$CO_2$Et; and where when Ar$^2$ is 3,4-dichlorophenyl, Ar$^1$ is not phenyl substituted with 4-Cl, —$NO_2$, —$CF_3$, or 4-$CO_2$Et;

or a pharmaceutically acceptable salt, pharmaceutically acceptable prodrug, or pharmaceutically active metabolite of said compound.

In preferred embodiments, the compound of Formula (I) is a compound specifically described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of a compound of Formula (I) wherein:

Z is as defined above;

R$^1$ is as defined above;

Ar$^1$ is as previously defined; and

Ar$^2$ is:

(a) phenanthrenyl, pyrenyl, fluorenyl, naphthyl, or N—R$^d$-9H-carbazolyl moieties, wherein R$^d$ is selected from the group consisting of —H, —$C_{1-4}$alkyl, and phenyl, each said moiety unsubstituted or substituted with one, two, or three R$^e$ substituents, wherein each R$^e$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined (each independently —H or —$C_{1-4}$alkyl);

(b) phenyl fused at two adjacent ring carbon atoms to a group selected from the group consisting of —$(CH_2)_{3-5}$— having 0 or 1 double bonds, —$(CH_2)_{2-3}O$—, —$OCH_2CH_2O$—, —$OCF_2O$— and —$OCH_2O$— to form a fused ring structure, unsubstituted or substituted with one, two, or three $R^e$ substituents as previously defined;

(c) $Ar^6$, where $Ar^6$ is a 6-membered monocyclic heteroaryl having carbon as a point of attachment, with one or two nitrogen heteroatoms (—N=), unsubstituted or substituted with one, two, or three $R^e$ substituents as previously defined;

(d) $Ar^5$, where $Ar^5$ is a 5-membered monocyclic heteroaryl having carbon as a point of attachment, with one heteroatom selected from the group consisting of O, S, >NH, and >$NR^f$, wherein $R^f$ is $C_{1-8}$alkyl or $C_{0-3}$phenalkyl, having zero, one, two, or three additional nitrogen heteroatoms (—N=), unsubstituted or substituted with one, two-, or three $R^e$ substituents as previously defined;

(e) a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two, or three $R^e$ substituents as previously defined;

(f) phenyl substituted at the 3- or 4-position with $R^g$, and optionally further substituted with one, two, or three substituents $R^h$, wherein each $R^g$ is independently selected from the group consisting of —$C_{2-8}$alkyl, —$C_{2-8}$alkenyl, —$OC_{3-8}$cycloalkyl, —$OC_{3-8}$heterocycloalkyl, and —O—$C_{2-10}$alkyl optionally substituted with —$NR^iR^j$, wherein $R^i$ and $R^j$ are each independently —H or —$C_{1-8}$alkyl, or $R^i$ and $R^j$ are taken together with the nitrogen ring atom of attachment to form a 5-, 6-, or 7-membered heterocycloalkyl ring optionally having one additional carbon ring atom replaced with O, S, >NH, or >$NC_{1-4}$alkyl; and each $R^h$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(g) phenyl substituted at the 3- or 4-position with -L-$Ar^3$, wherein:

L is a linker selected from the group consisting of —$(CH_2)_{1-3}$—, —CH=CH—, —O—, —$OCH_2$—, —$CH_2O$—, —NH—, >$NC_{1-4}$alkyl, >$S(=O)_{0-2}$, —$OSO_2$—, —C≡C—, —C(=O)—, and a covalent bond; and $Ar^3$ is a moiety selected from the group consisting of:

(1) phenyl, naphthyl, and phenanthrenyl, (2) $Ar^{6'}$, where $Ar^{6'}$ is a 6-membered monocyclic heteroaryl having carbon as a point of attachment, having one or two nitrogen heteroatoms (—N=), (3) $Ar^{5'}$, where $Ar^{5'}$ is a 5-membered monocyclic heteroaryl having carbon as a point of attachment, with one heteroatom selected from the group consisting of O, S, >NH, and >$NR^f$, wherein $R^f$ is —$C_{1-8}$alkyl or —$C_{0-3}$phenalkyl, and having zero, one, two, or three additional nitrogen heteroatoms (—N=), and (4) a 9- or 10-membered fused bicyclic heteroaryl, having one heteroatom selected from the group consisting of N, O, and S, with a carbon as point of ring attachment, and optionally having up to four additional carbon ring atoms replaced with nitrogen, said fused bicyclic heteroaryl having not more than five heteroatoms;

where each of the moieties (1) through (4) is optionally di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}$alkyl)-, or —$(CH_2)_{1-2}N(C_{1-4}$alkyl)$(CH_2)$— to form a fused ring structure, and is optionally further substituted with one, two, or three substituents $R^k$, wherein each $R^k$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(h) 2-hydroxyphenyl or 2-methoxyphenyl, unsubstituted or substituted with one, two, or three substituents $R^l$, wherein each $R^l$ substituent is independently selected from the group consisting of —$CH_3$, 6-$C_{2-4}$alkyl, 6-$C_{2-4}$alkenyl, —OH, —$OCH_3$, 6-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(i) 4-halophenyl, unsubstituted or substituted with one, two, or three substituents $R^m$, wherein each $R^m$ substituent is independently selected from the group consisting of —$CH_3$, 2-$C_{2-4}$alkyl, 2-$C_{2-4}$alkenyl, 3-hydroxy, 4-hydroxy, —$OCH_3$, 2-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined; or (j) 2-bromophenyl, 3-methylphenyl, 3-methoxyphenyl, 4-methoxyphenyl, or 3,4-dimethoxyphenyl;

or a pharmaceutically acceptable salt, pharmaceutically acceptable prodrug, or pharmaceutically active metabolite of such compound.

In certain preferred embodiments of the inventive method, the disease, disorder, or medical condition is selected from: anxiety, pain, sleep disorders, eating disorders, inflammation, multiple sclerosis and other movement disorders, HIV wasting syndrome, closed head injury, stroke, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, and neuroinflammation.

Additional embodiments, features, and advantages of the invention will be apparent from the following detailed description as well as the appended claims.

DETAILED DESCRIPTION OF INVENTION AND ITS PREFERRED EMBODIMENTS

The invention may be more fully appreciated by reference to the following description, including the following glossary of terms and the concluding examples. For the sake of brevity, the disclosures of the publications cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Exemplary alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and the like.

The term "alkylene" refers to a divalent straight- or branched-chain alkyl group having from 1 to 12 carbon atoms in the chain. Exemplary alkylene groups include methylene, ethylene, propylene, and the like.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and the like.

The term "alkynyl" refers to a straight- or branched-chain alkynyl group having from 2 to 12 carbon atoms in the chain. (The triple bond of the alkynyl group is formed by two sp hybridized carbon atoms.) Illustrative alkynyl groups include prop-2-ynyl, but-2-ynyl, but-3-ynyl, 2-methylbut-2-ynyl, hex-2-ynyl, and the like.

The term "aryl" refers to a monocyclic, or fused or spiro polycyclic, aromatic carbocycle (ring structure having ring atoms that are all carbon) having from 3 to 12 ring atoms per ring. (Carbon atoms in aryl groups are $sp^2$ hybridized.) Illustrative examples of aryl groups include the following moieties:

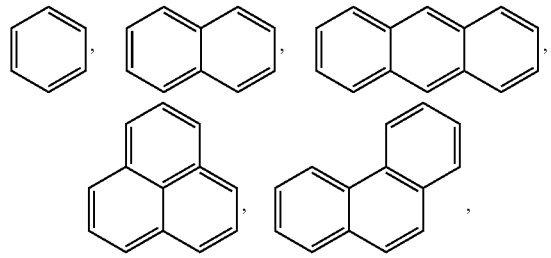

and the like.

The term "heteroaryl" refers to a monocyclic, or fused or spiro bicyclic or polycyclic, aromatic heterocycle (ring structure having ring atoms selected from carbon atoms as well as nitrogen, oxygen, and sulfur heteroatoms) having from 3 to 12 ring atoms per ring. Illustrative examples of heteroaryl groups include the following moieties:

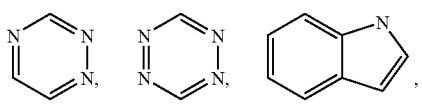

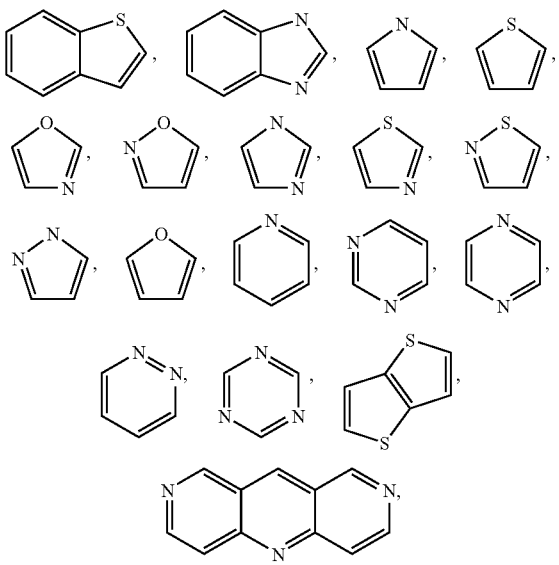

and the like.

The term "cycloalkyl" refers to a saturated or partially saturated, monocyclic or fused or spiro polycyclic, carbocycle having from 3 to 12 ring atoms per ring. Illustrative examples of cycloalkyl groups include the following moieties:

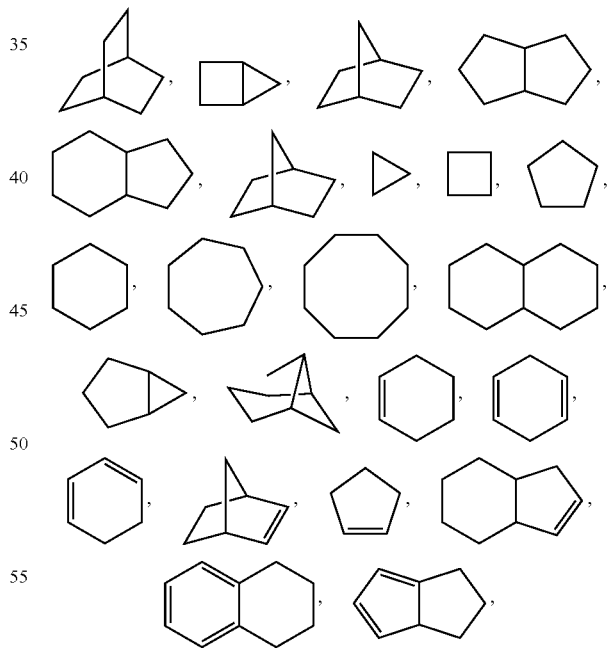

and the like.

A "heterocycloalkyl" refers to a monocyclic, or fused or spiro polycyclic, ring structure that is saturated or partially saturated and has from 3 to 12 ring atoms per ring selected from C atoms and N, O, and S heteroatoms. Illustrative examples of heterocycloalkyl groups include:

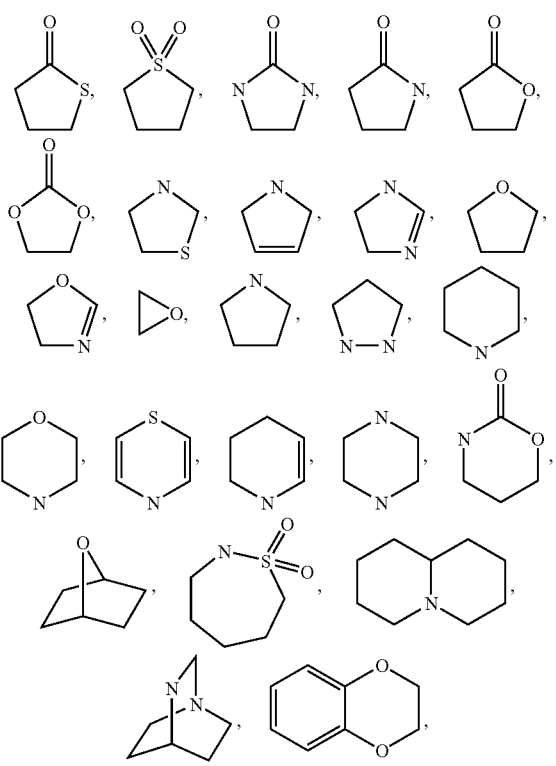

and the like.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system.

Formula (I) is intended to represent compounds having structures depicted by the structural formula as well as certain variations or forms. In particular, compounds of Formula (I) may have asymmetric centers and therefore exist in different enantiomeric forms. All optical isomers and stereoisomers of the compounds of the general formula, and mixtures thereof, are considered within the scope of the formula. Thus Formula (I) is intended to represent a racemate, one or more enantiomeric forms, one or more diastereomeric forms, and mixtures thereof.

Furthermore, certain structures depicted by Formula (I) may exist as geometric isomers (i.e., cis and trans isomers) or as tautomers. Additionally, Formula (I) is intended to represent hydrates, solvates, and polymorphs of such compounds, and mixtures thereof.

Formula (I) is also intended to represent unlabeled forms as well as isotopically labeled forms of the compounds. Isotopically labeled compounds have structures depicted by Formula (I) except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulfur, phosphorous, fluorine and chlorine, such as $^2$H, $^3$H, $^{11}$C, $^3$C, $^{14}$C, $^{15}$N, $^{18}$O, $^{17}$O, $^{31}$P, $^{32}$P, $^{35}$S, $^{18}$F, and $^{36}$Cl, respectively. Various isotopically labeled compounds of the present invention, for example those into which radioactive isotopes such as $^3$H, $^{11}$C, and $^{14}$C are incorporated, are useful in drug or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to Formula (I), the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of compounds of Formula (I), the variable Z is —N—.

In other preferred embodiments, the variable $R^1$ is —H, methyl, ethyl, isopropyl, propyl, or t-butyl. More preferably, $R^1$ is —H. Alternatively, $R^1$ is methyl.

Preferably, $Ar^1$ is 2-pyridyl, 3-pyridyl, 4-pyridyl, 2-pyrimidinyl, or 4-pyrimidinyl, each unsubstituted or substituted at a carbon ring atom with one or two $R^a$ moieties as previously defined. Alternatively, $Ar^1$ is 2-thiazolyl. In an alternate embodiment, $Ar^1$ is phenyl unsubstituted or substituted at a carbon ring atom with one or two $R^a$ moieties as previously defined. When $Ar^1$ is 2-pyridyl, 3-pyridyl, 4-pyridyl, 2-pyrimidinyl, 4-pyrimidinyl, 5-pyrimidinyl, or phenyl, substituted with one or more $R^a$ substituents, preferably each $R^a$ is independently selected from methyl, ethyl, isopropyl, tert-butyl, vinyl, allyl, hydroxyl, methoxy, ethoxy, isopropoxy, fluoro, bromo, chloro, iodo, —CF$_3$, —OCF$_3$, methylsulfanyl, methylsulfoxy, methylsulfonyl, ethylsulfonyl, isopropylsulfonyl, methanesulfonyloxy, carbomethoxy, —CO$_2$H, acetyl, propionyl, amino, methylamino, dimethylamino, ethylmethylamino, —SO$_2$NH$_2$, —SO$_2$NHCH$_3$, —NHSO$_2$CH$_3$, —C(=O)NH$_2$, —C(=O)NHCH$_3$, —NO$_2$, and —CN. More preferably, $R^a$ is independently selected from the group consisting of fluoro, bromo, iodo, methoxy, methyl, carbomethoxy, and carboxy. In some preferred embodiments, $Ar^1$ is 2-fluorophenyl, 3-fluorophenyl, 4-fluorophenyl, 2,4-difluorophenyl, 2-chlorophenyl, 3-chlorophenyl, 4-chlorophenyl, 2-methylphenyl, 3-methylphenyl, 4-methylphenyl, 2-methoxyphenyl, 3-methoxyphenyl, 4-methoxyphenyl, 2-carbomethoxyphenyl, 3-carbomethoxyphenyl, 4-carbomethoxyphenyl, 2-carboxyphenyl, 3-carboxyphenyl, or unsubstituted phenyl.

Preferably, the substituent on variable $Ar^2$ designated as $R^e$ is methyl, ethyl, isopropyl, tert-butyl, vinyl, allyl, hydroxyl, methoxy, ethoxy, isopropoxy, fluoro, bromo, chloro, iodo, —CF$_3$, —OCF$_3$, methylsulfanyl, methylsulfoxy, methylsulfonyl, ethylsulfonyl, isopropylsulfonyl, methanesulfonyloxy, carbomethoxy, —CO$_2$H, acetyl, propionyl, amino, methylamino, dimethylamino, ethylmethylamino, —SO$_2$NH$_2$, —SO$_2$NHCH$_3$, —NHSO$_2$CH$_3$, —C(=O)NH$_2$, —C(=O) NHCH$_3$, —NO$_2$, or —CN.

Preferably, $Ar^2$ is phenanthren-9-yl, pyren-1-yl, 9H-fluoren-2-yl, 1-naphthyl, 2-naphthyl, 1-hydroxynaphthalen-2-yl, 6-methoxynaphthalen-2-yl, 9-ethyl-9H-carbazol-3-yl, furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, tetrazolyl, indolyl, benzofuranyl, benzothiophenyl, benzoxazolyl, benzothiazolyl, benzimidazolyl, indazolyl, imidazo[1,2-a]pyridinyl, pyrazolo[1,5-a]pyridinyl, 1H-pyrrolo[3,2-b]pyridinyl, 1H-pyrrolo[2,3-b]pyridinyl, 1H-pyrrolo[3,2-c]pyridinyl, 1H-pyrrolo[2,3-c]pyridinyl, 1H-pyrrolo[3,2-b]pyridinyl, isoquinolinyl, quinolinyl, quinoxalinyl, quinazolinyl, indanyl, indenyl, tetrahydronaphthyl, 2,3-dihydro-benzofuranyl, chromanyl, 2,3-dihydro-benzo[1,4]dioxinyl, and 2,2-difluoro-benzo[1,3]dioxolyl, pyrimidinyl, pyrazinyl, or pyridyl, each unsubstituted or substituted with one, two, or three $R^e$ substituents as previously defined.

More preferably, $Ar^2$ is 1-phenyl-1H-pyrrolyl, 2-pyridyl, 3-pyridyl, 4-pyridyl, or 6-bromo-pyridin-2-yl, each unsubstituted or substituted with one, two, or three $R^e$ substituents as previously defined. In other more preferred embodiments, $Ar^2$ is unsubstituted 2,2-difluoro-benzo[1,3]dioxolyl or unsubstituted 4-benzo[1,3]dioxolyl. More preferably, $Ar^2$ is 2-indolyl, 3-indolyl, 2-quinolinyl, 3-quinolinyl, or 2-quinoxalinyl, each unsubstituted or substituted with one, two, or three $R^e$ substituents as previously defined. Even more preferably, $Ar^2$ is 2-quinolinyl or 3-quinolinyl.

In alternative embodiments, $Ar^2$ is phenyl, substituted at the 3- or 4-position with a moiety selected from the group consisting of ethyl, propyl, isopropyl, butyl, isobutyl, pentyl, hexyl, octyl, vinyl, allyl, cyclopropyloxy, cyclobutyloxy, cyclopentyloxy, cyclohexyloxy, cycloheptyloxy, 2-dimethylaminoethoxy, 2-dimethylaminopropoxy, 4-piperidinyloxy, ethoxy, propoxy, isopropoxy, isobutyloxy, pentyloxy, hexyloxy, heptyloxy, octyloxy, nonyloxy, decyloxy, 2-piperidin-1-ylethoxy, and 3-piperidin-1-ylpropoxy.

Preferably, $R^i$ and $R^j$ are each independently selected from the group consisting of hydrogen, methyl, ethyl, propyl, isopropyl, butyl, isobutyl, and t-butyl.

Alternatively, $R^i$ and $R^j$ are taken together with the nitrogen ring atom of attachment to form a ring selected from the group consisting of pyrrolidinyl, pyrazolinyl, piperidinyl, homopiperidinyl, azepanyl, tetrahydrofuranyl, tetrahydropyranyl, piperazinyl, morpholinyl, and thiomorpholinyl.

Preferably, $Ar^2$ is 4-ethylphenyl, 4-isopropylphenyl, 3-vinylphenyl, 3-ethoxyphenyl, 4-ethoxyphenyl, 3-propoxyphenyl, 4-propoxyphenyl, 3-isobutoxyphenyl, 4-isopropoxyphenyl, 3-isobutoxyphenyl, 4-isobutoxyphenyl, 4-cyclohexyloxyphenyl, 3-(2-dimethylaminoethoxy)phenyl, 3-(2-piperidin-1-ylethoxy)phenyl, 3-(3-dimethylaminopropoxy)phenyl, or 3-(3-piperidin-1-ylpropoxy)phenyl.

Preferably, L is methylene, ethylene, propylene, alkenylene, —O—, methylenyloxy, —NH—, >$NC_{1-4}$alkyl, —S—, —S(=O)—, —S(=O)$_2$—, —OSO$_2$—, alkynylene, or a covalent bond. More preferably, L is —CH=CH—, —O—, —OCH$_2$—, —SO$_2$—, —OSO$_2$—, or a covalent bond.

Preferably, $Ar^3$ is phenyl, naphthyl, phenanthrenyl, pyridyl, pyrimidinyl, pyrazinyl, furanyl, oxazolyl, isoxazolyl, 1,2,3-oxadiazolyl, 1,2,4-oxadiazolyl, 1,2,5-oxadiazolyl, 1,3,4-oxadiazolyl, thiophenyl, thiazolyl, isothiazolyl, pyrrolyl, imidazolyl, pyrazolyl, 1,2,3-triazolyl, 1,2,4-triazolyl, tetrazolyl, indolyl, benzofuranyl, benzothiophenyl, benzoxazolyl, benzothiazolyl, benzimidazolyl, indazolyl, imidazo[1,2-a]pyridinyl, pyrazolo[1,5-a]pyridinyl, 1H-pyrrolo[3,2-b]pyridinyl, 1H-pyrrolo[2,3-b]pyridinyl, 1H-pyrrolo[3,2-c]pyridinyl, 1H-pyrrolo[2,3-c]pyridinyl, 1H-pyrrolo[3,2-b]pyridinyl, isoquinolinyl, quinolinyl, quinoxalinyl, or quinazolinyl.

More preferably, $Ar^3$ is phenyl, 4-chlorophenyl, 3,4-dichlorophenyl, 4-methylphenyl, 4-t-butylphenyl, 3-trifluoromethylphenyl, 4-methoxyphenyl, 3,5-dichlorophenyl, 1-naphthyl, 2-naphthyl, 3-chlorophenyl, 9-phenanthrenyl, 4-carbomethoxyphenyl, 4-methanesulfonylphenyl, 3-methoxyphenyl, or benzo[1,3]dioxol-5-yl.

Preferably, $Ar^2$ is 2-hydroxyphenyl, unsubstituted or substituted with a moiety selected from the group consisting of methyl, 6-ethyl, 6-isopropyl, 6-tert-butyl, 6-vinyl, 6-allyl, hydroxyl, methoxy, 6-ethoxy, 6-isopropoxy, fluoro, bromo, chloro, iodo, —CF$_3$, —OCF$_3$, methylsulfanyl, methylsulfoxy, methylsulfonyl, ethylsulfonyl, isopropylsulfonyl, carbomethoxy, —CO$_2$H, acetyl, propionyl, amino, methylamino, dimethylamino, ethylmethylamino, —SO$_2$NH$_2$, —SO$_2$NHCH$_3$, —NHSO$_2$CH$_3$, —C(=O)NH$_2$, —C(=O)NHCH$_3$, —NO$_2$, and —CN. Alternatively, $Ar^2$ is 2-methoxyphenyl, optionally substituted as described above.

More preferably, $Ar^2$ is 2-hydroxyphenyl, 5-bromo-2-hydroxy-3-methoxyphenyl, or 5-bromo-2-hydroxyphenyl.

Preferably, $Ar^2$ is 4-halophenyl, unsubstituted or substituted with a moiety selected from the group consisting of methyl, 2-ethyl, 2-isopropyl, 2-tert-butyl, 2-vinyl, 2-allyl, 3-hydroxy, 4-hydroxy, methoxy, 2-ethoxy, 2-isopropoxy, fluoro, bromo, chloro, iodo, —CF$_3$, —OCF$_3$, methylsulfanyl, methylsulfoxy, methylsulfonyl, ethylsulfonyl, isopropylsulfonyl, carbomethoxy, —CO$_2$H, acetyl, propionyl, amino, methylamino, dimethylamino, ethylmethylamino, —SO$_2$NH$_2$, —SO$_2$NHCH$_3$, —NHSO$_2$CH$_3$, —C(=O)NH$_2$, —C(=O)NHCH$_3$, —NO$_2$, and —CN; and $Ar^1$ is phenyl.

More preferably, $Ar^2$ is 3,4-dibromophenyl, 3-bromo-4-fluorophenyl, or 4-chloro-3-trifluoromethyl. Alternatively, $Ar^2$ is 3,4-dichlorophenyl.

Even more preferably, $Ar^2$ is 3,4-dibromophenyl.

Preferred compounds of the present invention include the following:

4-Naphthalen-2-ylmethyl-piperazine-1-carboxylic acid phenylamide;

4-Quinolin-2-ylmethyl-piperazine-1-carboxylic acid phenylamide;

4-Benzo[b]thiophen-2-ylmethyl-piperazine-1-carboxylic acid phenylamide;

4-(3,4-Dibromo-benzyl)-piperazine-1-carboxylic acid phenylamide;

4-(1-Methyl-1H-indol-2-ylmethyl)-piperazine-1-carboxylic acid phenylamide;

4-Quinolin-3-ylmethyl-piperazine-1-carboxylic acid phenylamide;

4-(4-Iodo-benzyl)-piperazine-1-carboxylic acid phenylamide;

4-(3-Benzyloxy-benzyl)-piperazine-1-carboxylic acid phenylamide;

4-(5-Bromo-2-hydroxy-3-methoxy-benzyl)-piperazine-1-carboxylic acid phenylamide;

4-(4-Bromo-benzyl)-piperazine-1-carboxylic acid phenylamide;

4-(3-Phenoxy-benzyl)-piperazine-1-carboxylic acid phenylamide;

4-(3-Bromo-4-fluoro-benzyl)-piperazine-1-carboxylic acid phenylamide;

4-Indan-5-ylmethyl-piperazine-1-carboxylic acid phenylamide;

4-Benzo[b]thiophen-3-ylmethyl-piperazine-1-carboxylic acid phenylamide;

4-(4-Isopropyl-benzyl)-piperazine-1-carboxylic acid phenylamide;
4-(4-Ethyl-benzyl)-piperazine-1-carboxylic acid phenylamide;
4-(5-Bromo-2-hydroxy-benzyl)-piperazine-1-carboxylic acid phenylamide;
4-(2,3-Dihydro-benzo[1,4]dioxin-6-ylmethyl)-piperazine-1-carboxylic acid phenylamide;
4-(4-Methoxy-benzyl)-piperazine-1-carboxylic acid phenylamide;
4-(3-Vinyl-benzyl)-piperazine-1-carboxylic acid phenylamide;
4-(2,3-Dihydro-benzofuran-5-ylmethyl)-piperazine-1-carboxylic acid phenylamide;
4-(3-Methoxy-benzyl)-piperazine-1-carboxylic acid phenylamide;
4-Naphthalen-1-ylmethyl-piperazine-1-carboxylic acid phenylamide;
4-(2-Hydroxy-benzyl)-piperazine-1-carboxylic acid phenylamide;
4-(3-Methyl-benzyl)-piperazine-1-carboxylic acid phenylamide;
4-(1H-Indol-5-ylmethyl)-piperazine-1-carboxylic acid phenylamide;
4-(3,4-Dimethoxy-benzyl)-piperazine-1-carboxylic acid phenylamide;
4-Pyridin-4-ylmethyl-piperazine-1-carboxylic acid phenylamide;
4-Pyridin-2-ylmethyl-piperazine-1-carboxylic acid phenylamide;
4-Pyridin-3-ylmethyl-piperazine-1-carboxylic acid phenylamide;
4-(4-Isopropoxy-benzyl)-piperazine-1-carboxylic acid phenylamide;
4-Biphenyl-4-ylmethyl-piperazine-1-carboxylic acid phenylamide;
4-Quinolin-4-ylmethyl-piperazine-1-carboxylic acid phenylamide;
4-Benzo[1,3]dioxol-4-ylmethyl-piperazine-1-carboxylic acid phenylamide;
4-(2,2-Difluoro-benzo[1,3]dioxol-5-ylmethyl)-piperazine-1-carboxylic acid phenylamide;
4-(1-Methyl-1H-indol-5-ylmethyl)-piperazine-1-carboxylic acid phenylamide;
4-(6-Chloro-quinolin-2-ylmethyl)-piperazine-1-carboxylic acid phenylamide;
4-(8-Chloro-quinolin-2-ylmethyl)-piperazine-1-carboxylic acid phenylamide;
4-(2-Chloro-quinolin-3-ylmethyl)-piperazine-1-carboxylic acid phenylamide;
4-Naphthalen-2-ylmethyl-piperazine-1-carboxylic acid (4-fluoro-phenyl)-amide;
4-Quinolin-2-ylmethyl-piperazine-1-carboxylic acid (4-fluoro-phenyl)-amide;
4-(1-Hydroxy-naphthalen-2-ylmethyl)-piperazine-1-carboxylic acid phenylamide;
4-[3-(4-Chloro-phenoxy)-benzyl]-piperazine-1-carboxylic acid phenylamide;
4-[3-(3,4-Dichloro-phenoxy)-benzyl]-piperazine-1-carboxylic acid phenylamide;
4-(3-p-Tolyloxy-benzyl)-piperazine-1-carboxylic acid phenylamide;
4-[3-(4-tert-Butyl-phenoxy)-benzyl]-piperazine-1-carboxylic acid phenylamide;
4-[3-(3-Trifluoromethyl-phenoxy)-benzyl]-piperazine-1-carboxylic acid phenylamide;
4-[3-(4-Methoxy-phenoxy)-benzyl]-piperazine-1-carboxylic acid phenylamide;
4-(6-Methoxy-naphthalen-2-ylmethyl)-piperazine-1-carboxylic acid phenylamide;
4-Phenanthren-9-ylmethyl-piperazine-1-carboxylic acid phenylamide;
4-Pyren-1-ylmethyl-piperazine-1-carboxylic acid phenylamide;
4-(6-Chloro-quinolin-3-ylmethyl)-piperazine-1-carboxylic acid phenylamide;
4-Biphenyl-3-ylmethyl-piperazine-1-carboxylic acid phenylamide;
4-(6-Bromo-pyridin-2-ylmethyl)-piperazine-1-carboxylic acid phenylamide;
4-[3-(4-Chloro-benzenesulfonyl)-benzyl]-piperazine-1-carboxylic acid phenylamide;
4-(1H-Indol-6-ylmethyl)-piperazine-1-carboxylic acid phenylamide;
4-(4-Phenoxy-benzyl)-piperazine-1-carboxylic acid phenylamide;
4-(2-Chloro-8-methyl-quinolin-3-ylmethyl)-piperazine-1-carboxylic acid phenylamide;
4-(1-Methyl-1H-indol-6-ylmethyl)-piperazine-1-carboxylic acid phenylamide;
4-(4-Benzyloxy-benzyl)-piperazine-1-carboxylic acid phenylamide;
4-[3-(3,5-Dichloro-phenoxy)-benzyl]-piperazine-1-carboxylic acid phenylamide;
4-(9H-Fluoren-2-ylmethyl)-piperazine-1-carboxylic acid phenylamide;
4-(9-Ethyl-9H-carbazol-3-ylmethyl)-piperazine-1-carboxylic acid phenylamide;
4-(4-Styryl-benzyl)-piperazine-1-carboxylic acid phenylamide;
4-(4-Chloro-3-trifluoromethyl-benzyl)-piperazine-1-carboxylic acid phenylamide;
4-[2,5-Dimethyl-1-(3-trifluoromethyl-phenyl)-1H-pyrrol-3-ylmethyl]-piperazine-1-carboxylic acid phenylamide;
4-(2-Bromo-benzyl)-piperazine-1-carboxylic acid phenylamide;
4-(3,4-Dibromo-benzyl)-piperazine-1-carboxylic acid (3-fluoro-phenyl)-amide;
4-(3,4-Dibromo-benzyl)-piperazine-1-carboxylic acid (4-fluoro-phenyl)-amide;
4-(3,4-Dibromo-benzyl)-piperazine-1-carboxylic acid (3-methoxy-phenyl)-amide;
4-(3,4-Dibromo-benzyl)-piperazine-1-carboxylic acid m-tolylamide;
4-(3,4-Dibromo-benzyl)-piperazine-1-carboxylic acid (2-fluoro-phenyl)-amide;
4-(3,4-Dibromo-benzyl)-piperazine-1-carboxylic acid (4-methoxy-phenyl)-amide;
4-(3,4-Dibromo-benzyl)-piperazine-1-carboxylic acid (2-methoxy-phenyl)-amide;
4-(3,4-Dibromo-benzyl)-piperazine-1-carboxylic acid (3-chloro-phenyl)-amide;
4-(3,4-Dibromo-benzyl)-piperazine-1-carboxylic acid (2-chloro-phenyl)-amide;
4-(3,4-Dibromo-benzyl)-piperazine-1-carboxylic acid p-tolylamide;
4-(3,4-Dibromo-benzyl)-piperazine-1-carboxylic acid (4-chloro-phenyl)-amide;
4-(3,4-Dibromo-benzyl)-piperazine-1-carboxylic acid o-tolylamide;
4-Quinolin-3-ylmethyl-piperazine-1-carboxylic acid (3-fluoro-phenyl)-amide;

4-Quinolin-3-ylmethyl-piperazine-1-carboxylic acid (4-fluoro-phenyl)-amide;
4-Quinolin-3-ylmethyl-piperazine-1-carboxylic acid (2-chloro-phenyl)-amide;
4-Quinolin-3-ylmethyl-piperazine-1-carboxylic acid (3-chloro-phenyl)-amide;
4-Quinolin-3-ylmethyl-piperazine-1-carboxylic acid (4-chloro-phenyl)-amide;
4-Quinolin-3-ylmethyl-piperazine-1-carboxylic acid (2-methoxy-phenyl)-amide;
4-Quinolin-3-ylmethyl-piperazine-1-carboxylic acid o-tolylamide;
4-Quinolin-3-ylmethyl-piperazine-1-carboxylic acid p-tolylamide;
2-[(4-Quinolin-3-ylmethyl-piperazine-1-carbonyl)-amino]-benzoic acid methyl ester;
3-[(4-Quinolin-3-ylmethyl-piperazine-1-carbonyl)-amino]-benzoic acid methyl ester;
4-[(4-Quinolin-3-ylmethyl-piperazine-1-carbonyl)-amino]-benzoic acid methyl ester;
4-Quinolin-3-ylmethyl-piperazine-1-carboxylic acid (4-methoxy-phenyl)-amide;
4-Quinolin-3-ylmethyl-piperazine-1-carboxylic acid m-tolylamide;
4-Quinolin-3-ylmethyl-piperazine-1-carboxylic acid (3-methoxy-phenyl)-amide;
4-Quinolin-3-ylmethyl-piperazine-1-carboxylic acid (2,4-difluoro-phenyl)-amide;
4-Quinolin-3-ylmethyl-piperazine-1-carboxylic acid (2-fluoro-phenyl)-amide;
4-Benzyl-piperidine-1-carboxylic acid p-tolylamide;
4-Benzyl-piperidine-1-carboxylic acid m-tolylamide;
4-Benzyl-piperidine-1-carboxylic acid (2-chloro-phenyl)-amide;
4-(3,4-Dibromo-benzyl)-piperazine-1-carboxylic acid pyridin-4-ylamide;
4-(3,4-Dibromo-benzyl)-piperazine-1-carboxylic acid pyridin-2-ylamide;
4-(3,4-Dibromo-benzyl)-piperazine-1-carboxylic acid pyridin-3-ylamide;
4-(4-Cyclohexyloxy-benzyl)-piperazine-1-carboxylic acid phenylamide;
4-(3-Propoxy-benzyl)-piperazine-1-carboxylic acid phenylamide;
4-(3-Isobutoxy-benzyl)-piperazine-1-carboxylic acid phenylamide;
4-(3-Ethoxy-benzyl)-piperazine-1-carboxylic acid phenylamide;
4-(4-Propoxy-benzyl)-piperazine-1-carboxylic acid phenylamide;
4-(4-Isobutoxy-benzyl)-piperazine-1-carboxylic acid phenylamide;
4-[3-(2-Dimethylamino-ethoxy)-benzyl]-piperazine-1-carboxylic acid phenylamide;
4-[3-(2-Piperidin-1-yl-ethoxy)-benzyl]-piperazine-1-carboxylic acid phenylamide;
4-[3-(3-Dimethylamino-propoxy)-benzyl]-piperazine-1-carboxylic acid phenylamide;
4-[3-(3-Piperidin-1-yl-propoxy)-benzyl]-piperazine-1-carboxylic acid phenylamide;
4-(4-Ethoxy-benzyl)-piperazine-1-carboxylic acid phenylamide;
4-[3-(3-Chloro-phenoxy)benzyl]-piperazine-1-carboxylic acid phenylamide;
4-[3-(Naphthalen-2-yloxy)-benzyl]-piperazine-1-carboxylic acid phenylamide;
4-[3-(Phenanthren-9-yloxy)-benzyl]-piperazine-1-carboxylic acid phenylamide;
4-[3-(4-Phenylcarbamoyl-piperazin-1-ylmethyl)-phenoxy]-benzoic acid methyl ester;
4-[3-(4-Methanesulfonyl-phenoxy)-benzyl]-piperazine-1-carboxylic acid phenylamide;
4-[3-(3-Methoxy-phenoxy)-benzyl]-piperazine-1-carboxylic acid phenylamide;
4-[3-(Benzo[1,3]dioxol-5-yloxy)-benzyl]-piperazine-1-carboxylic acid phenylamide;
Methanesulfonic acid 3-(4-phenylcarbamoyl-piperazin-1-ylmethyl)-phenyl ester;
Benzenesulfonic acid 3-(4-phenylcarbamoyl-piperazin-1-ylmethyl)-phenyl ester;
4-Chloro-benzenesulfonic acid 3-(4-phenylcarbamoyl-piperazin-1-ylmethyl)-phenyl ester;
2-[(4-Quinolin-3-ylmethyl-piperazine-1-carbonyl)-amino]-benzoic acid (potassium salt);
3-[(4-Quinolin-3-ylmethyl-piperazine-1-carbonyl)-amino]-benzoic acid (potassium salt);
4-Quinolin-3-ylmethyl-piperazine-1-carboxylic acid pyridin-3-ylamide;
4-Quinolin-3-ylmethyl-piperazine-1-carboxylic acid pyridin-2-ylamide;
4-Quinolin-3-ylmethyl-piperazine-1-carboxylic acid pyridin-4-ylamide;
4-Quinolin-3-ylmethyl-piperazine-1-carboxylic acid pyrimidin-2-ylamide;
4-Benzo[1,3]dioxol-5-ylmethyl-piperazine-1-carboxylic acid pyridin-3-ylamide;
4-Benzo[1,3]dioxol-5-ylmethyl-piperazine-1-carboxylic acid pyridin-4-ylamide;
4-Benzo[1,3]dioxol-5-ylmethyl-piperazine-1-carboxylic acid pyrimidin-2-ylamide;
4-Benzo[1,3]dioxol-5-ylmethyl-piperazine-1-carboxylic acid pyridin-2-ylamide;
4-(2,2-Difluoro-benzo[1,3]dioxol-5-ylmethyl)-piperazine-1-carboxylic acid pyridin-3-ylamide;
4-(2,2-Difluoro-benzo[1,3]dioxol-5-ylmethyl)-piperazine-1-carboxylic acid pyridin-4-ylamide;
4-Quinolin-3-ylmethyl-piperazine-1-carboxylic acid pyrimidin-4-ylamide;
4-(2,2-Difluoro-benzo[1,3]dioxol-5-ylmethyl)-piperazine-1-carboxylic acid pyrimidin-4-ylamide;
4-(3,4-Dibromo-benzyl)-piperazine-1-carboxylic acid pyrimidin-4-ylamide;
4-[(4-Quinolin-3-ylmethyl-piperazine-1-carbonyl)-amino]-benzoic acid;
4-Quinoxalin-2-ylmethyl-piperazine-1-carboxylic acid phenylamide;
4-(3,4-Dichloro-benzyl)-piperazine-1-carboxylic acid phenylamide;
4-Quinolin-3-ylmethyl-piperazine-1-carboxylic acid thiazol-2-ylamide;
4-Benzo[1,3]dioxol-5-ylmethyl-piperazine-1-carboxylic acid thiazol-2-ylamide;
4-(3,4-Dibromo-benzyl)-piperazine-1-carboxylic acid methyl-phenyl-amide;
4-(2-Methoxy-benzyl)-piperazine-1-carboxylic acid phenylamide;
4-Benzofuran-2-ylmethyl-piperazine-1-carboxylic acid phenylamide;
4-(3,4-Dibromo-benzyl)-piperazine-1-carboxylic acid (4-nitro-phenyl)-amide;
4-(3,4-Dibromo-benzyl)-piperazine-1-carboxylic acid (4-trifluoromethyl-phenyl)-amide;

4-(5-Bromo-2-hydroxy-3-methoxy-benzyl)-piperazine-1-carboxylic acid phenylamide hydrochloride;
4-(3,4-Dibromo-benzyl)-piperazine-1-carboxylic acid phenylamide hydrochloride;
4-Quinolin-2-ylmethyl-piperazine-1-carboxylic acid phenylamide dihydrochloride;
4-Benzo[1,3]dioxol-5-ylmethyl-piperazine-1-carboxylic acid phenylamide;
4-Benzo[1,3]dioxol-5-ylmethyl-piperazine-1-carboxylic acid phenylamide hydrochloride; and
4-Benzo[1,3]dioxol-5-ylmethyl-piperazine-1-carboxylic acid (4-fluoro-phenyl)-amide.

The invention includes also pharmaceutically acceptable salts of the compounds represented by Formula (I), such as of those described above. Pharmaceutically acceptable salts of the specific compounds exemplified herein are especially preferred.

A "pharmaceutically acceptable salt" is intended to mean a salt of a free acid or base of a compound represented by Formula (I) that is not toxic, biologically intolerable, or otherwise biologically undesirable. See, generally, e.g., S. M. Berge, et al., "Pharmaceutical Salts", J. Pharm. Sci., 1977, 66:1-19, and *Handbook of Pharmaceutical Salts, Properties, Selection, and Use*; Stahl, P. H., Wermuth, C. G., Eds.; Wiley-VCH and VHCA: Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Exemplary pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or the like.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to treatment methods employing pharmaceutically acceptable prodrugs of the compounds of Formula (I). The term "prodrug" means a precursor of a designated compound that, following administration to a subject, yields the compound in vivo via a chemical or physiological process such as solvolysis or physiological conditions (e.g., a prodrug on being brought to physiological pH is converted to the compound of Formula (I)). A "pharmaceutically acceptable prodrug" is a prodrug that is not toxic, biologically intolerable, or otherwise biologically unsuitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy or carboxylic acid group of a compound of Formula (I). Examples of amino acid residues include the twenty naturally occurring amino acids commonly designated by three letter symbols as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Exemplary amides include those derived from ammonia, primary $C_{1-6}$alkyl amines and secondary di($C_{1-6}$alkyl) amines. Secondary amines include 5- or 6-membered heterocycloalkyl or heteroaryl ring moieties having from 1 to 3 heteroatoms where at least one is a nitrogen atom. Preferred amides are derived from ammonia, $C_{1-3}$alkyl primary amines, and di($C_{1-2}$alkyl) amines. Exemplary esters of the invention include $C_{1-7}$alkyl, $C_{5-7}$carbocyclyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine and carboxylic acid functionalities.

Pharmaceutically active metabolites may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as FAAH inhibitors in the methods of the invention. The agents may be used in the inventive methods for the treatment or prevention of medical conditions, diseases, or disorders mediated through inhibition or modulation of FAAH, such as those described herein. Agents according to the invention may therefore be used as an analgesic, neuroprotectant, sedative, appetite stimulant, or contraceptive.

Exemplary medical conditions, diseases, and disorders include anxiety, pain, sleep disorders, eating disorders, inflammation, multiple sclerosis and other movement disorders, HIV wasting syndrome, closed head injury, stroke, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, posttraumatic stress disorder, or cerebral vasospasm.

Thus, the pharmaceutical agents may be used to treat subjects diagnosed with or suffering from a disorder or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize or up-regulate FAAH expression or activity.

Accordingly, the invention relates to methods of using the pharmaceutical agents described herein to treat subjects diagnosed with or suffering from a disorder or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases and disorders, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In a treatment method according to the invention, an effective amount of a pharmaceutical agent according to the invention is administered to a subject suffering from or diagnosed as having such a disease, disorder or condition. An "effective amount" means an amount or dose sufficient to generally bring about the desired therapeutic or prophylactic benefit in patients in need of such treatment.

Effective amounts or doses of the agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disorder or condition, the subject's previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's conditions has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the agents of the invention may be used in combination with additional active compounds in the treatment of the above conditions. The additional compounds may be coadministered separately with an agent of Formula (I) or included with such an agent as an additional active ingredient in a pharmaceutical composition according to the invention. In an exemplary embodiment, additional active compounds are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The agents of the invention are used, alone or in combination with one or more other active ingredients, to formulate pharmaceutical compositions of the invention. A pharmaceutical composition of the invention comprises: an effective amount of a pharmaceutical agent in accordance with the invention; and a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent to facilitate administration of a pharmaceutical agent and that is compatible therewith. Examples of excipients include calcium carbonate, calcium phosphate, various sugars and types of starch, cellulose derivatives, gelatin, vegetable oils and polyethylene glycols.

Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents and preservatives agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A:

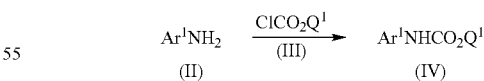

Referring to Scheme A, a compound of formula (IV) may be obtained by reacting a compound of formula (II) with a compound of formula (III), in which $Q^1$ represents an aryl group, under chloroformate condensation conditions. In a preferred embodiment, $Q^1$ is substituted or unsubstituted phenyl, and the reaction occurs in the presence of a base in a solvent at a temperature from 0° C. to 50° C. In a particularly preferred embodiment, $Q^1$ is phenyl, and the reaction occurs in the presence of pyridine in dichloromethane at 0° C. followed by warming to room temperature.

SCHEME B:

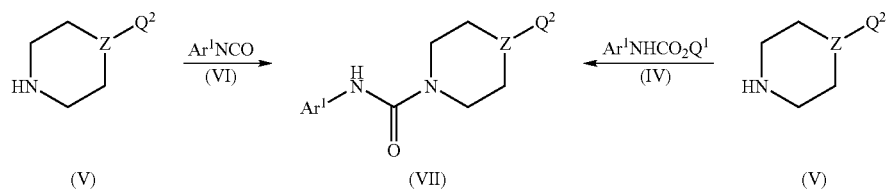

Referring to Scheme B, a compound of formula (VII) is prepared from a compound of formula (V). The group $Q^2$ is either $CH_2Ar^2$ or a nitrogen protecting group $Q^3$ when Z is N. A compound of formula (VII) is obtained by reacting a compound of formula (V) with a compound of formula (VI) under isocyanate addition conditions. In a preferred embodiment, the reaction is performed in a solvent at a temperature from 0° C. to 100° C. Preferred conditions employ dichloromethane at room temperature. Alternatively, a compound of formula (VII) is obtained by reacting a compound of formula (V) with a compound of formula (IV) under aryl carbamate condensation conditions. In a preferred embodiment, the reaction takes place in a solvent at a temperature from room temperature to 120° C. In a particularly preferred embodiment, $Q^1$ is phenyl, and the reaction is performed in DMSO in a microwave reactor at 100° C.

dride, sodium cyanoborohydride, or phenylsilane in a solvent such as THF, DCE, DCM, methanol, ethanol, or diethyl ether at a temperature from 0° C. to 80° C. The use of a promoter or catalyst with acidic character such as organometallic complexes or carboxylic acids may increase the rate of the reaction and/or reduce the formation of byproducts. In a particularly preferred embodiment, sodium triacetoxyborohydride in DCE is employed at room temperature.

Alternatively, a compound of formula (XIII) is obtained by reacting a compound of formula (XI) with a compound of formula (XII) under reductive amination conditions as outlined above. A compound of formula (XVI) is obtained by removing $Q^3$ from a compound of formula (XIII) under deprotection conditions as described above. A compound of formula (XV) is obtained by reacting a compound of formula

SCHEME C:

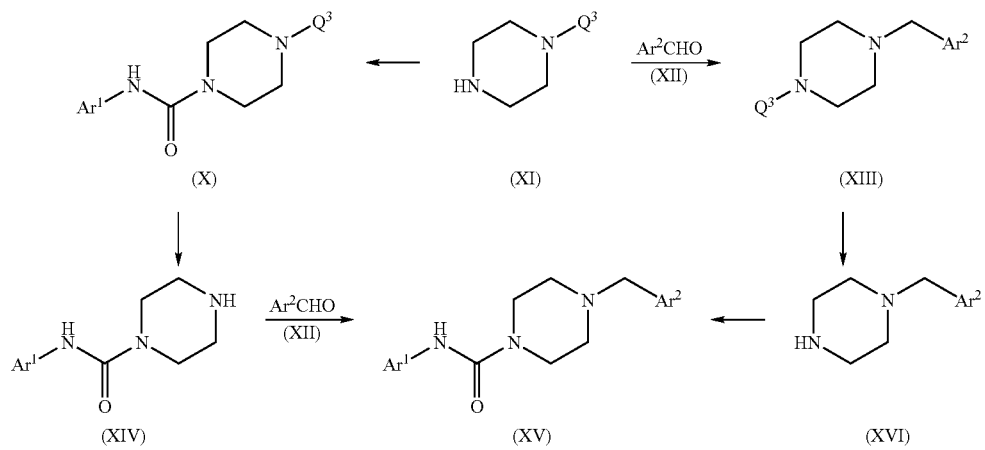

Referring to Scheme C, a compound of formula (XV) is prepared from a compound of formula (XI). A suitable protecting group $Q^3$ compatible with the transformations in Scheme C is selected. Preferably, $Q^3$ is tert-butyl-carbamoyl. A compound of formula (X) is obtained by reacting a compound of formula (XI) with either a compound of formula (VI) or with a compound of formula (IV) as described in Scheme B. An amine of formula (XIV) is obtained by deprotecting a compound of formula (X) with a reagent under suitable $Q^3$ deprotection conditions. In a particularly preferred embodiment, a compound of formula (X), in which $Q^3$ is tert-butyl-carbamoyl, is reacted with ethereal hydrogen chloride in the presence or absence of methanol at room temperature. A compound of formula (XV) is obtained by reacting a compound of formula (XIV) with a compound of formula (XII) under reductive amination conditions in the presence of a reductant such as sodium triacetoxyborohy- (XVI) with either a compound of formula (IV) or with a compound of formula (VI) as described in Scheme B.

SCHEME D:

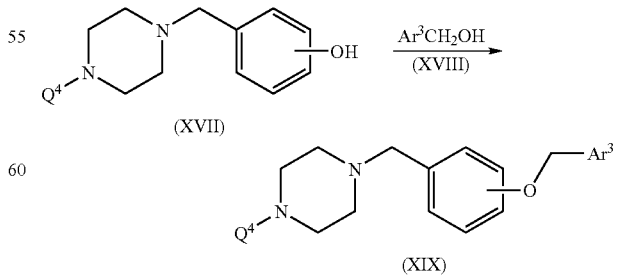

Referring to Scheme D, a compound of formula (XIX) is prepared from a compound of formula (XVII), in which $Q^4$ is either $CONR^1Ar^1$ or the nitrogen protecting group $Q^3$. A compound of formula (XVII) is prepared in analogy with Scheme C. A compound of formula (XIX) is obtained by reacting a compound of formula (XVII) with a compound of formula (XVIII) under Mitsunobu conditions in the presence of a phosphine such as triphenylphosphine or polymer supported triphenyl phosphine, and an azodicarboxylate such as DBAD or DEAD, in an organic solvent such as DCM, THF, and the like.

Referring to Scheme F, a compound of formula (XXIV), where $Q^4$ is defined as above, is obtained by reacting a compound of formula (XVII), where $Ar^3$ is a moiety as defined for Formula (I), with a compound of formula (XXIII), in the presence of a base such as pyridine or triethylamine in a solvent such as DCM at a temperature from 0° C. to room temperature.

SCHEME E:

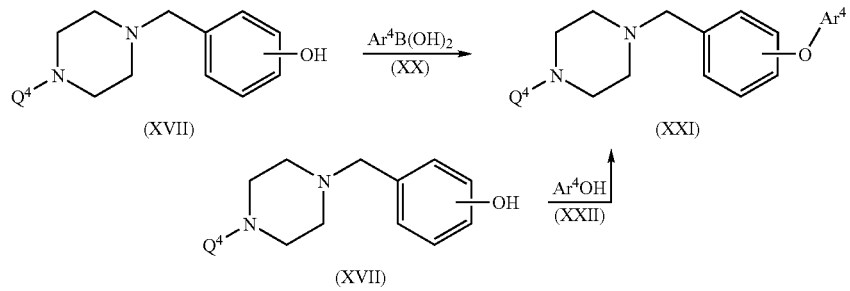

Referring to Scheme E, a compound of formula (XVII), where $Q^4$ is either $CONR^1Ar^1$ or the nitrogen protecting group $Q^3$, prepared in analogy with Scheme C, is converted to a compound of formula (XXI). A compound of formula (XXI), wherein $Ar^4$ is a moiety $Ar^3$ as defined in Formula (I) and is directly bound to the linking oxygen atom, is obtained by reacting a compound of formula (XVII) with a boronic acid (XX) in the presence of a drying agent such as powdered 4 Å molecular sieves, a promoter such as copper(II) acetate, and a base such as pyridine or triethylamine in a solvent such as DCM or DCE. Alternatively, a compound of formula (XXI), in which $Ar^4$ contains an $sp^3$ hybridized carbon atom directly bound to the linking oxygen atom, is prepared by reacting a phenol (XVII) with a compound of formula (XXII) under Mitsunobu conditions as described in Scheme D.

SCHEME F:

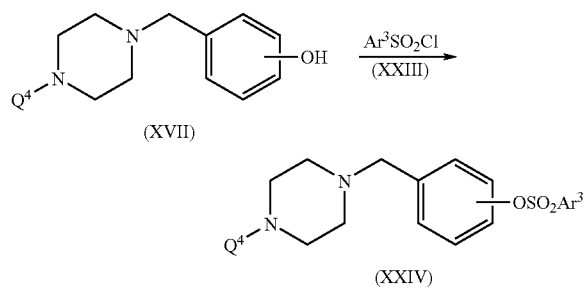

SCHEME G:

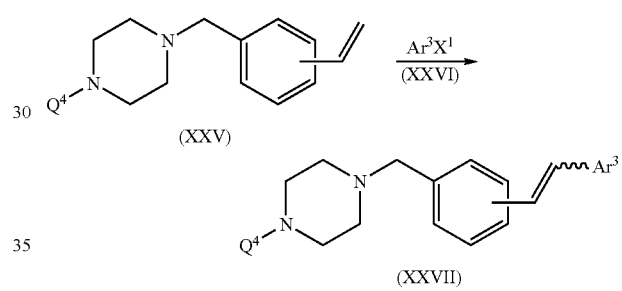

Referring to Scheme G, a compound of formula (XXV), where $Q^4$ is defined as above and where $Ar^3$ is as defined for Formula (I), is obtained as described in Scheme C. Compound (XXV) is converted to a compound of formula (XXVII) by reaction with a compound of formula (XXVI), in which $X^1$ is iodo, bromo, chloro, or trifluoromethanesulfonate ester, under Heck conditions in the presence of a palladium source such as palladium(II) acetate, a phosphine ligand such as triphenylphosphine, an optional promoter such as tetrabutylammonium chloride, and a base such as aqueous potassium carbonate in a solvent such as DMF.

SCHEME H:

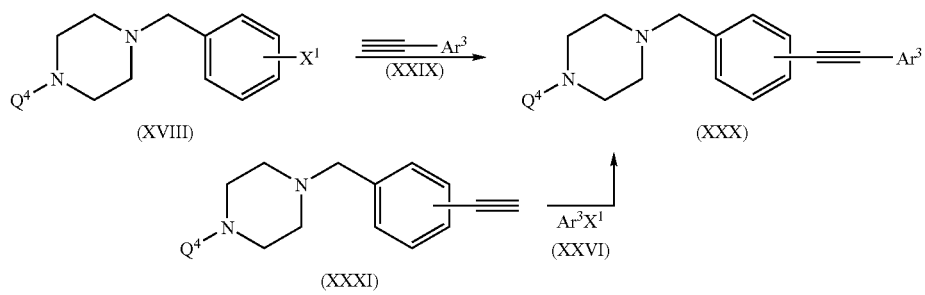

Referring to Scheme H, a compound of formula (XXX), where $Q^4$ is defined as above, is prepared from a compound of formula (XXVIII) or (XXXI), each available from a preparation in analogy with Scheme C. $Ar^3$ and $X^1$ are defined as described above. A compound of formula (XXX) is prepared by reacting a compound of formula (XXVIII) with a compound of formula (XXIX) under Sonogashira conditions in the presence of a palladium-containing entity such as palladium on carbon, $Pd_2(dba)_3$, $Pd_2(dba)_3 \cdot CHCl_3$, $Pd(P^tBu_3)_2$, $Pd_2(dba)_3 \cdot CHCl_3/Pd(P^tBu_3)_2$, $Pd(OAc)_2$, $Pd(PhCN)_2Cl_2$, or $PdCl_2$ and a base such as triethylamine, DIEA, di-iso-propylamine, sodium carbonate, potassium carbonate, or cesium carbonate in a solvent such as THF, DME, dioxane, DCE, DCM, toluene, and acetonitrile at a temperature from 0° C. to 100° C. The use of substoichiometric quantities of a copper salt such as CuI and phosphine ligands such as $PPh_3$ or $P(^tBu)_3$ may be necessary or desirable. Additionally, the use of water as a cosolvent may accelerate the reaction and prevent the formation of byproducts.

Alternatively, a compound of formula (XXX) is prepared by reacting a compound of formula (XXXI) with a compound of formula (XXVI) using Sonogashira conditions.

SCHEME I:

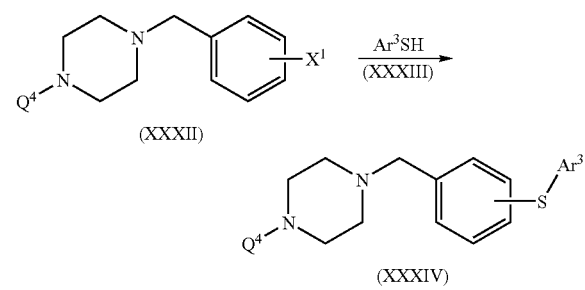

(XXXII)

(XXXIV)

As depicted above, a compound of formula (XXXII), where $Q^4$ is defined as above, prepared in analogy with Scheme C, is reacted with a compound of formula (XXXIII) in the presence of a base such as sodium hydride, and a palladium source such as tetrakis(triphenylphosphine)palladium(0), in a solvent such as n-butanol, at a temperature from room temperature to 116° C.

SCHEME J:

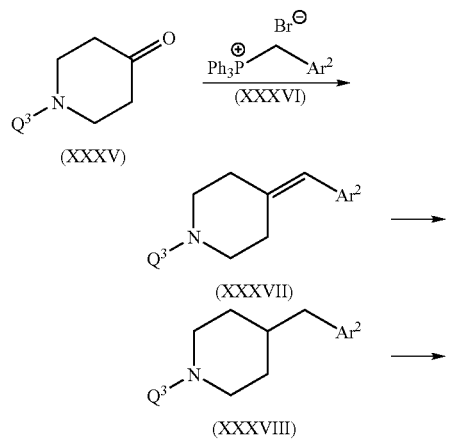

(XXXV)

(XXXVII)

(XXXVIII)

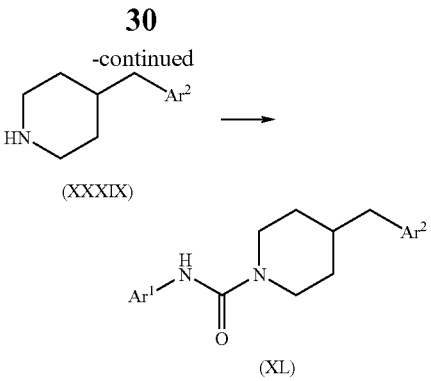

(XXXIX)

(XL)

Referring to Scheme J, a compound of formula (XL) is prepared from a compound of formula (XXXV), in which $Q^3$ is a nitrogen protecting group. A protecting group $Q^3$ compatible with the processes outlined in Scheme J is selected, e.g., benzyl. A compound of formula (XXXVI) may be obtained from a commercial source or may be prepared from a suitable bromide, alcohol, aldehyde, or other precursor following methods known in the art. A compound of formula (XXXVII) is prepared by treating a compound of formula (XXXVI) with a base such as sodium hydride in a solvent such as DMSO followed by treatment with a compound of formula (XXXV). A compound of formula (XXXVIII) is prepared by treating a compound of formula (XXXVII) with a catalyst such as platinum(II) oxide in solvent such as methanol in the presence of 10-100 psi hydrogen gas. A compound of formula (XXXIX) is prepared by reacting a compound of formula (XXXVIII) with a reagent capable of removing the protecting group $Q^3$. In a preferred embodiment, in which $Q^3$ is benzyl, suitable conditions include a catalyst such as palladium on carbon in a solvent such as ethanol in the presence of 20-100 psi hydrogen gas. A compound of formula (XL) is prepared by reacting a compound of formula (XXXIX) with either a compound of formula (IV) or a compound of formula (VI) as described in Scheme B.

The following specific examples are provided to further illustrate the invention and various preferred embodiments.

EXAMPLES

Chemistry

In obtaining the characterization data described in the examples below, the following analytical protocols were followed as indicated.

Preparative Reversed-Phase HPLC was performed under the following conditions: Instrument, Waters®; Column, Waters Xterra C-18, 5 µm, 19×50 mm; Flow rate, 30 mL/min; Detection, λ=254 nm; Gradient, 5% to 100% acetonitrile/water (0.1% formic acid) over 8 min.

Analytical Reversed-Phase HPLC was performed under the following conditions: Instrument, Shimadzu; Column, Princeton SPHER HTS, 5 µm, 3×50 mm; Flow rate, 2.2 mL/min; Detection, Sedex 75 ELS coupled to Finnigan AQA electrospray mass spectrometer; Gradient, 0.1 to 100% acetonitrile/water (0.1% trifluoroacetic acid) over 8 min.

Unless otherwise specified, column chromatography was performed on silica gel, eluting with 2 M $NH_3$ in MeOH/DCM.

Mass spectra were obtained on a Finnigan AQA using electrospray ionization (ESI) in either positive or negative modes as indicated.

NMR spectra were obtained on either a Varian model VXR-300S (300 MHz) spectrometer. The format of the $^1$H NMR data below is: chemical shift in ppm down field of the tetramethylsilane reference (multiplicity, coupling constant J in Hz, integration).

Where solutions are "concentrated", they are concentrated on a rotary evaporator under reduced pressure.

Examples 1 through 17 describe the synthesis of intermediates used to prepare certain compounds of the invention.

Example 1

4-Phenylcarbamoyl-piperazine-1-carboxylic acid tert-butyl ester (intermediate)

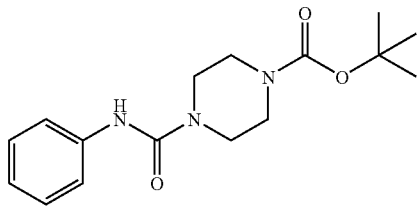 [SMILES: CC(C)(C)OC(=O)N1CCN(C(=O)Nc2ccccc2)CC1]

A solution of piperazine-1-carboxylic acid tert-butyl ester (114 g) in DCM (500 mL) was cooled in an ice bath and treated with phenyl isocyanate (65 mL). After 1 hour (h), the bath was removed. After 15 h, the resulting mixture was filtered and the solid was washed with dichloromethane (DCM, 2×100 mL), giving the title compound as a white amorphous solid (95 g).

Example 2

Piperazine-1-carboxylic acid phenylamide (intermediate)

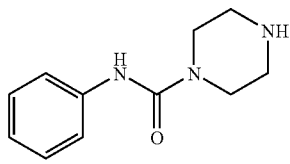 [SMILES: O=C(Nc1ccccc1)N1CCNCC1]

A solution of 4-phenylcarbamoyl-piperazine-1-carboxylic acid tert-butyl ester (50 g) in MeOH (1 L) was treated with 2 M HCl in Et$_2$O (164 mL). After 48 h, the resulting suspension was diluted with Et$_2$O (1 L) and filtered. The solid was washed with Et$_2$O (3×100 mL) and dried in vacuo, giving a white powder (32 g). This powder was partitioned between DCM (400 mL) and 10% aq. KOH (400 mL). The aqueous phase was extracted with DCM (2×400 mL). The organic phases were combined, dried (MgSO$_4$), and concentrated, giving the title compound as a white amorphous solid (26 g).

Example 3

4-(4-Fluoro-phenylcarbamoyl)-piperazine-1-carboxylic acid tert-butyl ester (intermediate)

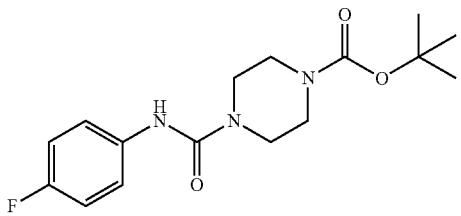 [SMILES: CC(C)(C)OC(=O)N1CCN(C(=O)Nc2ccc(F)cc2)CC1]

The title compound was prepared in analogy with Example 1, using 4-fluorophenyl isocyanate.

Example 4

Piperazine-1-carboxylic acid (4-fluoro-phenyl)-amide (intermediate)

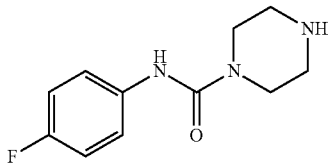 [SMILES: O=C(Nc1ccc(F)cc1)N1CCNCC1]

The title compound was prepared in analogy with Example 2, using 4-(4-fluoro-phenylcarbamoyl)-piperazine-1-carboxylic acid tert-butyl ester.

Example 5

4-(3,4-Dibromo-benzyl)-piperazine-1-carboxylic acid tert-butyl ester (intermediate)

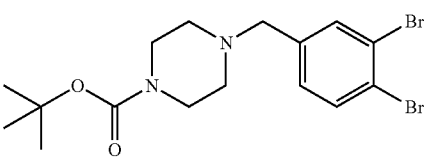 [SMILES: CC(C)(C)OC(=O)N1CCN(Cc2ccc(Br)c(Br)c2)CC1]

A solution of piperazine-1-carboxylic acid tert-butyl ester (3.5 g) and 3,4-dibromobenzaldehyde (5.0 g) in DCM (80 mL) was treated with NaB(OAc)$_3$H (5.6 g). After 16 h, the resulting mixture was treated with 10% aq. KOH (80 mL). The aqueous phase was extracted with DCM (1×80 mL). The organic extracts were combined and dried (MgSO$_4$). Most of the solvent was removed by concentration. Upon standing overnight, the resulting mixture produced crystals that were filtered and washed with DCM (1×5 mL), giving the title compound as a white crystalline solid (6.0 g).

Example 6

1-(3,4-Dibromo-benzyl)-piperazine (intermediate)

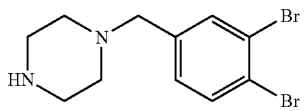 [SMILES: Brc1ccc(CN2CCNCC2)cc1Br]

A suspension of 4-(3,4-dibromo-benzyl)-piperazine-1-carboxylic acid tert-butyl ester (6.0 g) in MeOH (100 mL) was treated with 2 M HCl in $Et_2O$ (28 mL). After 16 h, the resulting suspension was diluted with $Et_2O$ (100 mL) and filtered. The solid was washed with $Et_2O$ (2×20 mL) and dried in vacuo, giving a white solid (5.0 g). This solid was partitioned between 10% aq. KOH (50 mL) and DCM (3×50 mL). The combined organic extracts were dried ($MgSO_4$) and concentrated to give the title compound as a colorless glassy oil.

Example 7

4-Quinolin-3-ylmethyl-piperazine-1-carboxylic acid tert-butyl ester (intermediate)

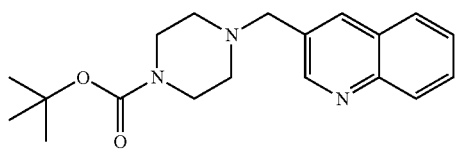 [SMILES: CC(C)(C)OC(=O)N1CCN(Cc2cnc3ccccc3c2)CC1]

The title compound was prepared in analogy with Example 5, using quinoline-3-carbaldehyde.

Example 8

3-Piperazin-1-ylmethyl-quinoline (intermediate)

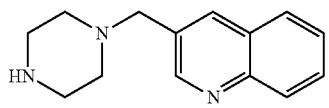 [SMILES: c1ccc2ncc(CN3CCNCC3)cc2c1]

The title compound was prepared in analogy with Example 6, using 4-Quinolin-3-ylmethyl-piperazine-1-carboxylic acid tert-butyl ester.

Example 9

4-(3-Hydroxy-benzyl)-piperazine-1-carboxylic acid phenylamide (intermediate)

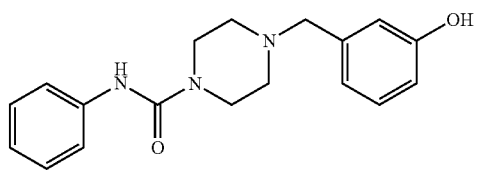 [SMILES: O=C(Nc1ccccc1)N1CCN(Cc2cccc(O)c2)CC1]

To a solution of piperazine-1-carboxylic acid phenylamide (2.0 g) and 3-hydroxybenzaldehyde (3.0 g) in DCM (200 mL) was added acetic acid (1.1 mL) followed by portion-wise addition of $NaB(OAc)_3H$ (6.0 g). The reaction mixture was stirred overnight. A solution of 10% aq. NaOH (30 mL) was added until the pH of the aqueous phase was 11. A solution of 1 N HCl was then added until the pH of the aqueous phase was 6-7. The aqueous phase was extracted with DCM (200 mL). The combined organic layers were dried ($MgSO_4$) and concentrated. Chromatography of the residue gave the title compound as a white solid (2.5 g).

Example 10

4-(4-Hydroxy-benzyl)-piperazine-1-carboxylic acid phenylamide (intermediate)

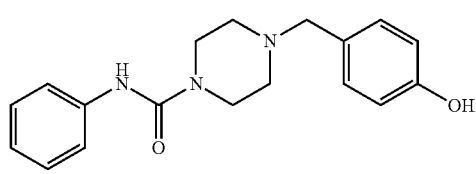 [SMILES: O=C(Nc1ccccc1)N1CCN(Cc2ccc(O)cc2)CC1]

The title compound was prepared in analogy to Example 9, using 4-hydroxybenzaldehyde.

Example 11

6-Chloro-quinoline-2-carbaldehyde (intermediate)

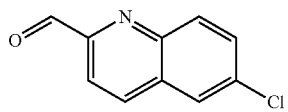 [SMILES: O=Cc1ccc2cc(Cl)ccc2n1]

A suspension of 6-chloro-2-methyl-quinoline (355 mg) and $SeO_2$ (233 mg) in 1,4-dioxane (3 mL) was heated at 80° C. for 16 h. The resulting black mixture was filtered through diatomaceous earth. Concentration of the filtrate gave the title compound as a yellow powder (324 mg).

Example 12

8-Chloro-quinoline-2-carbaldehyde (intermediate)

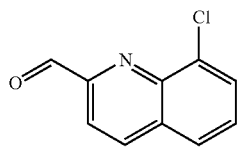 [SMILES: O=Cc1ccc2cccc(Cl)c2n1]

The title compound was prepared in analogy to Example 11, using 8-chloro-2-methyl-quinoline.

Example 13

1-Methyl-1H-indole-5-carbaldehyde (intermediate)

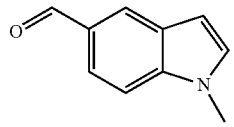

A solution of indole-5-carbaldehyde (0.5 g) in dimethyl carbonate (5 mL) was treated with 1,4-diaza-bicyclo[2.2.2]octane (38 mg). The resulting mixture was heated to 90° C. for 5 h and cooled to room temperature (rt). EtOAc (10 mL) and water (10 mL) were added, and the aqueous phase was extracted with EtOAc (3×10 mL). The combined organic extracts were washed with brine (1×20 mL), dried (MgSO$_4$), and concentrated. Chromatography of the residue (0-50% EtOAc-hexanes) gave the title compound as a white solid (46%).

Example 14

1-Methyl-1H-indole-6-carbaldehyde (intermediate)

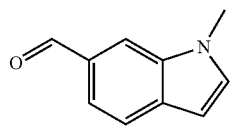

The title compound was prepared in analogy to Example 13, using indole-6-carboxaldehyde.

Example 15

Pyridin-2-yl-carbamic acid phenyl ester (intermediate)

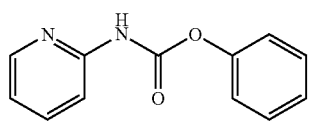 [SMILES: O=C(Nc1ccccn1)Oc1ccccc1]

To a solution of 2-aminopyridine (3.0 g) in dry THF (30 mL) was added phenyl chloroformate (1.0 g, 0.8 mL) dropwise at 0° C., followed by another batch of phenyl chloroformate (1.0 g, 0.8 mL). The reaction mixture was allowed to warm to rt. After 18 h, the mixture was diluted with EtOAc (100 mL) and washed with satd. aq. NaHCO$_3$ (20 mL). The organic layer was dried (MgSO$_4$) and concentrated. The residue was chromatographed to give a white solid (1.7 g).

Example 16

Pyridin-3-yl-carbamic acid phenyl ester (intermediate)

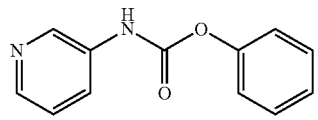 [SMILES: O=C(Nc1cccnc1)Oc1ccccc1]

The title compound was prepared in analogy with Example 15 using 3-aminopyridine.

Example 17

Pyridin-4-yl-carbamic acid phenyl ester (intermediate)

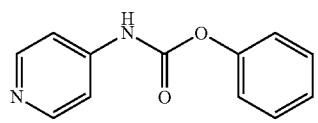 [SMILES: O=C(Nc1ccncc1)Oc1ccccc1]

The title compound was prepared in analogy with Example 15 using 4-aminopyridine.

Example 18

4-Naphthalen-2-ylmethyl-piperazine-1-carboxylic acid phenylamide

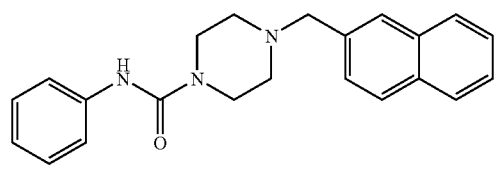 [SMILES: O=C(Nc1ccccc1)N1CCN(Cc2ccc3ccccc3c2)CC1]

A solution of piperazine-1-carboxylic acid phenylamide (103 mg) and 2-naphthaldehyde (94 mg) in DCM (2 mL) was treated with NaB(OAc)$_3$H (148 mg). After 16 h, the resulting mixture was treated with 10% aq. KOH (2 mL). The aqueous phase was extracted with DCM (2×3 mL). The combined extracts were dried (MgSO$_4$) and concentrated. Chromatography of the residue gave the title compound as a white foam (111 mg). $^1$H NMR (400 MHz, CDCl$_3$): 7.85-7.80 (m, 3H), 7.74 (s, 1H), 7.52-7.45 (m, 3H), 7.35-7.25 (m, 4H), 7.05-7.00 (m, 1H), 6.37 (br s, 1H), 3.69 (s, 2H), 3.53-3.48 (m, 4H), 2.55-2.49 (m, 4H).

Examples 19-84 were prepared from piperazine-1-carboxylic acid phenylamide and the specified carbonyl compounds in analogy with Example 18. Products were isolated either by filtration of the reaction mixture or by column chromatography.

Example 19

4-Quinolin-2-ylmethyl-piperazine-1-carboxylic acid phenylamide

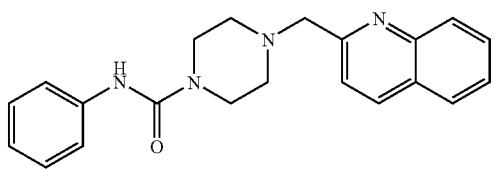

The title compound was prepared from 2-quinolinecarboxaldehyde. ¹H NMR (400 MHz, CDCl₃): 8.16 (d, J=8.4 Hz, 1H), 8.08 (d, J=8.4 Hz, 1H), 7.82 (d, J=8.1 Hz, 1H), 7.74-7.69 (m, 1H), 7.63 (d, J=8.6 Hz, 1H), 7.56-7.51 (m, 1H), 7.36-7.21 (m, 4H), 7.05-7.00 (m, 1H), 6.37 (br s, 1H), 3.89 (s, 2H), 3.55-3.53 (m, 4H), 2.63-2.58 (m, 4H).

Example 20

4-Benzo[b]thiophen-2-ylmethyl-piperazine-1-carboxylic acid phenylamide

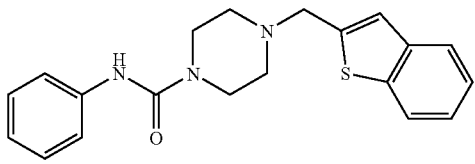

The title compound was prepared from benzo[b]thiophene-2-carbaldehyde. ¹H NMR (400 MHz, CDCl₃): 7.81-7.79 (m, 1H), 7.71-7.69 (m, 1H), 7.36-7.26 (m, 6H), 7.16 (s, 1H), 7.05-7.01 (m, 1H), 6.32 (s, 1H), 3.83-3.83 (m, 2H), 3.54-3.52 (m, 4H), 2.60-2.57 (m, 4H).

Example 21

4-(3,4-Dibromo-benzyl)-piperazine-1-carboxylic acid phenylamide

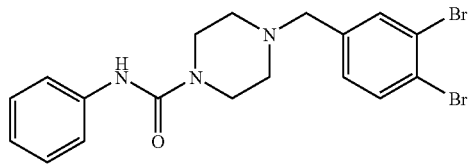 [SMILES: O=C(Nc1ccccc1)N1CCN(Cc2ccc(Br)c(Br)c2)CC1]

The title compound was prepared from 3,4-dibromobenzaldehyde. ¹H NMR (400 MHz, CDCl₃): 7.62 (d, J=1.8 Hz, 1H), 7.57 (d, J=8.1 Hz, 1H), 7.36-7.25 (m, 4H), 7.14 (dd, J=8.0, 2.0 Hz, 1H), 7.06-7.01 (m, 1H), 6.36 (br s, 1H), 3.52-3.48 (m, 4H), 3.45 (s, 2H), 2.48-2.44 (m, 4H).

Example 22

4-(1-Methyl-1H-indol-2-ylmethyl)-piperazine-1-carboxylic acid phenylamide

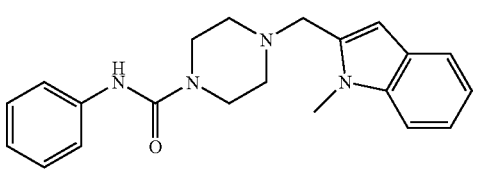

The title compound was prepared from 1-methyl-1H-indole-2-carbaldehyde. ¹H NMR (400 MHz, CDCl₃): 7.56 (d, J=7.6 Hz, 1H), 7.34-7.18 (m, 6H), 7.11-7.06 (m, 1H), 7.02-6.98 (m, 1H), 6.49 (br s, 1H), 6.36 (s, 1H), 3.78 (s, 3H), 3.63 (s, 2H), 3.44-3.39 (m, 4H), 2.47-2.42 (m, 4H).

Example 23

4-Quinolin-3-ylmethyl-piperazine-1-carboxylic acid phenylamide

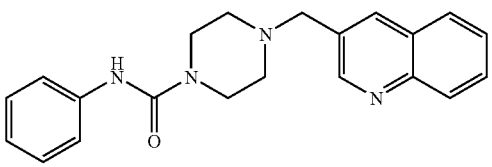

The title compound was prepared from 3-quinolinecarboxaldehyde. ¹H NMR (400 MHz, CDCl₃): 8.91 (d, J=2.0 Hz, 1H), 8.15-8.05 (m, 2H), 7.83-7.80 (m, 1H), 7.73-7.68 (m, 1H), 7.59-7.53 (m, 1H), 7.36-7.24 (m, 4H), 7.05-7.00 (m, 1H), 6.50 (br s, 1H), 3.72 (s, 2H), 3.53-3.28 (m, 4H), 2.55-2.50 (m, 4H).

Example 24

4-(4-Iodo-benzyl)-piperazine-1-carboxylic acid phenylamide

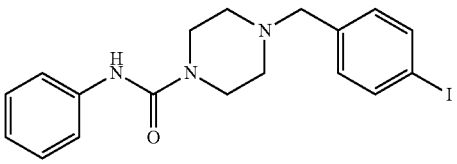 [SMILES: O=C(Nc1ccccc1)N1CCN(Cc2ccc(I)cc2)CC1]

The title compound was prepared from 4-iodobenzaldehyde. ¹H NMR (400 MHz, CDCl₃): 7.67-7.64 (m, 2H), 7.35-7.26 (m, 4H), 7.10-7.01 (m, 3H), 6.32 (s, 1H), 3.51-3.48 (m, 6H), 2.48-2.45 (m, 4H).

Example 25

4-(3-Benzyloxy-benzyl)-piperazine-1-carboxylic acid phenylamide

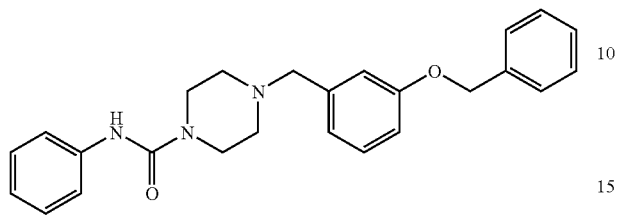

The title compound was prepared from 3-benzyloxybenzaldehyde. $^1$H NMR (400 MHz, CDCl$_3$): 7.45-7.22 (m, 10H), 7.05-6.88 (m, 4H), 6.31 (s, 1H), 5.08 (s, 2H), 3.51-3.47 (m, 6H), 2.48-2.46 (m, 4H).

Example 26

4-(5-Bromo-2-hydroxy-3-methoxy-benzyl)-piperazine-1-carboxylic acid phenylamide

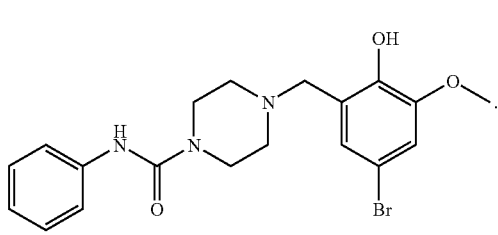 [SMILES: COc1cc(Br)cc(CN2CCN(C(=O)Nc3ccccc3)CC2)c1O]

The title compound was prepared from 5-bromo-2-hydroxy-3-methoxy-benzaldehyde. $^1$H NMR (400 MHz, CDCl$_3$): 10.7 (br s, 1H), 7.32-7.25 (7.35-7.25, m, 4H), 7.06-7.01 (m, 1H), 6.94 (d, J=2.0 Hz, 1H), 6.76 (d, J=2.0 Hz, 1H), 6.50 (br s, 1H), 3.86 (s, 3H), 3.70 (s, 2H), 3.56-3.50 (m, 4H), 2.60-2.55 (m, 4H).

Example 27

4-(4-Bromo-benzyl)-piperazine-1-carboxylic acid phenylamide

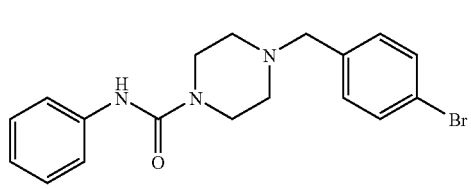 [SMILES: O=C(Nc1ccccc1)N1CCN(Cc2ccc(Br)cc2)CC1]

The title compound was prepared from 4-bromobenzaldehyde. $^1$H NMR (400 MHz, CDCl$_3$): 7.47-7.43 (m, 2H), 7.35-7.20 (m, 6H), 7.05-7.00 (m, 1H), 6.35 (s, 1H), 3.51-3.47 (m, 6H), 2.48-2.44 (m, 4H).

Example 28

4-(3-Phenoxy-benzyl)-piperazine-1-carboxylic acid phenylamide

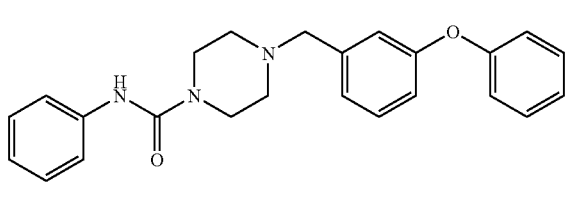 [SMILES: O=C(Nc1ccccc1)N1CCN(Cc2cccc(Oc3ccccc3)c2)CC1]

The title compound was prepared from 3-phenoxybenzaldehyde. $^1$H NMR (400 MHz, CDCl$_3$): 7.36-7.26 (m, 7H), 7.13-6.99 (m, 6H), 6.92-6.89 (m, 1H), 6.30 (s, 1H), 3.52-3.48 (m, 6H), 2.49-2.47 (m, 4H).

Example 29

4-(3-Bromo-4-fluoro-benzyl)-piperazine-1-carboxylic acid phenylamide

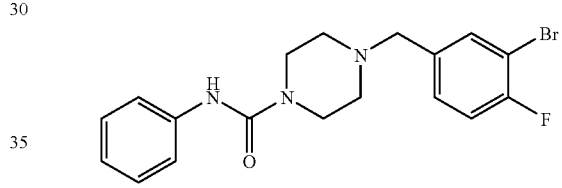

The title compound was prepared from 3-bromo-4-fluorobenzaldehyde. $^1$H NMR (400 MHz, CDCl$_3$): 7.55 (dd, J=6.6, 2.1 Hz, 1H), 7.35-7.21 (m, 5H), 7.07 (t, J=8.4 Hz, 1H), 7.05-7.00 (m, 1H), 6.43 (br s, 1H), 3.50-3.45 (m, 6H), 2.47-2.42 (m, 4H).

Example 30

4-Indan-5-ylmethyl-piperazine-1-carboxylic acid phenylamide

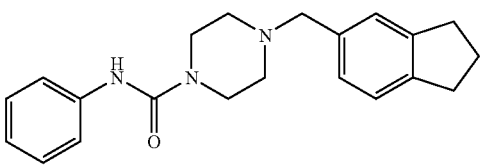

The title compound was prepared from indan-5-carbaldehyde. $^1$H NMR (400 MHz, CDCl$_3$): 7.35-7.00 (m, 8H), 6.30 (s, 1H), 3.51-3.47 (m, 6H), 2.92-2.88 (m, 4H), 2.50-2.47 (m, 4H), 2.12-2.04 (m, 2H).

Example 31

4-Benzo[b]thiophen-3-ylmethyl-piperazine-1-carboxylic acid phenylamide

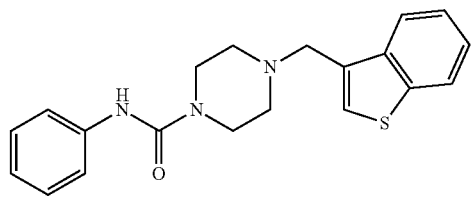 [SMILES: O=C(Nc1ccccc1)N1CCN(Cc2csc3ccccc23)CC1]

The title compound was prepared from benzo[b]thiophene-3-carbaldehyde. $^1$H NMR (400 MHz, CDCl$_3$): 8.00-7.98 (m, 1H), 7.88-7.85 (m, 1H), 7.42-7.28 (m, 7H), 7.05-7.01 (m, 1H), 6.32 (s, 1H), 3.78 (d, J=0.8 Hz, 2H), 3.51-3.49 (m, 4H), 2.56-2.53 (m, 4H).

Example 32

4-(4-Isopropyl-benzyl)-piperazine-1-carboxylic acid phenylamide

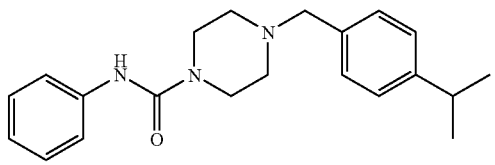 [SMILES: CC(C)c1ccc(CN2CCN(C(=O)Nc3ccccc3)CC2)cc1]

The title compound was prepared from 4-isopropylbenzaldehyde. $^1$H NMR (400 MHz, CDCl$_3$): 7.35-7.18 (m, 8H), 7.05-7.01 (m, 1H), 6.30 (s, 1H), 3.50-3.49 (m, 6H), 2.94-2.87 (m, 1H), 2.50-2.47 (m, 4H), 1.25 (d, J=6.9 Hz, 6H).

Example 33

4-(4-Ethyl-benzyl)-piperazine-1-carboxylic acid phenylamide

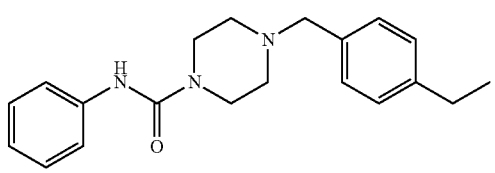 [SMILES: CCc1ccc(CN2CCN(C(=O)Nc3ccccc3)CC2)cc1]

The title compound was prepared from 4-ethylbenzaldehyde. $^1$H NMR (400 MHz, CDCl$_3$): 7.35-7.00 (m, 9H), 6.32 (s, 1H), 3.62-3.48 (m, 6H), 2.68-2.62 (m, 2H), 2.49-2.47 (m, 4H), 1.26-1.22 (m, 3H).

Example 34

4-(5-Bromo-2-hydroxy-benzyl)-piperazine-1-carboxylic acid phenylamide

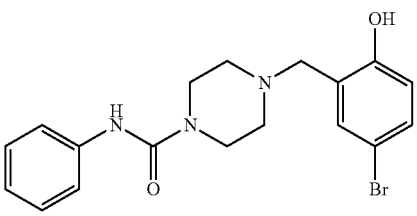 [SMILES: O=C(Nc1ccccc1)N1CCN(Cc2cc(Br)ccc2O)CC1]

The title compound was prepared from 5-bromo-2-hydroxy-benzaldehyde. $^1$H NMR (400 MHz, CDCl$_3$): 10.54 (br s, 1H), 7.35-7.25 (m, 5H), 7.12-7.02 (m, 2H), 6.73 (d, J=8.6 Hz, 1H), 6.42 (br s, 1H), 3.70 (s, 2H), 3.55 (br s, 4H), 2.58 (br s, 4H).

Example 35

4-(2,3-Dihydro-benzo[1,4]dioxin-6-ylmethyl)-piperazine-1-carboxylic acid phenylamide

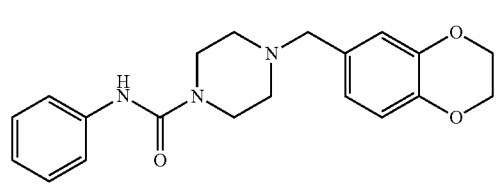 [SMILES: O=C(Nc1ccccc1)N1CCN(Cc2ccc3c(c2)OCCO3)CC1]

The title compound was prepared from 2,3-dihydro-benzo[1,4]dioxine-6-carbaldehyde. $^1$H NMR (400 MHz, CDCl$_3$): 7.36-7.25 (m, 4H), 7.05-7.00 (m, 1H), 6.85-6.76 (m, 3H), 6.33 (br s, 1H), 4.26 (s, 4H), 3.51-3.46 (m, 4H), 3.42 (s, 2H), 2.49-2.45 (m, 4H).

Example 36

4-(4-Methoxy-benzyl)-piperazine-1-carboxylic acid phenylamide

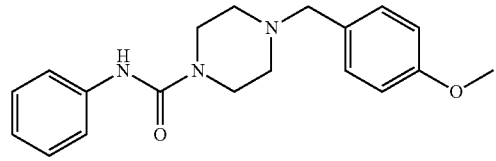 [SMILES: COc1ccc(CN2CCN(C(=O)Nc3ccccc3)CC2)cc1]

The title compound was prepared from 4-methoxybenzaldehyde. $^1$H NMR (400 MHz, CDCl$_3$): 7.35-7.21 (m, 6H), 7.04-6.99 (m, 1H), 6.89-6.84 (m, 2H), 6.43 (br s, 1H), 3.80 (s, 3H), 3.50-3.45 (m, 6H), 2.46-2.42 (m, 4H).

Example 37

4-(3-Vinyl-benzyl)-piperazine-1-carboxylic acid phenylamide

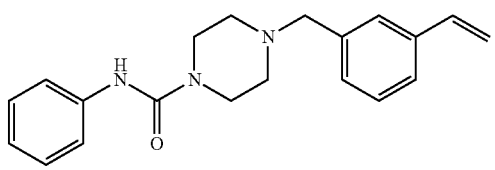 [SMILES: C=Cc1cccc(CN2CCN(C(=O)Nc3ccccc3)CC2)c1]

The title compound was prepared from 3-vinylbenzaldehyde. $^1$H NMR (400 MHz, CDCl$_3$): 7.36-7.23 (m, 7H), 7.21-6.99 (m, 1H), 6.76-6.69 (m, 1H), 6.49 (s, 1H), 5.79-5.74 (m, 1H), 5.27-5.24 (m, 1H), 3.52-3.45 (m, 6H), 2.47-2.45 (m, 4H).

Example 38

4-(2,3-Dihydro-benzofuran-5-ylmethyl)-piperazine-1-carboxylic acid phenylamide

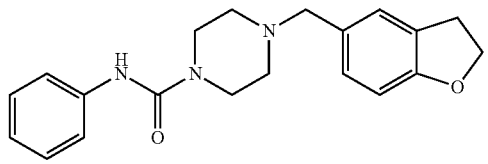 [SMILES: O=C(Nc1ccccc1)N1CCN(Cc2ccc3c(c2)CCO3)CC1]

The title compound was prepared from 2,3-dihydro-benzofuran-5-carbaldehyde. $^1$H NMR (400 MHz, CDCl$_3$): 7.36-7.28 (m, 4H), 7.17 (s, 1H), 7.06-7.01 (m, 1H), 6.73 (d, J=8.1 Hz, 1H), 6.30 (s, 1H), 4.60-4.55 (m, 2H), 3.51-3.46 (m, 6H), 3.23-3.19 (m, 2H), 2.49-2.47 (m, 4H).

Example 39

4-(3-Methoxy-benzyl)-piperazine-1-carboxylic acid phenylamide

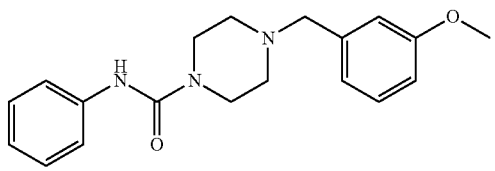 [SMILES: COc1cccc(CN2CCN(C(=O)Nc3ccccc3)CC2)c1]

The title compound was prepared from 3-methoxybenzaldehyde. $^1$H NMR (400 MHz, CDCl$_3$): 7.35-7.32 (m, 2H), 7.28-7.22 (m, 3H), 7.03-6.98 (m, 1H), 6.92-6.89 (m, 2H), 6.83-6.79 (m, 1H), 6.49 (br s, 1H), 3.81 (s, 3H), 3.50-3.45 (m, 6H), 2.47-2.43 (m, 4H).

Example 40

4-Naphthalen-1-ylmethyl-piperazine-1-carboxylic acid phenylamide

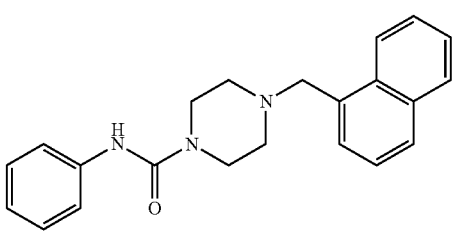 [SMILES: O=C(Nc1ccccc1)N1CCN(Cc2cccc3ccccc23)CC1]

The title compound was prepared from 1-naphthalenecarboxaldehyde. $^1$H NMR (400 MHz, CDCl$_3$): 8.31-8.27 (m, 1H), 7.88-7.77 (m, 2H), 7.55-7.47 (m, 2H), 7.43-7.24 (m, 6H), 7.04-6.99 (m, 1H), 6.37 (br s, 1H), 3.93 (s, 2H), 3.49-3.44 (m, 4H), 2.55-2.51 (m, 4H).

Example 41

4-(2-Hydroxy-benzyl)-piperazine-1-carboxylic acid phenylamide

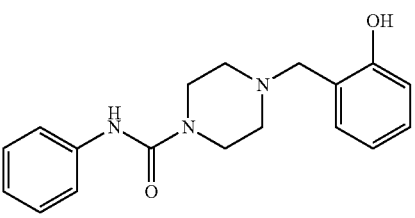 [SMILES: O=C(Nc1ccccc1)N1CCN(Cc2ccccc2O)CC1]

The title compound was prepared from 2-hydroxybenzaldehyde. $^1$H NMR (400 MHz, CDCl$_3$): 10.42 (br s, 1H), 7.36-7.17 (m, 5H), 7.07-6.97 (m, 2H), 6.88-6.77 (m, 2H), 6.50 (br s, 1H), 3.73 (s, 2H), 3.53 (br s, 4H), 2.57 (br s, 4H).

Example 42

4-(3-Methyl-benzyl)-piperazine-1-carboxylic acid phenylamide

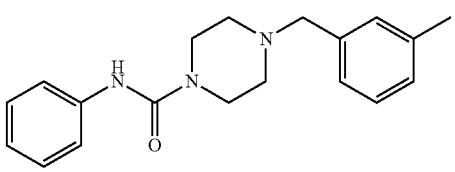 [SMILES: Cc1cccc(CN2CCN(C(=O)Nc3ccccc3)CC2)c1]

The title compound was prepared from 3-methylbenzaldehyde. $^1$H NMR (400 MHz, CDCl$_3$): 7.35-7.00 (m, 9H), 6.34 (s, 1H), 3.51-3.49 (m, 6H), 2.49-2.47 (m, 4H), 2.36 (s, 3H).

Example 43

4-(1H-Indol-5-ylmethyl)-piperazine-1-carboxylic acid phenylamide

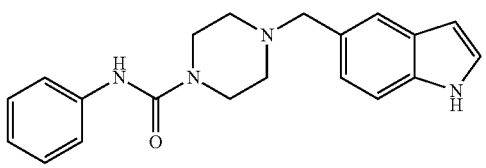 [SMILES: O=C(Nc1ccccc1)N1CCN(Cc2ccc3[nH]ccc3c2)CC1]

The title compound was prepared from 5-indolecarboxaldehyde. $^1$H NMR (400 MHz, CDCl$_3$): 7.55 (br s, 1H), 7.40-7.20 (m, 6H), 7.15 (dd, J=8.2 Hz, 1.6, 1H), 7.05-6.99 (m, 1H), 6.50 (dd, J=3.0, 0.9 Hz, 1H), 3.65 (m, 2H), 3.53-3.47 (m, 4H), 2.55-2.50 (m, 4H).

Example 44

4-(3,4-Dimethoxy-benzyl)-piperazine-1-carboxylic acid phenylamide

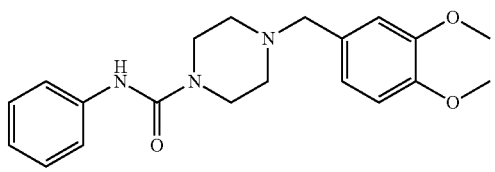 [SMILES: COc1ccc(CN2CCN(C(=O)Nc3ccccc3)CC2)cc1OC]

The title compound was prepared from 3,4-dimethoxybenzaldehyde. $^1$H NMR (400 MHz, CDCl$_3$): 7.36-7.32 (m, 2H), 7.28-7.23 (m, 2H), 7.04-6.98 (m, 1H), 6.90-6.80 (m, 3H), 6.53 (br s, 1H), 3.89 (s, 3H), 3.87 (s, 3H), 3.50-3.45 (m, 6H), 2.46-2.42 (m, 4H).

Example 45

4-Pyridin-4-ylmethyl-piperazine-1-carboxylic acid phenylamide

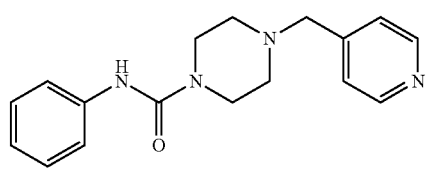 [SMILES: O=C(Nc1ccccc1)N1CCN(Cc2ccncc2)CC1]

The title compound was prepared from 4-pyridinecarboxaldehyde. $^1$H NMR (400 MHz, CDCl$_3$): 8.57-8.56 (m, 2H), 7.36-7.27 (m, 6H), 7.06-7.02 (m, 1H), 6.34 (s, 1H), 3.55-3.51 (m, 6H), 2.51-2.49 (m, 4H).

Example 46

4-Pyridin-2-ylmethyl-piperazine-1-carboxylic acid phenylamide

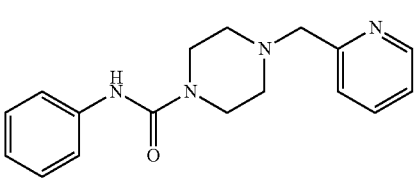 [SMILES: O=C(Nc1ccccc1)N1CCN(Cc2ccccn2)CC1]

The title compound was prepared from 2-pyridinecarboxaldehyde. $^1$H NMR (400 MHz, CDCl$_3$): 8.60-8.58 (m, 1H), 7.70-7.52 (m, 1H), 7.42-7.18 (m, 6H), 7.05-7.00 (m, 1H), 6.32 (s, 1H), 3.71 (s, 2H), 3.55-3.53 (m, 4H), 2.58-2.55 (m, 4H).

Example 47

4-Pyridin-3-ylmethyl-piperazine-1-carboxylic acid phenylamide

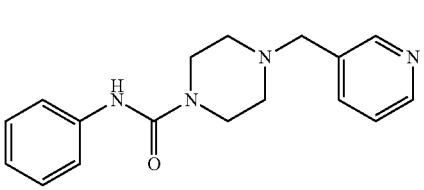 [SMILES: O=C(Nc1ccccc1)N1CCN(Cc2cccnc2)CC1]

The title compound was prepared from 3-pyridinecarboxaldehyde. $^1$H NMR (400 MHz, CDCl$_3$): 8.56-8.53 (m, 2H), 7.70-7.67 (m, 1H), 7.36-7.26 (m, 5H), 7.06-7.01 (m, 1H), 6.33 (s, 1H), 3.56 (s, 2H), 3.52-3.50 (m, 4H), 2.51-2.49 (m, 4H).

Example 48

4-(4-Isopropoxy-benzyl)-piperazine-1-carboxylic acid phenylamide

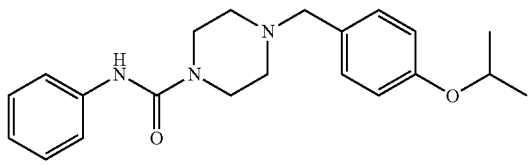 [SMILES: CC(C)Oc1ccc(CN2CCN(C(=O)Nc3ccccc3)CC2)cc1]

The title compound was prepared from 4-isopropoxybenzaldehyde. $^1$H NMR (400 MHz, CDCl$_3$): 7.35-7.20 (m, 7H), 7.05-7.00 (m, 1H), 6.86-6.83 (m, 1H), 6.32 (br m, 1H), 4.57-4.50 (m, 1H), 3.51-3.47 (m, 6H), 2.50-2.45 (m, 4H), 1.34 (d, J=6.0 Hz, 6H).

Example 49

4-Biphenyl-4-ylmethyl-piperazine-1-carboxylic acid phenylamide

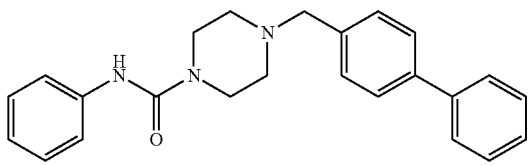 [SMILES: O=C(Nc1ccccc1)N1CCN(Cc2ccc(-c3ccccc3)cc2)CC1]

The title compound was prepared from 4-phenylbenzaldehyde. $^1$H NMR (400 MHz, CDCl$_3$): 7.61-7.55 (m, 4H), 7.46-7.25 (m, 9H), 7.05-7.00 (m, 1H), 6.44 (br s, 1H), 3.59 (s, 2H), 3.54-3.49 (m, 4H), 2.55-2.50 (m, 4H).

Example 50

4-Quinolin-4-ylmethyl-piperazine-1-carboxylic acid phenylamide

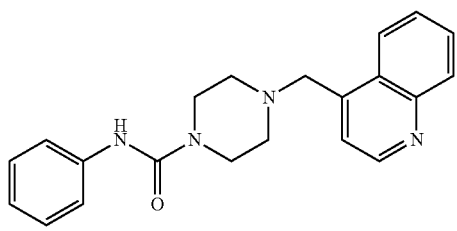 [SMILES: O=C(Nc1ccccc1)N1CCN(Cc2ccnc3ccccc23)CC1]

The title compound was prepared from 4-quinolinecarboxaldehyde. $^1$H NMR (400 MHz, CDCl$_3$): 8.87 (d, J=4.3 Hz, 1H), 8.24 (d, J=8.4 Hz, 1H), 8.14 (d, J=8.5 Hz, 1H), 7.75-7.70 (m, 1H), 7.61-7.55 (m, 1H), 7.43 (d, J=4.3 Hz, 1H), 7.36-7.25 (m, 4H), 7.05-7.00 (m, 1H), 6.44 (br s, 1H), 3.55-3.50 (m, 4H), 2.60-2.55 (m, 4H).

Example 51

4-Benzo[1,3]dioxol-4-ylmethyl-piperazine-1-carboxylic acid phenylamide

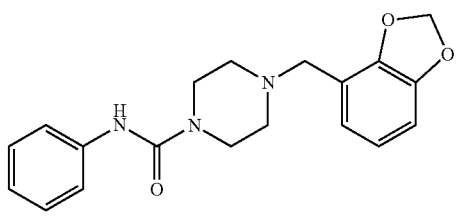 [SMILES: O=C(Nc1ccccc1)N1CCN(Cc2cccc3c2OCO3)CC1]

The title compound was prepared from benzo[1,3]dioxole-4-carbaldehyde. $^1$H NMR (400 MHz, CDCl$_3$): 7.36-7.25 (m, 4H), 7.06-7.00 (m, 1H), 6.85-6.75 (m, 3H), 6.30 (s, 1H), 3.57 (s, 2H), 3.54-3.49 (m, 4H), 2.56-2.50 (m, 4H).

Example 52

4-(2,2-Difluoro-benzo[1,3]dioxol-5-ylmethyl)-piperazine-1-carboxylic acid phenylamide

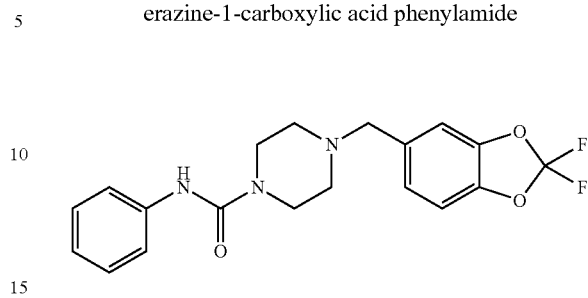

The title compound was prepared from 2,2-difluoro-benzo[1,3]dioxole-5-carbaldehyde. $^1$H NMR (400 MHz, CDCl$_3$): 7.37-7.25 (m, 4H), 7.12 (s, 1H), 7.06-6.98 (m, 3H), 6.32 (s, 1H), 3.54-3.46 (m, 6H), 2.50-2.45 (m, 4H).

Example 53

4-(1-Methyl-1H-indol-5-ylmethyl)-piperazine-1-carboxylic acid phenylamide

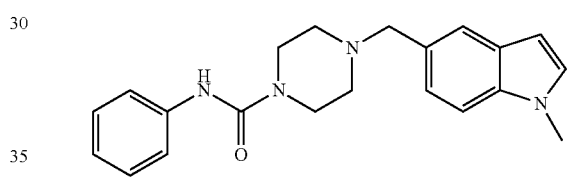

The title compound was prepared from 1-methyl-1H-indole-5-carbaldehyde. $^1$H NMR (400 MHz, CDCl$_3$): 7.55 (s, 1H), 7.36-7.25 (m, 5H), 7.21 (dd, J=8.4, 1.6 Hz, 1H), 7.06-7.00 (m, 2H), 6.46 (dd, J=3.0, 0.8 Hz, 1H), 6.29 (br s, 1H), 3.80 (s, 3H), 3.65 (s, 2H), 3.50 (t, J=5.1 Hz, 4H), 2.51 (t, J=5.1 hz, 4H).

Example 54

4-(6-Chloro-quinolin-2-ylmethyl)-piperazine-1-carboxylic acid phenylamide

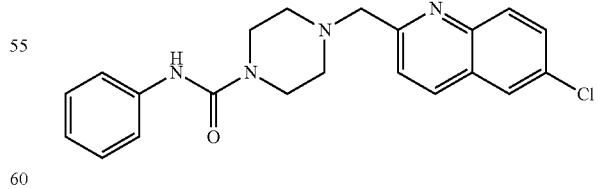

The title compound was prepared from 6-chloro-quinoline-2-carbaldehyde. $^1$H NMR (400 MHz, CDCl$_3$): 8.07 (d, J=8.4 Hz, 1H), 8.01 (d, J=8.8 Hz, 1H), 7.80 (d, J=2.2 Hz, 1H), 7.67-7.62 (m, 2H), 7.36-7.26 (m, 4H), 7.05-7.00 (m, 1H), 6.38 (s, 1H), 3.86 (s, 2H), 3.54 (t, J=5.1 Hz, 4H), 2.60 (t, J=5.1 Hz, 4H).

Example 55

4-(8-Chloro-quinolin-2-ylmethyl)-piperazine-1-carboxylic acid phenylamide

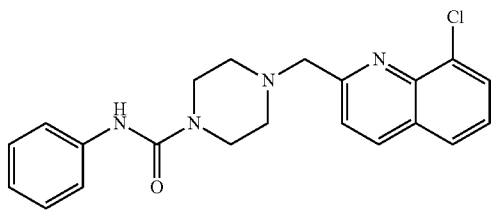 [SMILES: O=C(Nc1ccccc1)N1CCN(Cc2ccc3cccc(Cl)c3n2)CC1]

The title compound was prepared from 8-chloro-quinoline-2-carbaldehyde. ¹H NMR (400 MHz, CDCl₃): 8.17 (d, J=8.4 Hz, 1H), 7.82 (dd, J=7.5, 1.3 Hz, 1H), 7.75, 7.71 (m, 2H), 7.44 (t, J=7.7 Hz, 1H), 7.37-7.34 (m, 2H), 7.30-7.25 (m, 2H), 7.05-7.00 (m, 1H), 6.40 (s, 1H), 3.97 (s, 2H), 3.55 (t, J=5.1 Hz, 4H), 2.64 (t, J=5.1 Hz, 4H).

Example 56

4-(2-Chloro-quinolin-3-ylmethyl)-piperazine-1-carboxylic acid phenylamide

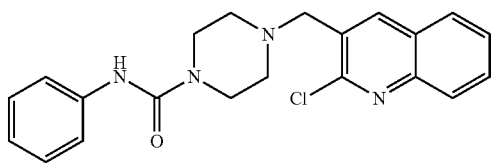 [SMILES: O=C(Nc1ccccc1)N1CCN(Cc2cc3ccccc3nc2Cl)CC1]

The title compound was prepared from 2-chloro-quinoline-3-carbaldehyde. ¹H NMR (400 MHz, CDCl₃): 8.23 (s, 1H), 8.02 (d, J=8.1 Hz, 1H), 7.84 (d, J=8.3 Hz, 1H), 7.75-7.70 (m, 1H), 7.60-7.55 (m, 1H), 7.37-7.25 (m, 4H), 7.05-7.00 (m, 1H), 6.42 (s, 1H), 3.79 (s, 2H), 3.56 (t, J=5.0 Hz, 4H), 2.63 (t, J=5.1 Hz, 4H).

Example 57

4-Naphthalen-2-ylmethyl-piperazine-1-carboxylic acid (4-fluoro-phenyl)-amide

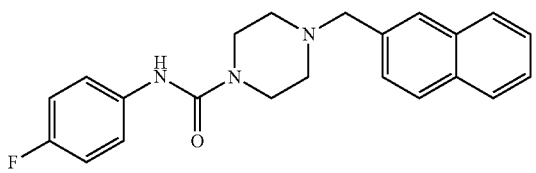

The title compound was prepared from piperazine-1-carboxylic acid (4-fluoro-phenyl)-amide and 2-naphthalenecarbaldehyde. ¹H NMR (400 MHz, CDCl₃): 7.85-7.80 (m, 3H), 7.74 (s, 1H), 7.52-7.45 (m, 3H), 7.30-7.25 (m, 2H), 6.98-6.92 (m, 2H), 6.36 (s, 1H), 3.69 (s, 2H), 3.49 (t, J=5.1 Hz, 4H), 2.51 (t, J=5.1 Hz, 4H).

Example 58

4-Quinolin-2-ylmethyl-piperazine-1-carboxylic acid (4-fluoro-phenyl)-amide

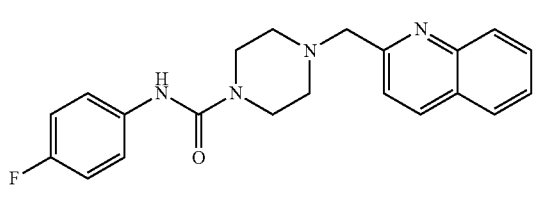 [SMILES: O=C(Nc1ccc(F)cc1)N1CCN(Cc2ccc3ccccc3n2)CC1]

The title compound was prepared from piperazine-1-carboxylic acid (4-fluoro-phenyl)-amide and 2-quinolinecarbaldehyde. ¹H NMR (400 MHz, CDCl₃): 8.16 (d, J=8.3 Hz, 1H), 8.08 (d, J=8.6 Hz, 1H), 7.82 (d, J=7.6 Hz, 1H), 7.74-6.69 (m, 1H), 7.63 (d, J=8.3 Hz, 1H), 7.56-7.52 (m, 1H), 7.32-7.25 (m, 2H), 6.99-6.94 (m, 2H), 6.38 (s, 1H), 3.88 (s, 2H), 3.52 (t, J=5.1 Hz, 4H), 2.60 (t, J=5.1 Hz, 4H).

Example 59

4-(1-Hydroxy-naphthalen-2-ylmethyl)-piperazine-1-carboxylic acid phenylamide

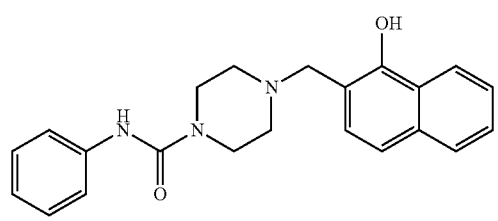 [SMILES: O=C(Nc1ccccc1)N1CCN(Cc2ccc3ccccc3c2O)CC1]

The title compound was prepared from 1-hydroxy-naphthalene-2-carbaldehyde. ¹H NMR (400 MHz, CDCl₃): 8.26-8.22 (m, 1H), 7.78-7.74 (m, 1H), 7.49-7.45 (m, 2H), 7.35-7.26 (m, 5H), 7.10-7.01 (m, 2H), 6.42 (s, 1H), 3.89 (s, 2H), 3.70-3.40 (br s, 4H), 2.80-2.50 (br s, 4H).

Example 60

4-[3-(4-Chloro-phenoxy)-benzyl]-piperazine-1-carboxylic acid phenylamide

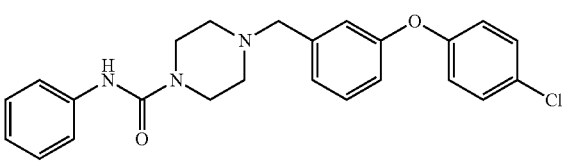 [SMILES: O=C(Nc1ccccc1)N1CCN(Cc2cccc(Oc3ccc(Cl)cc3)c2)CC1]

The title compound was prepared from 3-(4-chloro-phenoxy)-benzaldehyde. ¹H NMR (400 MHz, CDCl₃): 7.36-7.25 (m, 7H), 7.11-6.87 (m, 6H), 6.31 (s, 1H), 3.55-3.47 (m, 6H), 2.51-2.46 (m, 4H).

Example 61

4-[3-(3,4-Dichloro-phenoxy)-benzyl]-piperazine-1-carboxylic acid phenylamide

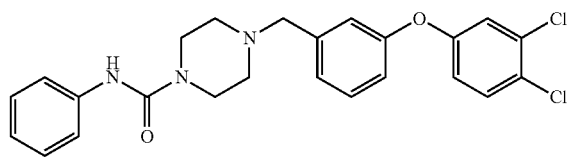 [SMILES: O=C(Nc1ccccc1)N1CCN(Cc2cccc(Oc3ccc(Cl)c(Cl)c3)c2)CC1]

The title compound was prepared from 3-(3,4-dichloro-phenoxy)-benzaldehyde. $^1$H NMR (400 MHz, CDCl$_3$): 7.40-7.25 (m, 6H), 7.15-7.00 (m, 4H), 6.94-6.84 (m, 2H), 6.29 (s, 1H), 3.56-3.48 (m, 6H), 2.52-2.47 (m, 10H).

Example 62

4-(3-p-Tolyloxy-benzyl)-piperazine-1-carboxylic acid phenylamide

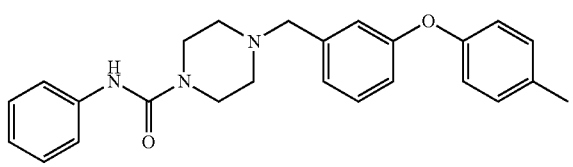 [SMILES: Cc1ccc(Oc2cccc(CN3CCN(C(=O)Nc4ccccc4)CC3)c2)cc1]

The title compound was prepared from 3-p-tolyloxy-benzaldehyde. $^1$H NMR (400 MHz, CDCl$_3$): 7.36-7.24 (m, 5H), 7.16-7.12 (m, 2H), 7.06-6.98 (m, 3H), 6.94-6.85 (m, 3H), 6.31 (s, 1H), 3.53-3.46 (m, 6H), 2.51-2.45 (m, 4H).

Example 63

4-[3-(4-tert-Butyl-phenoxy)-benzyl]-piperazine-1-carboxylic acid phenylamide

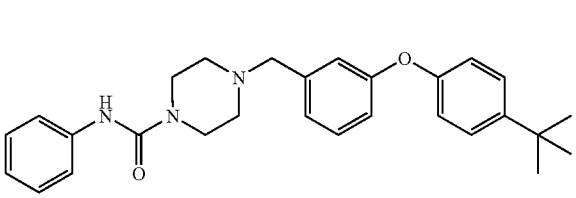 [SMILES: CC(C)(C)c1ccc(Oc2cccc(CN3CCN(C(=O)Nc4ccccc4)CC3)c2)cc1]

The title compound was prepared from 3-(4-tert-butyl-phenoxy)-benzaldehyde. $^1$H NMR (400 MHz, CDCl$_3$): 7.37-7.24 (m, 7H), 7.09-7.00 (m, 3H), 6.96-6.85 (m, 3H), 6.31 (s, 1H), 3.55-3.45 (m, 6H), 2.53-2.45 (m, 4H), 1.33 (s, 9H).

Example 64

4-[3-(3-Trifluoromethyl-phenoxy)-benzyl]-piperazine-1-carboxylic acid phenylamide

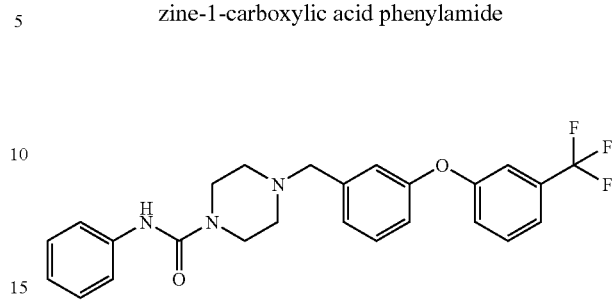

The title compound was prepared from 3-(3-trifluoromethyl-phenoxy)-benzaldehyde. $^1$H NMR (400 MHz, CDCl$_3$): 7.50-6.90 (m, 13H), 6.31 (s, 1H), 3.56-3.46 (m, 6H), 2.53-2.45 (m, 4H).

Example 65

4-[3-(4-Methoxy-phenoxy)-benzyl]-piperazine-1-carboxylic acid phenylamide

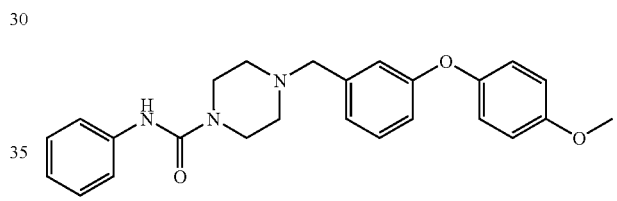

The title compound was prepared from 3-(4-methoxy-phenoxy)-benzaldehyde. $^1$H NMR (400 MHz, CDCl$_3$): 7.36-7.21 (m, 6H), 7.06-6.80 (m, 7H), 6.30 (s, 1H), 3.81 (s, 3H), 3.52-3.45 (m, 6H), 2.51-2.45 (m, 4H).

Example 66

4-(6-Methoxy-naphthalen-2-ylmethyl)-piperazine-1-carboxylic acid phenylamide

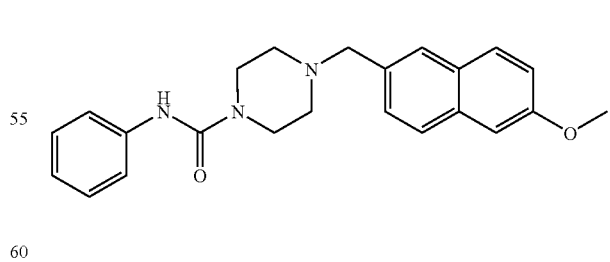

The title compound was prepared from 6-methoxy-naphthalene-2-carbaldehyde. $^1$H NMR (400 MHz, CDCl$_3$): 7.72 (d, J=8.3 Hz, 2H), 7.66 (s, 1H), 7.45 (dd, J=8.4, 1.6 Hz, 1H), 7.35-7.24 (m, 4H), 7.17-7.13 (m, 2H), 7.05-6.99 (m, 1H), 6.37 (s, 1H), 3.92 (s, 3H), 3.65 (s, 2H), 3.50 (t, J=5.1 Hz, 4H), 2.50 (t, J=5.1 Hz, 4H).

Example 67

4-Phenanthren-9-ylmethyl-piperazine-1-carboxylic acid phenylamide

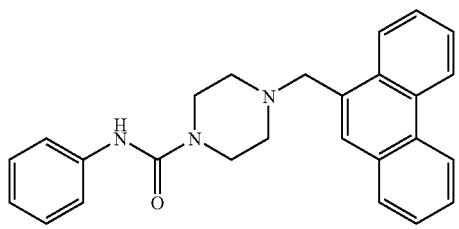 [SMILES: O=C(Nc1ccccc1)N1CCN(Cc2cc3ccccc3c3ccccc23)CC1]

The title compound was prepared from phenanthrene-9-carbaldehyde. $^1$H NMR (400 MHz, CDCl$_3$): 8.75-8.66 (m, 2H), 8.41-8.38 (m, 1H), 7.87 (dd, J=7.7, 1.3 Hz, 1H), 7.70-7.57 (m, 5H), 7.36-7.26 (m, 4H), 7.05-7.00 (m, 1H), 6.30 (s, 1H), 3.98 (s, 2H), 3.50 (t, J=5.1 Hz, 4H), 2.61 (t, J=5.1 Hz, 4H).

Example 68

4-Pyren-1-ylmethyl-piperazine-1-carboxylic acid phenylamide

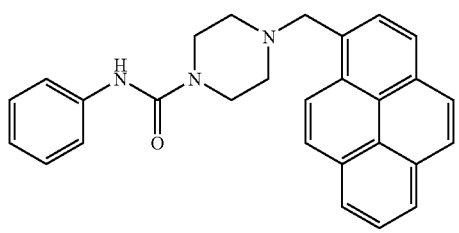 [SMILES: O=C(Nc1ccccc1)N1CCN(Cc2ccc3ccc4cccc5ccc2c3c45)CC1]

The title compound was prepared from pyrene-1-carbaldehyde. $^1$H NMR (400 MHz, CDCl$_3$): 8.53 (d, J=9.1 Hz, 1H), 8.22-8.12 (m, 4H), 8.06 (s, 2H), 8.04-7.96 (m, 2H), 7.36-7.25 (m, 4H), 7.05-7.00 (m, 1H), 6.30 (s, 1H), 4.22 (s, 2H), 3.50 (t, J=5.1 Hz, 4H), 2.62 (t, J=5.1 Hz, 4H).

Example 69

4-(6-Chloro-quinolin-3-ylmethyl)-piperazine-1-carboxylic acid phenylamide

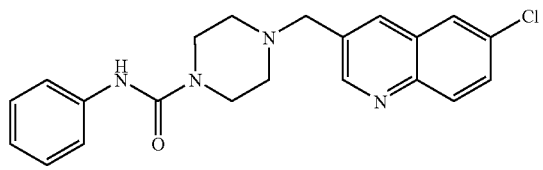 [SMILES: O=C(Nc1ccccc1)N1CCN(Cc2cnc3ccc(Cl)cc3c2)CC1]

The title compound was prepared from 6-chloro-quinoline-3-carbaldehyde. $^1$H NMR (400 MHz, CDCl$_3$): 8.13 (d, J=8.6 Hz, 1H), 8.09 (d, J=2.0 Hz, 1H), 7.75 (d, J=8.4 Hz, 1H), 7.63 (d, J=8.4 Hz, 1H), 7.49 (dd, J=8.4, 2.0 Hz, 1H), 7.36-7.26 (m, 4H), 7.05-7.00 (m, 1H), 6.35 (s, 1H), 3.87 (s, 2H), 3.55 (d, J=5.1 Hz, 4H), 2.61 (d, J=5.1 Hz, 4H).

Example 70

4-Biphenyl-3-ylmethyl-piperazine-1-carboxylic acid phenylamide

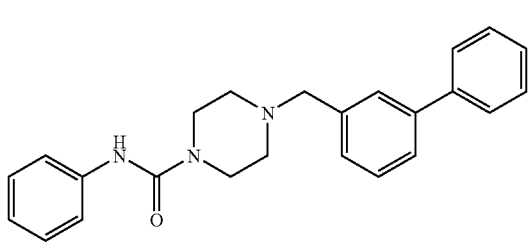 [SMILES: O=C(Nc1ccccc1)N1CCN(Cc2cccc(-c3ccccc3)c2)CC1]

The title compound was prepared from biphenyl-3-carbaldehyde. $^1$H NMR (400 MHz, CDCl$_3$): 7.65-7.25 (m, 13H), 7.06-7.00 (m, 1H), 6.31 (s, 1H), 3.61 (s, 2H), 3.55-3.49 (m, 4H), 2.58-2.50 (m, 4H).

Example 71

4-(6-Bromo-pyridin-2-ylmethyl)-piperazine-1-carboxylic acid phenylamide

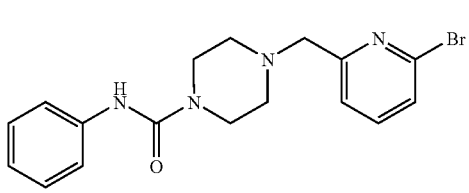 [SMILES: O=C(Nc1ccccc1)N1CCN(Cc2cccc(Br)n2)CC1]

The title compound was prepared from 6-bromo-pyridine-2-carbaldehyde. $^1$H NMR (400 MHz, CDCl$_3$): 7.57-7.26 (m, 7H), 7.06-7.01 (m, 1H), 6.32 (s, 1H), 3.70 (s, 2H), 3.54 (t, J=5.1 Hz, 4H), 2.57 (t, J=5.1 Hz, 4H).

Example 72

4-[3-(4-Chloro-benzenesulfonyl)-benzyl]-piperazine-1-carboxylic acid phenylamide

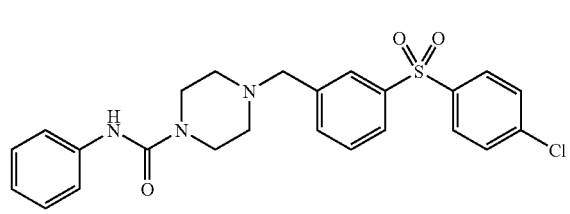 [SMILES: O=C(Nc1ccccc1)N1CCN(Cc2cccc(S(=O)(=O)c3ccc(Cl)cc3)c2)CC1]

The title compound was prepared from 3-(4-chloro-benzenesulfonyl)-benzaldehyde. $^1$H NMR (400 MHz, CDCl$_3$):

7.94-7.85 (m, 6H), 7.54-7.45 (m, 6H), 7.06-7.00 (m, 1H), 6.29 (s, 1H), 3.58 (s, 2H), 3.53-3.47 (m, 4H), 2.50-2.49 (m, 4H).

Example 73

4-(1H-Indol-6-ylmethyl)-piperazine-1-carboxylic acid phenylamide

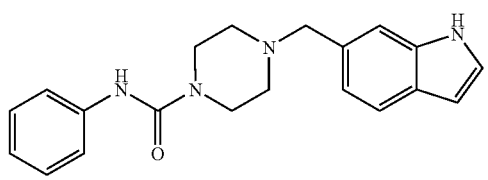 [SMILES: O=C(Nc1ccccc1)N1CCN(Cc2ccc3cc[nH]c3c2)CC1]

The title compound was prepared from indole-6-carboxaldehyde. $^1$H NMR (400 MHz, CDCl$_3$): 8.15 (s, 1H), 7.62-7.58 (m, 1H), 7.40-7.19 (m, 6H), 7.12-6.99 (m, 2H), 6.53-6.56 (m, 1H), 6.29 (s, 1H), 3.66 (s, 2H), 3.54-3.47 (m, 4H), 2.55-2.50 (m, 4H).

Example 74

4-(4-Phenoxy-benzyl)-piperazine-1-carboxylic acid phenylamide

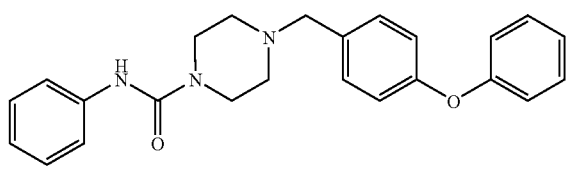 [SMILES: O=C(Nc1ccccc1)N1CCN(Cc2ccc(Oc3ccccc3)cc2)CC1]

The title compound was prepared from 4-phenoxybenzaldehyde. $^1$H NMR (400 MHz, CDCl$_3$): 7.40-7.25 (m, 8H), 7.15-6.95 (m, 6H), 6.31 (s, 1H), 3.55-3.48 (m, 6H), 2.55-2.45 (m, 4H).

Example 75

4-(2-Chloro-8-methyl-quinolin-3-ylmethyl)-piperazine-1-carboxylic acid phenylamide

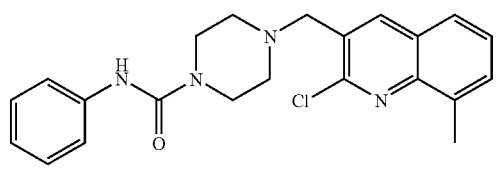

The title compound was prepared from 2-chloro-8-methyl-quinoline-3-carbaldehyde. $^1$H NMR (400 MHz, CDCl$_3$): 8.17 (s, 1H), 7.67 (d, J=7.8 Hz, 1H), 7.56 (d, J=6.8 Hz, 1H), 7.45 (t, J=7.5 Hz, 1H), 7.37-7.33 (m, 2H), 7.30-7.25 (m, 2H), 7.05-7.00 (m, 1H), 6.46 (s, 1H), 3.77 (s, 2H), 3.54 (t, J=5.1 Hz, 4H), 2.77 (s, 3H), 2.61 (t, J=5.0 Hz, 4H).

Example 76

4-(1-Methyl-1H-indol-6-ylmethyl)-piperazine-1-carboxylic acid phenylamide

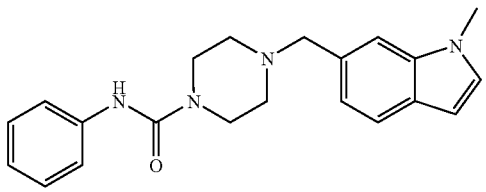 [SMILES: Cn1ccc2ccc(CN3CCN(C(=O)Nc4ccccc4)CC3)cc21]

The title compound was prepared from 1-methyl-1H-indole-6-carbaldehyde. $^1$H NMR (400 MHz, CDCl$_3$): 7.57 (d, J=8.1 Hz, 1H), 7.38-7.24 (m, 5H), 7.11-7.00 (m, 3H), 6.49-6.47 (dd, J=3.1, 0.8 Hz, 1H), 6.31 (s, 1H), 3.80 (s, 3H), 3.68 (s, 2H), 3.54-3.48 (m, 4H), 2.56-2.50 (m, 4H).

Example 77

4-(4-Benzyloxy-benzyl)-piperazine-1-carboxylic acid phenylamide

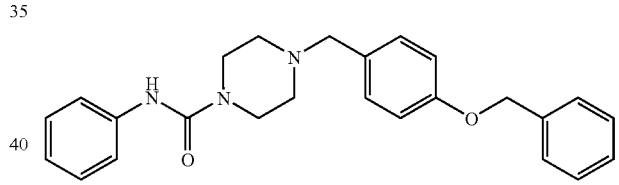

The title compound was prepared from 4-benzyloxybenzaldehyde. $^1$H NMR (400 MHz, CDCl$_3$): 7.47-7.20 (m, 11H), 7.05-6.98 (m, 1H), 6.97-6.91 (m, 2H), 5.05 (s, 2H), 3.50-3.42 (m, 6H), 2.47-2.40 (m, 4H).

Example 78

4-[3-(3,5-Dichloro-phenoxy)-benzyl]-piperazine-1-carboxylic acid phenylamide

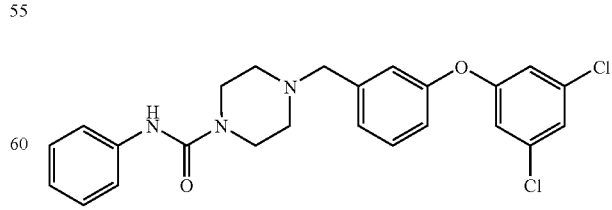

The title compound was prepared from 3-(3,5-dichlorophenoxy)-benzaldehyde. $^1$H NMR (400 MHz, CDCl$_3$): 7.37-7.25 (m, 5H), 7.16 (d, J=7.7 Hz, 1H), 7.10-7.00 (m, 3H), 6.97-6.91 (m, 1H), 6.86 (d, J=1.8 Hz, 2H), 6.31 (s, 1H), 3.57-3.47 (m, 6H), 2.53-2.45 (m, 4H).

Example 79

4-(9H-Fluoren-2-ylmethyl)-piperazine-1-carboxylic acid phenylamide

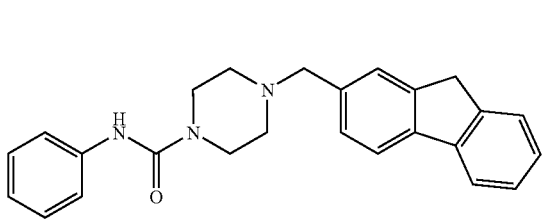 [SMILES: O=C(Nc1ccccc1)N1CCN(Cc2ccc3c(c2)Cc2ccccc2-3)CC1]

The title compound was prepared from 9H-fluorene-2-carbaldehyde. $^1$H NMR (400 MHz, CDCl$_3$): 7.79-7.72 (m, 2H), 7.55-7.50 (m, 2H), 7.40-7.23 (m, 7H), 7.04-6.99 (m, 1H), 6.40 (s, 1H), 3.90 (s, 2H), 3.60 (s, 2H), 3.50 (t, J=5.1 Hz, 4H), 2.50 (t, J=5.1 Hz, 4H).

Example 80

4-(9-Ethyl-9H-carbazol-3-ylmethyl)-piperazine-1-carboxylic acid phenylamide

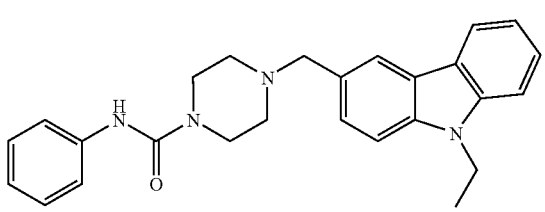 [SMILES: CCn1c2ccccc2c2cc(CN3CCN(C(=O)Nc4ccccc4)CC3)ccc21]

The title compound was prepared from 9-ethyl-9H-carbazole-3-carbaldehyde. $^1$H NMR (400 MHz, CDCl$_3$): 8.10 (d, 7.6 Hz, 1H), 8.03 (s, 1H), 7.49-7.21 (m, 9H), 7.04-6.99 (m, 1H), 6.35 (s, 1H), 4.37 (q, 7.2 Hz, 2H), 3.72 (s, 2H), 3.51 (t, J=5.1 Hz, 4H), 2.54 (t, J=5.1 Hz, 4H), 1.44 (t, J=7.2 Hz, 3H).

Example 81

4-(4-Styryl-benzyl)-piperazine-1-carboxylic acid phenylamide

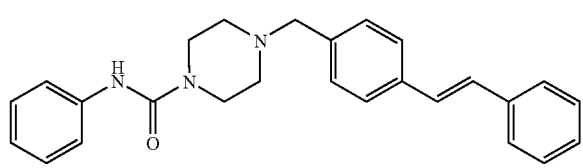 [SMILES: O=C(Nc1ccccc1)N1CCN(Cc2ccc(/C=C/c3ccccc3)cc2)CC1]

The title compound was prepared from 4-styryl-benzaldehyde. $^1$H NMR (400 MHz, CDCl$_3$): 7.54-7.47 (m, 4H), 7.39-7.25 (m, 9H), 7.11 (s, 2H), 7.05-7.00 (m, 7.00, 1H), 6.37 (s, 1H), 3.54 (s, 2H), 3.50 (t, J=5.0 Hz, 4H), 2.49 (t, J=5.0 Hz, 4H).

Example 82

4-(4-Chloro-3-trifluoromethyl-benzyl)-piperazine-1-carboxylic acid phenylamide

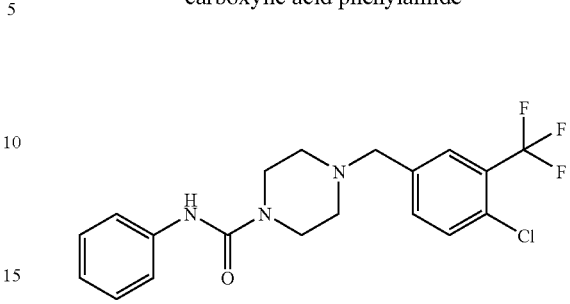

The title compound was prepared from 4-chloro-3-trifluoromethyl-benzaldehyde. $^1$H NMR (400 MHz, CDCl$_3$): 7.67 (s, 1H), 7.46 (s, 2H), 7.35-7.25 (m, 4H), 7.05-7.00 (m, 1H), 6.42 (s, 1H), 3.54 (s, 2H), 3.50 (t, J=5.1 Hz, 4H), 2.46 (t, J=5.1 Hz, 4H).

Example 83

4-[2,5-Dimethyl-1-(3-trifluoromethyl-phenyl)-1H-pyrrol-3-ylmethyl]-piperazine-1-carboxylic acid phenylamide

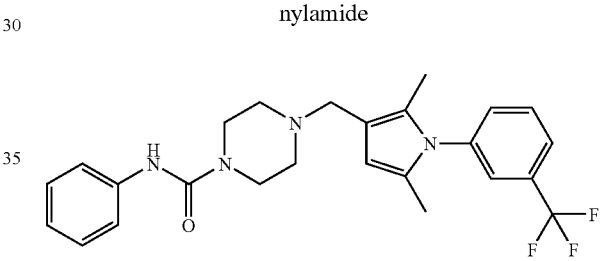

The title compound was prepared from 2,5-dimethyl-1-(3-trifluoromethyl-phenyl)-1H-pyrrole-3-carbaldehyde. $^1$H NMR (400 MHz, CDCl$_3$): 7.69-7.58 (m, 2H), 7.47 (s, 1H), 7.42-7.25 (m, 5H), 7.04-7.00 (m, 1H), 6.45 (s, 1H), 6.94 (s, 1H), 3.52 (t, J=5.1 Hz, 4H), 3.41 (s, 2H), 2.52 (t, J=5.1 Hz, 4H), 2.02 (s, 3H), 1.98 (s, 3H).

Example 84

4-(2-Bromo-benzyl)-piperazine-1-carboxylic acid phenylamide

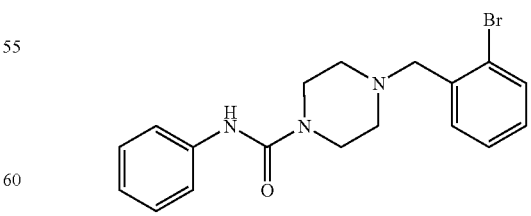

The title compound was prepared from 2-bromobenzaldehyde. $^1$H NMR (400 MHz, CDCl$_3$): 7.56 (dd, J=8.0, 1.3 Hz, 1H), 7.46 (dd, J=7.8, 1.6 Hz, 1H), 7.36-7.24 (m, 5H), 7.13 (td, J=7.7, 1.7 Hz, 1H), 7.04-6.99 (m, 1H), 6.37 (br s, 1H), 3.63 (s, 2H), 3.51-3.47 (m, 4H), 2.56-2.52 (m, 4H).

Example 85

4-(3,4-Dibromo-benzyl)-piperazine-1-carboxylic acid (3-fluoro-phenyl)-amide

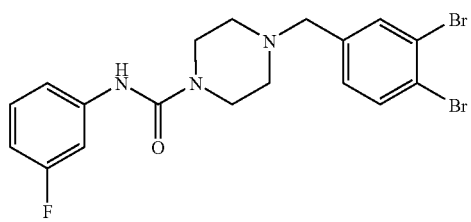 [SMILES: O=C(Nc1cccc(F)c1)N1CCN(Cc2ccc(Br)c(Br)c2)CC1]

A solution of 1-(3,4-dibromo-benzyl)-piperazine (167 mg) in DCM (2 mL) was treated with 3-fluorophenyl isocyanate (0.07 mL). After 16 h, the resulting mixture was chromatographed, giving the title compound as a white foam (188 mg). $^1$H NMR (400 MHz, CDCl$_3$): 7.61 (d, J=2.0 Hz, 1H), 7.56 (d, J=8.1 Hz, 1H), 7.31-7.12 (m, 3H), 7.01-6.97 (m, 1H), 6.75-6.99 (m, 1H), 6.47 (br m, 1H), 3.51-3.47 (m, 4H), 3.45 (s, 2H), 2.48-2.43 (m, 4H).

Examples 86-96 were prepared from 1-(3,4-dibromo-benzyl)-piperazine and the specified isocyanates in analogy with Example 85. Products were isolated either by filtration of the reaction mixture or by chromatography.

Example 86

4-(3,4-Dibromo-benzyl)-piperazine-1-carboxylic acid (4-fluoro-phenyl)-amide

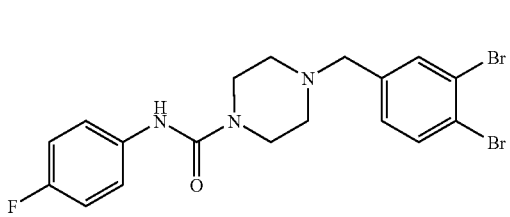 [SMILES: O=C(Nc1ccc(F)cc1)N1CCN(Cc2ccc(Br)c(Br)c2)CC1]

The title compound was prepared from 4-fluorophenyl isocyanate. $^1$H NMR (400 MHz, CDCl$_3$): 7.62 (d, J=2.0 Hz, 1H), 7.57 (d, J=8.0 Hz, 1H), 7.31-7.27 (m, 2H), 7.15 (dd, J=8.0, 2.0 Hz, 1H), 7.01-6.95 (m, 2H), 6.28 (br s, 1H), 3.51-3.47 (m, 4H), 3.46 (s, 2H), 2.50-2.45 (m, 4H).

Example 87

4-(3,4-Dibromo-benzyl)-piperazine-1-carboxylic acid (3-methoxy-phenyl)-amide

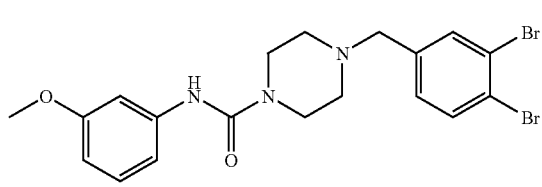 [SMILES: COc1cccc(NC(=O)N2CCN(Cc3ccc(Br)c(Br)c3)CC2)c1]

The title compound was prepared from 3-methoxyphenyl isocyanate. $^1$H NMR (400 MHz, CDCl$_3$): 7.65-7.55 (m, 2H), 7.20-7.10 (m, 3H), 6.85-6.79 (m, 1H), 6.62-6.56 (m, 1H), 6.32 (s, 1H), 3.80 (s, 3H), 3.55-3.45 (m, 6H), 2.51-2.44 (m, 4H).

Example 88

4-(3,4-Dibromo-benzyl)-piperazine-1-carboxylic acid m-tolylamide

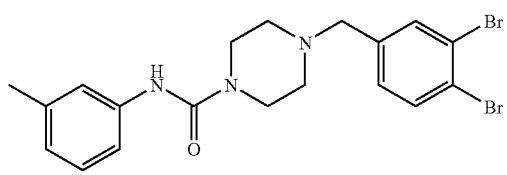 [SMILES: Cc1cccc(NC(=O)N2CCN(Cc3ccc(Br)c(Br)c3)CC2)c1]

The title compound was prepared from 3-methylphenyl isocyanate. $^1$H NMR (400 MHz, CDCl$_3$): 7.65-7.55 (m, 2H), 7.25-7.07 (m, 4H), 6.86 (d, J=7.4 Hz, 1H), 6.26 (s, 1H), 3.55-3.44 (m, 6H), 2.50-2.44 (m, 4H), 2.32 (s, 3H).

Example 89

4-(3,4-Dibromo-benzyl)-piperazine-1-carboxylic acid (2-fluoro-phenyl)-amide

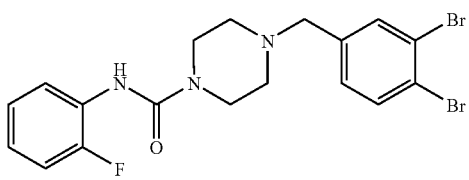 [SMILES: O=C(Nc1ccccc1F)N1CCN(Cc2ccc(Br)c(Br)c2)CC1]

The title compound was prepared from 2-fluorophenyl isocyanate. $^1$H NMR (400 MHz, CDCl$_3$): 8.08 (td, J=8.2, 1.6 Hz, 1H), 7.62 (d, J=1.8 Hz, 1H), 7.57 (d, J=8.0 Hz, 1H), 7.17-6.93 (m, 4H), 6.58 (br s, 1H), 3.55-3.50 (m, 4H), 3.47 (s, 2H), 2.51-2.46 (m, 4H).

Example 90

4-(3,4-Dibromo-benzyl)-piperazine-1-carboxylic acid (4-methoxy-phenyl)-amide

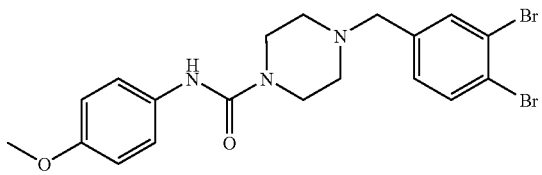 [SMILES: COc1ccc(NC(=O)N2CCN(Cc3ccc(Br)c(Br)c3)CC2)cc1]

The title compound was prepared from 4-methoxyphenyl isocyanate. $^1$H NMR (400 MHz, CDCl$_3$): 7.63-7.62 (m, 1H), 7.57 (d, J=8.0 Hz, 1H), 7.25-7.22 (m, 2H), 7.16-7.13 (m, 1H), 6.85-6.82 (m, 2H), 6.19 (s, 1H), 3.78 (s, 3H), 3.50-3.46 (m, 6H), 2.48-2.46 (m, 4H).

Example 91

4-(3,4-Dibromo-benzyl)-piperazine-1-carboxylic acid (2-methoxy-phenyl)-amide

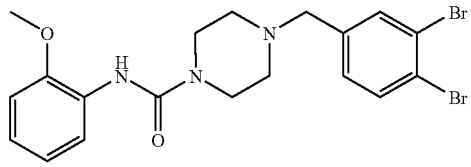 [SMILES: COc1ccccc1NC(=O)N1CCN(Cc2ccc(Br)c(Br)c2)CC1]

The title compound was prepared from 2-methoxyphenyl isocyanate. $^1$H NMR (400 MHz, CDCl$_3$): 8.15-8.13 (m, 1H), 7.63-7.56 (m, 2H), 7.16-7.09 (m, 2H), 6.96-6.93 (m, 2H), 6.86-6.83 (m, 1H), 3.87 (s, 3H), 3.53-3.51 (m, 4H), 3.46 (s, 2H), 2.50-2.47 (m, 4H).

Example 92

4-(3,4-Dibromo-benzyl)-piperazine-1-carboxylic acid (3-chloro-phenyl)-amide

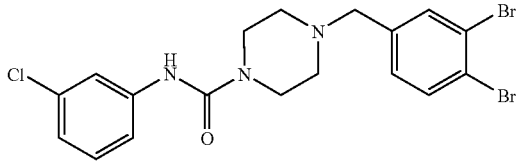 [SMILES: O=C(Nc1cccc(Cl)c1)N1CCN(Cc2ccc(Br)c(Br)c2)CC1]

The title compound was prepared from 3-chlorophenyl isocyanate. $^1$H NMR (400 MHz, CDCl$_3$): 7.62 (d, 1.9 Hz, 1H), 7.57 (d, J=8.2 Hz, 2H), 7.20-7.13 (m, 3H), 7.02-6.99 (m, 1H), 6.34 (s, 1H), 3.51-3.47 (m, 6H), 2.49-2.46 (m, 4H).

Example 93

4-(3,4-Dibromo-benzyl)-piperazine-1-carboxylic acid (2-chloro-phenyl)-amide

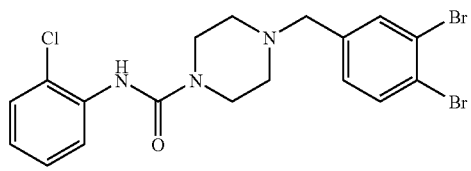 [SMILES: Cc1ccccc1NC(=O)N1CCN(Cc2ccc(Br)c(Br)c2)CC1]

The title compound was prepared from 2-chlorophenyl isocyanate. $^1$H NMR (400 MHz, CDCl$_3$): 8.20-8.18 (m, 1H), 7.63-7.56 (m, 2H), 7.34-7.14 (m, 3H), 7.00-6.93 (m, 2H), 3.56-3.54 (m, 4H), 3.48 (s, 2H), 2.51-2.49 (m, 4H).

Example 94

4-(3,4-Dibromo-benzyl)-piperazine-1-carboxylic acid p-tolylamide

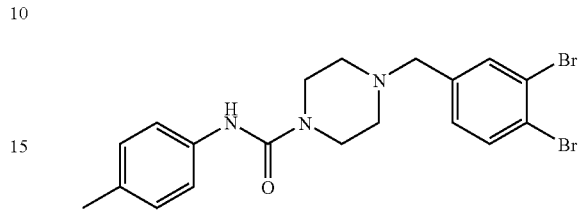

The title compound was prepared from 4-methylphenyl isocyanate. $^1$H NMR (400 MHz, CDCl$_3$): 7.62-7.55 (m, 2H), 7.23-7.07 (m, 5H), 6.25 (s, 1H), 3.50-3.46 (m, 6H), 2.48-2.45 (m, 4H), 2.29 (s, 3H).

Example 95

4-(3,4-Dibromo-benzyl)-piperazine-1-carboxylic acid (4-chloro-phenyl)-amide

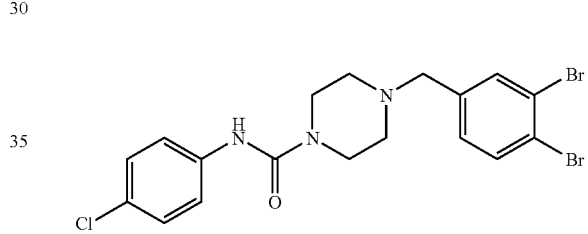

The title compound was prepared from 4-chlorophenyl isocyanate. $^1$H NMR (400 MHz, CDCl$_3$): 7.63-7.56 (m, 2H), 7.31-7.23 (m, 4H), 7.16-7.13 (m, 1H), 6.29 (s, 1H), 3.51-3.47 (m, 6H), 2.49-2.46 (m, 4H).

Example 96

4-(3,4-Dibromo-benzyl)-piperazine-1-carboxylic acid o-tolylamide

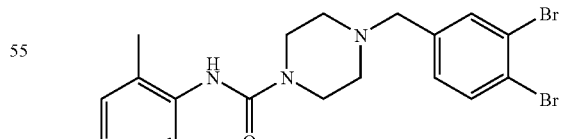

The title compound was prepared from 2-methylphenyl isocyanate. $^1$H NMR (400 MHz, CDCl$_3$): 7.63-7.56 (m, 3H), 7.21-7.13 (m, 3H), 7.04-6.99 (m, 1H), 6.10 (s, 1H), 3.52-3.47 (m, 6H), 2.50-2.47 (m, 4H).

Examples 97-115 were prepared from 3-piperazin-1-ylmethyl-quinoline (unless otherwise specified) and the specified isocyanates in analogy with Example 85. Products were isolated either by filtration of the reaction mixture or by chromatography.

Example 97

4-Quinolin-3-ylmethyl-piperazine-1-carboxylic acid (3-fluoro-phenyl)-amide

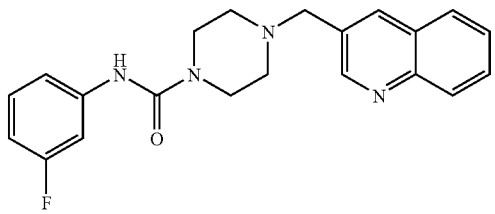 [SMILES: O=C(Nc1cccc(F)c1)N1CCN(Cc2cnc3ccccc3c2)CC1]

The title compound was prepared from 3-fluorophenyl isocyanate. ¹H NMR (400 MHz, CDCl$_3$): 7.41-7.25 (m, 9H), 7.05-7.00 (m, 1H), 6.33 (s, 1H), 3.69 (s, 2H), 3.49 (t, J=5.1 Hz, 4H), 2.54 (t, J=5.1 Hz, 4H).

Example 98

4-Quinolin-3-ylmethyl-piperazine-1-carboxylic acid (4-fluoro-phenyl)-amide

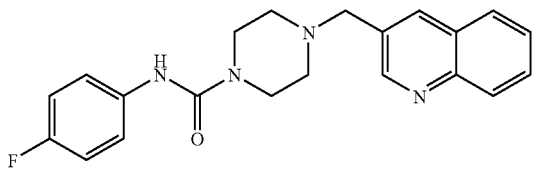 [SMILES: O=C(Nc1ccc(F)cc1)N1CCN(Cc2cnc3ccccc3c2)CC1]

The title compound was prepared from 4-fluorophenyl isocyanate. ¹H NMR (400 MHz, CDCl$_3$): 8.92 (s, 1H), 8.12-8.07 (m, 1H), 7.83-7.80 (m, 1H), 7.71 (ddd, J=8.4, 6.9, 1.5 Hz, 1H), 7.52 (ddd, J=8.0, 7.0, 1.1 Hz, 1H), 7.30-7.27 (m, 2H), 6.99-6.95 (m, 2H), 6.38 (s, 1H), 3.74 (s, 2H), 3.50-3.52 (m, 4H), 2.55-2.54 (m, 4H)

Example 99

4-Quinolin-3-ylmethyl-piperazine-1-carboxylic acid (2-chloro-phenyl)-amide

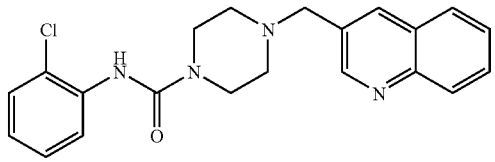 [SMILES: O=C(Nc1ccccc1Cl)N1CCN(Cc2cnc3ccccc3c2)CC1]

The title compound was prepared from 2-chlorophenyl isocyanate. ¹H NMR (400 MHz, CDCl$_3$): 8.76 (d, J=2.1 Hz, 1H), 8.02 (dd, J=8.3, 1.4 Hz, 1H), 7.97-7.90 (m, 2H), 7.67-7.64 (m, 1H), 7.55 (ddd, J=8.4, 7.0, 1.4 Hz, 1H), 7.40 (ddd, J=8.0, 7.0, 1.1 Hz, 1H), 7.15 (dd, J=8.0, 1.5 Hz, 1H), 7.08-7.05 (m, 1H), 6.83 (s, 1H), 6.80-6.76 (m, 1H), 3.41 (m, 4H), 2.43-2.40 (m, 4H).

Example 100

4-Quinolin-3-ylmethyl-piperazine-1-carboxylic acid (3-chloro-phenyl)-amide

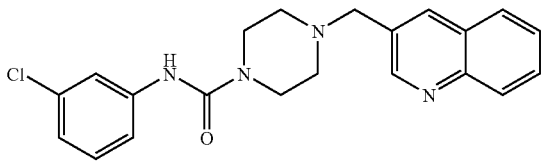 [SMILES: O=C(Nc1cccc(Cl)c1)N1CCN(Cc2cnc3ccccc3c2)CC1]

The title compound was prepared from 3-chlorophenyl isocyanate. ¹H NMR (400 MHz, CDCl$_3$): 8.93 (d, J=2.1 Hz, 1H), 8.12-8.08 (m, 2H), 7.82 (d, J=8.1 Hz), 7.72 (ddd, J=8.4, 6.9, 1.4 Hz, 1H), 7.57 (ddd, J=8.1, 7.0, 1.1 Hz, 1H), 7.48-7.46 (m, 1H), 7.19-7.18 (m, 2H), 7.01-6.98 (m, 1H), 6.36 (s, 1H), 3.75 (s, 1H), 3.54-3.51 (m, 4H), 2.57-2.55 (m, 4H).

Example 101

4-Quinolin-3-ylmethyl-piperazine-1-carboxylic acid (4-chloro-phenyl)-amide

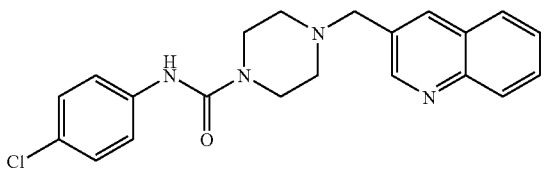 [SMILES: O=C(Nc1ccc(Cl)cc1)N1CCN(Cc2cnc3ccccc3c2)CC1]

The title compound was prepared from 4-chlorophenyl isocyanate. ¹H NMR (400 MHz, CDCl$_3$): 8.92 (d, J=2.1 Hz, 1H), 8.12-8.07 (m, 2H), 7.82 (dd, J=8.2, 1.0 Hz, 1H), 7.72 (ddd, J=8.4, 6.9, 1.4 Hz, 1H), 7.56 (ddd, J=8.1, 7.0, 1.1 Hz, 1H), 7.32-7.30 (m, 1H), 7.29-7.28 (m, 1H), 7.25-7.23 (m, 1H), 7.22-7.21 (m, 1H), 6.39 (s, 1H), 3.74 (s, 2H), 3.53-3.50 (m, 4H), 2.56-2.53 (m, 4H).

Example 102

4-Quinolin-3-ylmethyl-piperazine-1-carboxylic acid (2-methoxy-phenyl)-amide

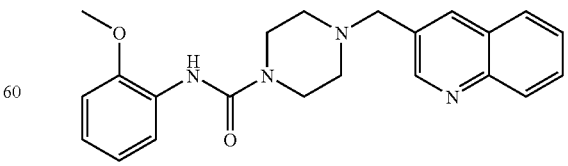

The title compound was prepared from 2-methoxyphenyl isocyanate. ¹H NMR (400 MHz, CDCl$_3$): 8.93 (d, J=2.0 Hz, 1H), 8.14-8.11 (m, 3H), 7.82 (d, J=8.4 Hz, 1H), 7.74-7.70 (m, 1H), 7.58-7.55 (m, 1H), 7.10 (s, 1H), 6.97-6.92 (m, 2H), 6.86-6.83 (m, 1H), 3.86 (s, 3H), 3.76 (s, 2H), 3.56 (s, 4H), 2.58 (s, 4H).

Example 103

4-Quinolin-3-ylmethyl-piperazine-1-carboxylic acid o-tolylamide

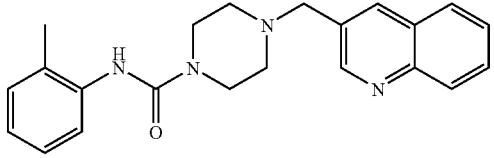 [SMILES: Cc1ccccc1NC(=O)N1CCN(Cc2cnc3ccccc3c2)CC1]

The title compound was prepared from 2-methylphenyl isocyanate. $^1$H NMR (400 MHz, CDCl$_3$): 8.92 (d, J=2.0 Hz, 1H), 8.12 (d, J=8.4 Hz, 1H), 7.82 (d, J=8.4 Hz, 1H), 7.74-7.70 (m, 2H), 7.62-7.55 (m, 2H), 7.20-7.14 (m, 2H), 7.03-6.99 (m, 1H), 6.10 (s, 1H), 3.56 (s, 2H), 3.52 (s, 4H), 2.58 (s, 4H), 2.23 (s, 3H).

Example 104

4-Quinolin-3-ylmethyl-piperazine-1-carboxylic acid p-tolylamide

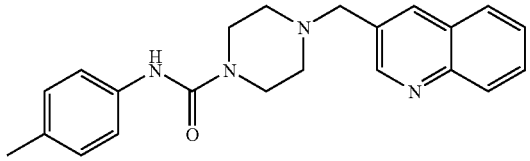 [SMILES: Cc1ccc(NC(=O)N2CCN(Cc3cnc4ccccc4c3)CC2)cc1]

The title compound was prepared from 4-methylphenyl isocyanate. $^1$H NMR (400 MHz, CDCl$_3$): 8.92 (d, J=2.0 Hz, 1H), 8.12-8.09 (m, 2H), 7.82 (dd, J=8.2, 0.8 Hz, 1H), 7.72 (ddd, J=8.4, 7.0, 1.4 Hz, 1H), 7.56 (ddd, J=8.0, 6.8, 1.0 Hz, 1H), 7.23-7.20 (m, 2H), 7.09-7.07 (m, 2H), 6.25 (s, 1H), 3.75 (s, 2H), 3.53-3.51 (m, 4H), 2.58-2.54 (m, 4H), 2.22 (s, 3H).

Example 105

2-[(4-Quinolin-3-ylmethyl-piperazine-1-carbonyl)-amino]-benzoic acid methyl ester

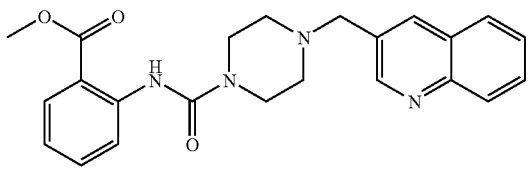 [SMILES: COC(=O)c1ccccc1NC(=O)N1CCN(Cc2cnc3ccccc3c2)CC1]

The title compound was prepared from 2-carbomethoxyphenyl isocyanate. $^1$H NMR (400 MHz, CDCl$_3$): 10.77 (s, 1H), 8.94 (d, J=2.1 Hz, 1H), 8.56 (dd, J=8.6, 0.9 Hz, 1H), 8.13-8.11 (m, 2H), 8.00 (dd, J=8.1, 1.6 Hz, 1H), 7.83 (d, J=8.0 Hz, 1H), 7.74-7.70 (m, 1H), 7.59-7.55 (m, 1H), 7.51 (ddd, J=8.8, 7.3, 1.7 Hz, 1H), 6.99-6.95 (m, 1H), 3.89 (s, 3H), 3.77 (s, 2H), 3.66-3.64 (m, 4H), 2.62-2.59 (m, 4H).

Example 106

3-[(4-Quinolin-3-ylmethyl-piperazine-1-carbonyl)-amino]-benzoic acid methyl ester

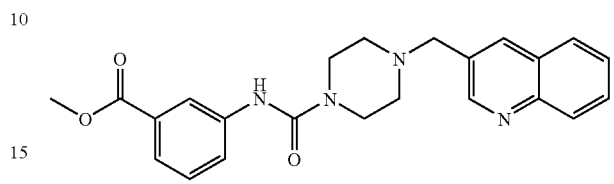

The title compound was prepared from 3-carbomethoxyphenyl isocyanate. $^1$H NMR (400 MHz, CDCl$_3$): 8.92 (d, J=2.1 Hz, 1H), 8.13-8.10 (m, 2H), 7.89 (t, J=2.2 Hz, 1H), 7.83 (dd, J=8.1, 1.1 Hz, 1H), 7.75-7.68 (m, 3H), 7.59-7.54 (m, 1H), 7.38-7.32 (m, 1H), 6.60 (s, 1H), 3.88 (s, 3H), 3.77 (s, 2H), 3.56 (t, J=4.8 Hz, 4H), 2.58 (t, J=4.6 Hz, 4H).

Example 107

4-[(4-Quinolin-3-ylmethyl-piperazine-1-carbonyl)-amino]-benzoic acid methyl ester

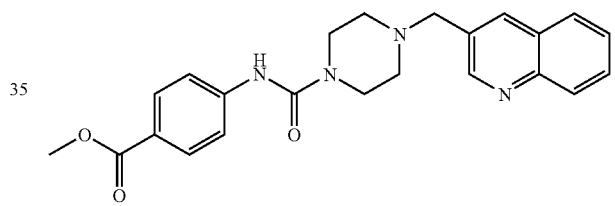

The title compound was prepared from 4-carbomethoxyphenyl isocyanate. $^1$H NMR (400 MHz, CDCl$_3$): 8.92 (d, J=2.1 Hz, 1H), 8.12-8.05 (m, 2H), 7.97-7.94 (m, 2H), 7.83-7.80 (m, 1H), 7.71 (ddd, J=8.4, 6.9, 1.4 Hz, 1H), 7.56 (ddd, J=8.1, 6.9, 1.1 Hz, 1H), 7.46-7.42 (m, 2H), 6.64 (s, 1H), 3.87 (s, 3H), 3.73 (s, 2H), 3.54 (t, J=5.0 Hz, 4H), 2.55 (t, J=5.0 Hz, 4H).

Example 108

4-Quinolin-3-ylmethyl-piperazine-1-carboxylic acid (4-methoxy-phenyl)-amide

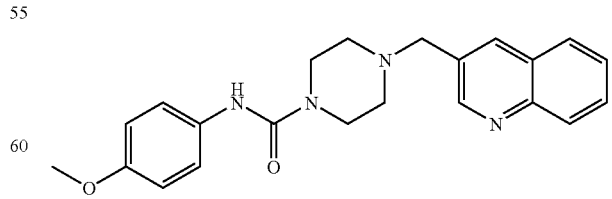

The title compound was prepared from 4-methoxyphenyl isocyanate. $^1$H NMR (400 MHz, CDCl$_3$): 8.92 (d, J=2.1 Hz, 1H), 8.12-8.08 (m, 2H), 7.82 (d, J=7.2 Hz, 1H), 7.71 (ddd, J=8.4, 6.9, 1.4 Hz, 1H), 7.56 (ddd, J=8.1, 7.0, 1.1 Hz, 1H), 7.25-7.22 (m, 2H), 6.86-6.81 (m, 2H), 6.19 (s, 1H), 3.77 (s, 3H), 3.74 (s, 2H), 3.51 (t, J=5.0 Hz, 4H), 2.56 (t, J=4.8 Hz, 4H).

Example 109

4-Quinolin-3-ylmethyl-piperazine-1-carboxylic acid m-tolylamide

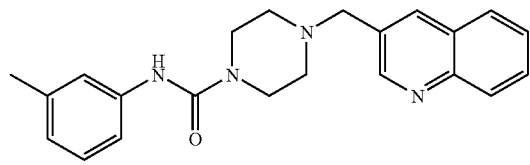 [SMILES: Cc1cccc(NC(=O)N2CCN(Cc3cnc4ccccc4c3)CC2)c1]

The title compound was prepared from 3-methylphenyl isocyanate. ¹H NMR (400 MHz, CDCl$_3$): 8.92 (d, J=2.1 Hz, 1H), 8.15-8.10 (m, 2H), 7.83 (dd, J=8.2, 1.0 Hz, 1H), 7.72 (ddd, J=8.4, 6.9, 1.4 Hz, 1H), 7.60-7.54 (m, 1H), 7.22 (s, 1H), 7.18-7.13 (m, 1H), 7.12-7.07 (m, 1H), 6.85 (d, J=7.3 Hz, 1H), 6.27 (s, 1H), 3.76 (s, 2H), 3.56-3.51 (m, 4H), 2.60-2.54 (m, 4H), 2.31 (s, 3H).

Example 110

4-Quinolin-3-ylmethyl-piperazine-1-carboxylic acid (3-methoxy-phenyl)-amide

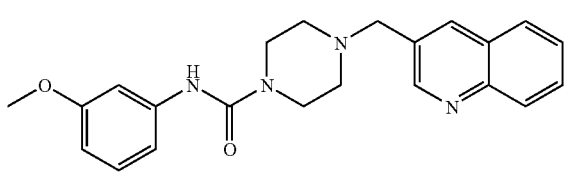 [SMILES: COc1cccc(NC(=O)N2CCN(Cc3cnc4ccccc4c3)CC2)c1]

The title compound was prepared from 3-methoxyphenyl isocyanate. ¹H NMR (400 MHz, CDCl$_3$): 8.93 (d, J=2.0 Hz, 1H), 8.13-8.07 (m, 2H), 7.82 (d, J=8.1 Hz, 1H), 7.72 (ddd, J=8.4, 7.0, 1.4 Hz, 1H), 7.59-7.54 (m, 1H), 7.19-7.14 (m, 1H), 7.13 (t, J=2.2 Hz, 1H), 6.81 (dd, J=7.7, 1.6 Hz, 1H), 6.59 (dd, J=8.0, 2.1 Hz, 1H), 6.31 (s, 1H), 3.79 (s, 3H), 3.74 (s, 2H), 3.52 (t, J=4.8 Hz, 4H), 2.56 (t, J=4.8 Hz, 4H).

Example 111

4-Quinolin-3-ylmethyl-piperazine-1-carboxylic acid (2,4-difluoro-phenyl)-amide

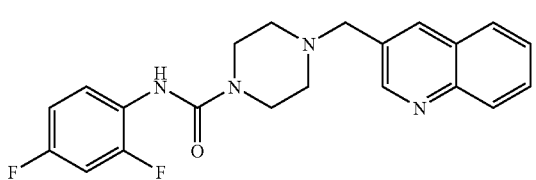 [SMILES: O=C(Nc1ccc(F)cc1F)N1CCN(Cc2cnc3ccccc3c2)CC1]

The title compound was prepared from 2,4-difluorophenylisocyanate. ¹H NMR (400 MHz, CDCl$_3$): 8.92 (d, J=2.0 Hz, 1H), 8.11 (d, J=8.6 Hz, 1H), 8.06 (s, 1H), 7.99-7.92 (m, 1H), 7.82 (dd, J=8.3, 1.1 Hz, 1H), 7.73-7.69 (m, 1H), 7.58-7.54 (m, 1H), 6.87-7.79 (m, 2H), 6.52 (s, 1H), 3.73 (s, 2H), 3.53 (t, J=5.1 Hz, 4H), 2.55 (t, J=5.1 Hz, 4H).

Example 112

4-Quinolin-3-ylmethyl-piperazine-1-carboxylic acid (2-fluoro-phenyl)-amide

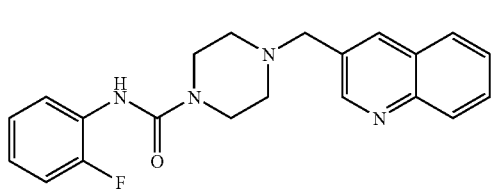 [SMILES: O=C(Nc1ccccc1F)N1CCN(Cc2cnc3ccccc3c2)CC1]

The title compound was prepared from 2-fluorophenylisocyanate. ¹H NMR (400 MHz, CDCl$_3$): 8.92 (d, J=2.0 Hz, 1H), 8.13-8.05 (m, 3H), 7.82 (dd, J=8.1, 1.3 Hz, 1H), 7.74-7.69 (m, 1H), 7.58-7.54 (m, 1H), 7.12-7.01 (m, 2H), 6.98-6.92 (m, 1H), 6.61 (d, J=3.5 Hz, 1H), 3.74 (s, 2H), 3.55 (t, J=5.1 Hz, 4H), 2.56 (t, J=5.1 Hz, 4H).

Example 113

4-Benzyl-piperidine-1-carboxylic acid p-tolylamide

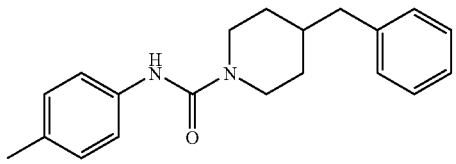 [SMILES: Cc1ccc(NC(=O)N2CCC(Cc3ccccc3)CC2)cc1]

The title compound was prepared from 4-benzylpiperidine and 4-phenylphenyl isocyanate. ¹H NMR (400 MHz, CDCl$_3$): 7.31-7.12 (m, 7H), 7.07 (d, J=8.0 Hz, 2H), 6.32 (s, 1H), 4.06-4.00 (m, 2H), 2.79 (td, J=13, 2.5 Hz, 2H), 2.56 (d, J=6.8 Hz, 2H), 2.28 (s, 3H), 1.79-0.165 (m, 3H), 1.30-1.18 (m, 2H).

Example 114

4-Benzyl-piperidine-1-carboxylic acid m-tolylamide

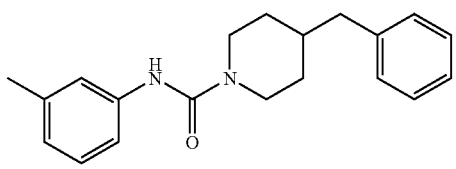 [SMILES: Cc1cccc(NC(=O)N2CCC(Cc3ccccc3)CC2)c1]

The title compound was prepared from 4-benzylpiperidine and 3-methylphenyl isocyanate. ¹H NMR (400 MHz, CDCl$_3$): 7.32-7.07 (m, 8H), 6.84-6.80 (m, 1H), 6.41 (br s, 1H), 4.06-4.00 (m, 2H), 2.78 (td, J=13, 2.4 Hz, 2H), 2.55 (d, J=7.0 Hz, 2H), 2.30 (s, 3H), 1.77-1.64 (m, 3H), 1.28-1.16 (m, 2H).

Example 115

4-Benzyl-piperidine-1-carboxylic acid (2-chloro-phenyl)-amide

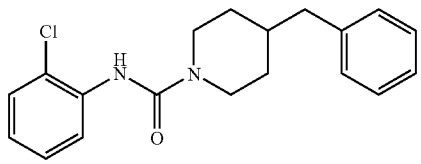 [SMILES: O=C(Nc1ccccc1Cl)N1CCC(Cc2ccccc2)CC1]

The title compound was prepared from 4-benzylpiperidine and 2-chlorophenyl isocyanate. $^1$H NMR (400 MHz, CDCl$_3$): 8.19 (dd, J=8.3, 1.5 Hz, 1H), 7.33-7.12 (m, 7H), 7.03 (br s, 1H), 6.96-6.90 (m, 1H), 4.12-4.05 (m, 2H), 2.85 (td, J=13, 2.3 Hz, 2H), 2.57 (d, J=6.8 Hz, 2H), 1.82-1.69 (m, 3H), 1.34-1.20 (m, 2H).

Example 116

4-(3,4-Dibromo-benzyl)-piperazine-1-carboxylic acid pyridin-4-ylamide

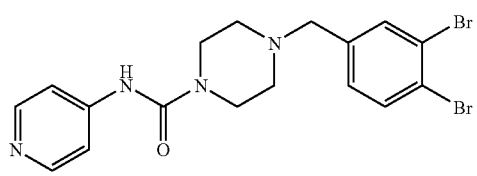 [SMILES: O=C(Nc1ccncc1)N1CCN(Cc2ccc(Br)c(Br)c2)CC1]

A mixture of 1-(3,4-dibromo-benzyl)-piperazine (316 mg) and pyridin-4-yl-carbamic acid phenyl ester (204 mg) in DMSO (4 mL) was stirred at rt for 16 h. The resulting mixture was diluted with EtOAc (20 mL) and washed with satd. aq. NaHCO$_3$ (2 mL). The organic layer was dried (MgSO$_4$) and concentrated. Chromatography of the residue gave a white solid (370 mg). $^1$H NMR (400 MHz, CDCl$_3$): 8.45-8.40 (m, 2H), 7.62 (d, J=1.9 Hz, 1H), 7.57 (d, J=8.2 Hz, 1H), 7.35-7.30 (m, 2H), 7.16-7.12 (m, 1H), 6.59 (s, 1H), 3.56-3.50 (m, 4H), 3.47 (s, 2H), 2.51-2.45 (m, 4H).

Examples 117-118 were prepared from 1-(3,4-dibromo-benzyl)-piperazine and the specified aryl carbamate in analogy with Example 116.

Example 117

4-(3,4-Dibromo-benzyl)-piperazine-1-carboxylic acid pyridin-2-ylamide

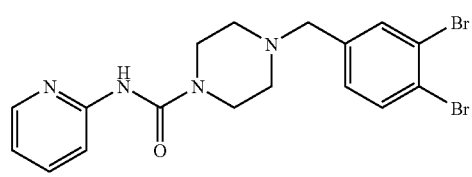 [SMILES: O=C(Nc1ccccn1)N1CCN(Cc2ccc(Br)c(Br)c2)CC1]

The title compound was prepared from pyridin-2-yl-carbamic acid phenyl ester. $^1$H NMR (400 MHz, CDCl$_3$): 8.22-8.18 (m, 1H), 8.05-8.01 (m, 1H), 7.70-7.55 (m, 3H), 7.16-7.12 (m, 1H), 6.98-6.90 (m, 2H), 3.56-3.50 (m, 4H), 3.46 (s, 2H), 2.49-2.46 (m, 4H).

Example 118

4-(3,4-Dibromo-benzyl)-piperazine-1-carboxylic acid pyridin-3-ylamide

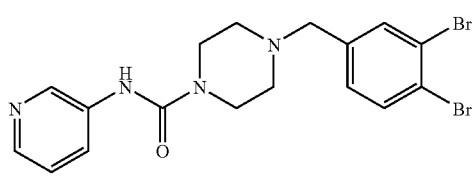 [SMILES: O=C(Nc1cccnc1)N1CCN(Cc2ccc(Br)c(Br)c2)CC1]

The title compound was prepared from pyridin-3-yl-carbamic acid phenyl ester. $^1$H NMR (400 MHz, CDCl$_3$): 8.44-8.41 (m, 1H), 8.29-8.27 (m, 1H), 8.01-7.96 (m, 1H), 7.65-7.52 (m, 2H), 7.26-7.21 (m, 1H), 7.17-7.11 (m, 1H), 6.43 (s, 1H), 3.56-3.51 (m, 4H), 3.48 (s, 2H), 2.53-2.46 (m, 4H).

Example 119

4-(4-cyclohexyloxy-benzyl)-piperazine-1-carboxylic acid phenylamide

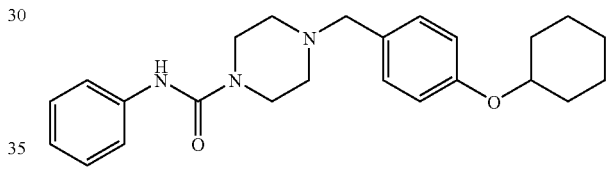

To a mixture of 4-(4-hydroxy-benzyl)-piperazine-1-carboxylic acid phenylamide (311 mg) and cyclohexanol (150 mg) in DCM (4 mL) was added polymer-supported Ph$_3$P (500 mg) followed by di-tert-butyl azodicarboxylate (345 mg). The reaction mixture was shaken overnight, and filtered. Chromatography of the filtrate gave the title compound as a white solid (110 mg). $^1$H NMR (400 MHz, CDCl$_3$): 7.36-7.19 (m, 6H), 7.05-7.00 (m, 1H), 6.88-6.84 (m, 2H), 6.30 (s, 1H), 4.25-4.20 (m, 1H), 3.50-3.47 (m, 6H), 2.48-2.46 (m, 4H), 2.01-1.97 (m, 2H), 1.82-1.80 (m, 2H), 1.60-1.29 (m, 6H).

Examples 120-129 were prepared from 4-(3-hydroxy-benzyl)-piperazine-1-carboxylic acid phenylamide or 4-(4-hydroxy-benzyl)-piperazine-1-carboxylic acid phenylamide and the specified alcohols in analogy with Example 119.

Example 120

4-(3-Propoxy-benzyl)-piperazine-1-carboxylic acid phenylamide

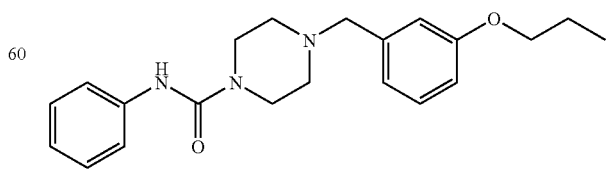

The title compound was prepared from 1-propanol. $^1$H NMR (400 MHz, CDCl$_3$): 7.36-7.21 (m, 5H), 7.05-6.90 (m, 1H), 6.88-6.80 (m, 3H), 6.32 (s, 1H), 3.94-3.91 (m, 2H), 3.51-3.49 (m, 6H), 2.50-2.48 (m, 4H), 1.86-1.77 (m, 2H), 1.06-0.98 (m, 3H).

Example 121

4-(3-Isobutoxy-benzyl)-piperazine-1-carboxylic acid phenylamide

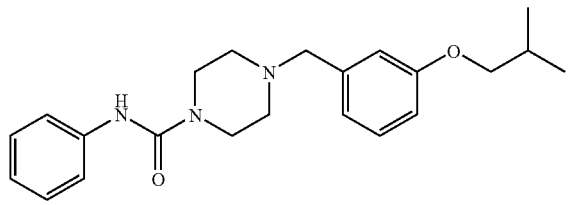 [SMILES: CC(C)COc1cccc(CN2CCN(C(=O)Nc3ccccc3)CC2)c1]

The title compound was prepared isobutanol. $^1$H NMR (400 MHz, CDCl$_3$): 7.36-7.21 (m, 5H), 7.05-7.01 (m, 1H), 6.90-6.88 (m, 2H), 6.82-6.80 (m, 1H), 6.33 (s, 1H), 3.72 (d, J=6.6 Hz, 2H), 3.21-3.49 (m, 6H), 2.50-2.48 (m, 4H), 2.12-2.05 (m, 1H), 1.03 (d, J=6.7 Hz, 3H).

Example 122

4-(3-Ethoxy-benzyl)-piperazine-1-carboxylic acid phenylamide

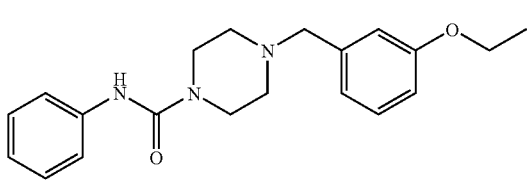 [SMILES: CCOc1cccc(CN2CCN(C(=O)Nc3ccccc3)CC2)c1]

The title compound was prepared from ethanol. $^1$H NMR (400 MHz, CDCl$_3$): 7.36-7.21 (m, 5H), 7.05-7.01 (m, 1H), 6.91-6.89 (m, 2H), 6.82-6.79 (m, 1H), 6.30 (s, 1H), 4.07-4.02 (m, 2H), 3.51-3.49 (m, 6H), 2.50-2.48 (m, 4H), 1.43-1.40 (m, 3H).

Example 123

4-(4-Propoxy-benzyl)-piperazine-1-carboxylic acid phenylamide

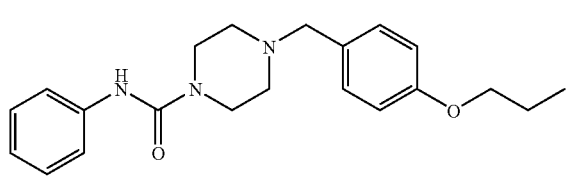 [SMILES: CCCOc1ccc(CN2CCN(C(=O)Nc3ccccc3)CC2)cc1]

The title compound was prepared from 1-propanol. $^1$H NMR (400 MHz, CDCl$_3$): 7.36-7.20 (m, 6H), 7.05-7.01 (m, 1H), 6.88-6.84 (m, 2H), 6.30 (s, 1H), 3.93-3.90 (m, 2H), 3.50-3.48 (m, 6H), 2.48-2.46 (m, 4H), 1.85-1.76 (m, 2H), 1.06-1.02 (m, 3H).

Example 124

4-(4-Isobutoxy-benzyl)-piperazine-1-carboxylic acid phenylamide

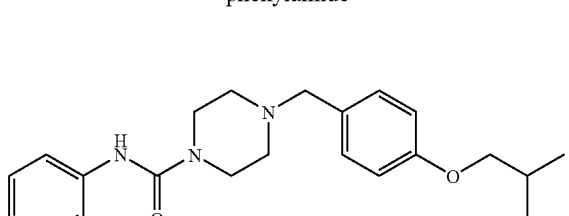

The title compound was prepared from iso-butanol. $^1$H NMR (400 MHz, CDCl$_3$): 7.35-7.20 (m, 6H), 7.05-7.00 (m, 1H), 6.88-6.84 (m, 2H), 6.31 (s, 1H), 3.71 (d, J=6.6 Hz, 2H), 3.50-3.47 (m, 6H), 2.48-2.45 (m, 4H), 2.11-2.05 (m, 1H), 1.02 (d, J=6.7 Hz, 6H).

Example 125

4-[3-(2-Dimethylamino-ethoxy)-benzyl]-piperazine-1-carboxylic acid phenylamide

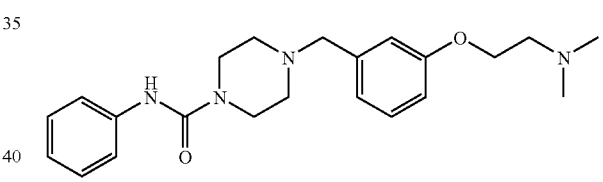

The title compound was prepared from 2-dimethylamino-ethanol. $^1$H NMR (400 MHz, CDCl$_3$): 7.39-7.20 (m, 5H), 7.06-6.99 (m, 1H), 6.96-6.88 (m, 2H), 6.86-6.80 (m, 1H), 6.32 (s, 1H), 4.08 (t, J=5.7 Hz, 2H), 3.56-3.46 (m, 6H), 2.75 (t, J=5.7 Hz, 2H), 2.52-2.45 (m, 4H), 2.36 (s, 6H).

Example 126

4-[3-(2-Piperidin-1-yl-ethoxy)-benzyl]-piperazine-1-carboxylic acid phenylamide

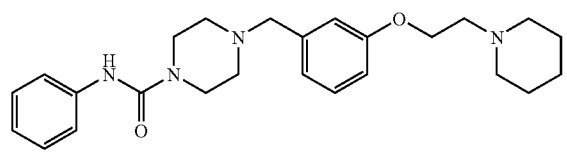 [SMILES: O=C(Nc1ccccc1)N1CCN(Cc2cccc(OCCN3CCCCC3)c2)CC1]

The title compound was prepared from 2-piperidin-1-yl-ethanol. $^1$H NMR (400 MHz, CDCl$_3$): 7.40-7.20 (m, 5H), 7.06-6.99 (m, 1H), 6.94-6.79 (m, 3H), 6.34 (s, 1H), 4.11 (t, J=6.1 Hz, 2H), 3.55-3.45 (m, 6H), 2.78 (t, J=6.1 Hz, 2H), 2.57-2.40 (m, 8H), 1.68-1.51 (m, 4H), 1.50-1.40 (m, 2H).

Example 127

4-[3-(3-Dimethylamino-propoxy)-benzyl]-piperazine-1-carboxylic acid phenylamide

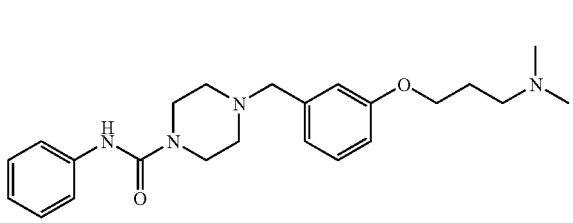 [SMILES: CN(C)CCCOc1cccc(CN2CCN(C(=O)Nc3ccccc3)CC2)c1]

The title compound was prepared from 3-dimethylamino-propan-1-ol. ¹H NMR (400 MHz, CDCl₃): 7.40-7.19 (m, 5H), 7.06-7.00 (m, 1H), 6.92-6.79 (m, 3H), 6.33 (s, 1H), 4.02 (t, J=6.4 Hz, 2H), 3.55-3.45 (m, 6H), 2.51-2.45 (m, 6H), 2.57 (s, 6H), 2.02-1.92 (m, 2H).

Example 128

4-[3-(3-Piperidin-1-yl-propoxy)-benzyl]-piperazine-1-carboxylic acid phenylamide

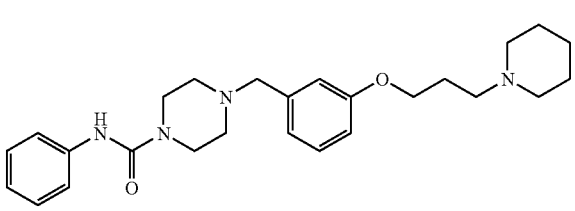 [SMILES: O=C(Nc1ccccc1)N1CCN(Cc2cccc(OCCCN3CCCCC3)c2)CC1]

The title compound was prepared from 3-piperidin-1-yl-propan-1-ol. ¹H NMR (400 MHz, CDCl₃): 7.37-7.19 (m, 5H), 7.07-7.00 (m, 1H), 6.93-6.77 (m, 3H), 6.32 (s, 1H), 4.01 (t, J=6.4 Hz, 2H), 3.55-3.45 (m, 6H), 2.60-2.30 (m, 10H), 2.04-1.94 (m, 2H), 1.79-1.39 (m, 6H).

Example 129

4-(4-Ethoxy-benzyl)-piperazine-1-carboxylic acid phenylamide

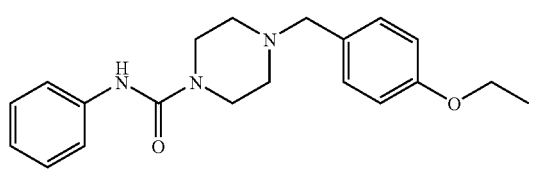

The title compound was prepared from ethanol. ¹H NMR (400 MHz, CDCl₃): 7.36-7.21 (m, 6H), 7.05-7.01 (m, 1H), 6.88-6.85 (m, 2H), 6.30 (s, 1H), 4.06-4.00 (m, 2H), 3.50-3.48 (m, 6H), 2.48-2.46 (m, 4H), 1.43-1.40 (m, 3H).

Example 130

4-[3-(3-Chloro-phenoxy)-benzyl]-piperazine-1-carboxylic acid phenylamide

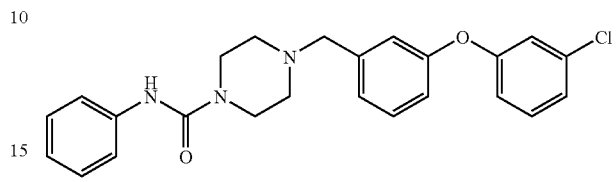

To a mixture or 4-(3-hydroxy-benzyl)-piperazine-1-carboxylic acid phenylamide (311 mg), 3-chlorophenylboronic acid (313 mg), Cu(OAc)₂ (182 mg) and powdered 4 Å molecular sieves (300 mg) in DCM (10 mL) was added pyridine (0.403 mL). The resulting mixture was stirred at rt under ambient atmosphere for 16 h, filtered, and washed with DCM. The filtrate was concentrated and the residue was chromatographed to give a brown solid (350 mg). ¹H NMR (400 MHz, CDCl₃): 7.36-7.22 (m, 6H), 7.15-6.85 (m, 7H), 6.37 (m, 1H), 3.56-3.46 (m, 6H), 2.55-2.45 (m, 4H).

Examples 131-136 were prepared from 4-(3-hydroxy-benzyl)-piperazine-1-carboxylic acid phenylamide and the specified areneboronic acids in analogy with Example 130.

Example 131

4-[3-(Naphthalen-2-yloxy)-benzyl]-piperazine-1-carboxylic acid phenylamide

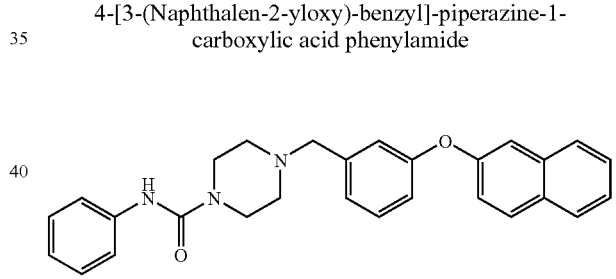

The title compound was prepared from 2-naphthylboronic acid. ¹H NMR (400 MHz, CDCl₃): 7.86-7.81 (m, 2H), 7.73-7.65 (m, 1H), 7.50-7.38 (m, 2H), 7.36-7.24 (m, 7H), 7.14-6.95 (m, 4H), 6.30 (s, 1H), 3.55-3.45 (m, 6H), 2.55-2.45 (m, 4H).

Example 132

4-[3-(Phenanthren-9-yloxy)-benzyl]-piperazine-1-carboxylic acid phenylamide

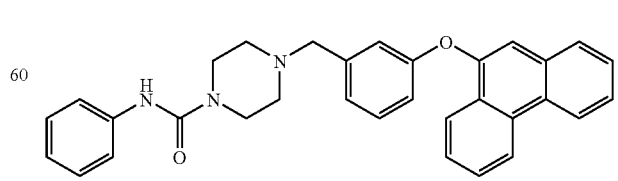

The title compound was prepared from 9-phenanthreneboronic acid. ¹H NMR (400 MHz, CDCl₃): 8.71-8.60 (m, 2H), 8.35-8.31 (m, 1H), 7.76-7.50 (m, 7H), 7.36-7.25 (m, 3H), 7.16-7.00 (m, 5H), 6.33 (s, 1H), 3.54 (s, 2H), 3.48-3.43 (m, 4H), 2.51-2.45 (m, 4H).

Example 133

4-[3-(4-Phenylcarbamoyl-piperazin-1-ylmethyl)-phenoxy]-benzoic acid methyl ester

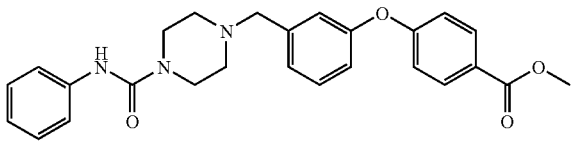 [SMILES: COC(=O)c1ccc(Oc2cccc(CN3CCN(C(=O)Nc4ccccc4)CC3)c2)cc1]

The title compound was prepared from 4-carbomethoxyphenylboronic acid. ¹H NMR (400 MHz, CDCl₃): 8.65-8.60 (m, 2H), 8.05-7.97 (m, 2H), 7.75-7.68 (m, 1H), 7.28-7.25 (m, 2H), 7.17-7.13 (m, 1H), 7.10-6.95 (m, 5H), 6.40 (s, 1H), 3.91 (s, 3H), 3.57-3.47 (m, 6H), 2.54-2.47 (m, 4H).

Example 134

4-[3-(4-Methanesulfonyl-phenoxy)-benzyl]-piperazine-1-carboxylic acid phenylamide

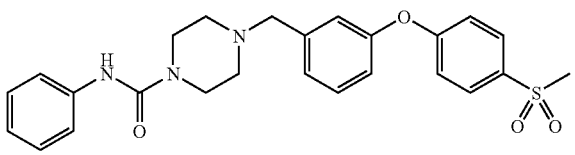 [SMILES: CS(=O)(=O)c1ccc(Oc2cccc(CN3CCN(C(=O)Nc4ccccc4)CC3)c2)cc1]

The title compound was prepared from 4-methanesulfonyl-boronic acid. ¹H NMR (400 MHz, CDCl₃): 7.92-7.86 (m, 2H), 7.41-7.18 (m, 6H), 7.12-6.93 (m, 5H), 6.31 (s, 1H), 3.57 (s, 2H), 3.54-3.48 (m, 4H), 3.06 (s, 3H), 2.55-2.47 (m, 4H).

Example 135

4-[3-(3-Methoxy-phenoxy)-benzyl]-piperazine-1-carboxylic acid phenylamide

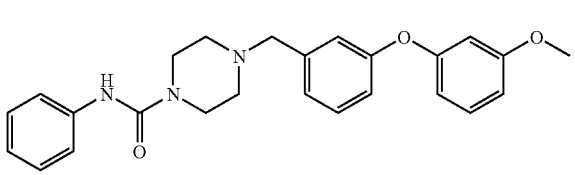 [SMILES: COc1cccc(Oc2cccc(CN3CCN(C(=O)Nc4ccccc4)CC3)c2)c1]

The title compound was prepared from 3-methoxyphenyl-boronic acid. ¹H NMR (400 MHz, CDCl₃): 7.36-7.20 (m, 6H), 7.10-7.00 (m, 3H), 6.95-6.90 (m, 1H), 6.68-6.55 (m, 3H), 6.30 (s, 1H), 3.78 (s, 3H), 3.55-3.45 (m, 6H), 2.53-2.46 (m, 4H).

Example 136

4-[3-(Benzo[1,3]dioxol-5-yloxy)-benzyl]-piperazine-1-carboxylic acid phenylamide

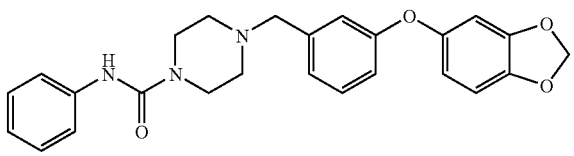 [SMILES: O=C(Nc1ccccc1)N1CCN(Cc2cccc(Oc3ccc4c(c3)OCO4)c2)CC1]

The title compound was prepared from benzo[1,3]dioxole-5-boronic acid. ¹H NMR (400 MHz, CDCl₃): 7.36-7.22 (m, 5H), 7.06-6.95 (m, 3H), 6.88-6.82 (m, 1H), 6.76 (d, J=8.4 Hz, 1H), 6.58 (d, J=2.4 Hz, 1H), 6.49 (dd, J=8.4, 2.4 Hz, 1H), 6.34 (s, 1H), 3.55-3.45 (m, 6H), 2.53-2.46 (m, 4H).

Example 137

Methanesulfonic acid 3-(4-phenylcarbamoyl-piperazin-1-ylmethyl)-phenyl ester

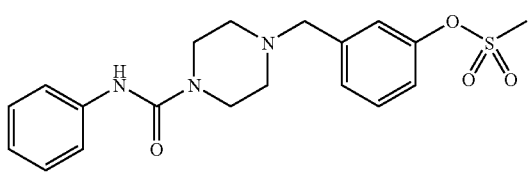 [SMILES: CS(=O)(=O)Oc1cccc(CN2CCN(C(=O)Nc3ccccc3)CC2)c1]

To a 0° C. solution of 4-(3-hydroxy-benzyl)-piperazine-1-carboxylic acid phenylamide (50 mg) in DCM (1 mL) was added methanesulfonyl chloride (0.015 mL) followed by Et₃N (0.029 mL). The resulting mixture was stirred at rt for 2 h, and chromatographed to give a colorless oil (80 mg). ¹H NMR (400 MHz, CDCl₃): 7.42-7.22 (m, 7H), 7.22-7.16 (m, 1H), 7.07-7.01 (m, 1H), 3.65-3.46 (m, 6H), 3.22-3.15 (m, 3H), 2.60-2.45 (m, 4H).

Examples 138-139 were prepared from 4-(3-hydroxy-benzyl)-piperazine-1-carboxylic acid phenylamide in analogy with Example 137 using the specified sulfonyl chloride.

Example 138

Benzenesulfonic acid 3-(4-phenylcarbamoyl-piperazin-1-ylmethyl)-phenyl ester

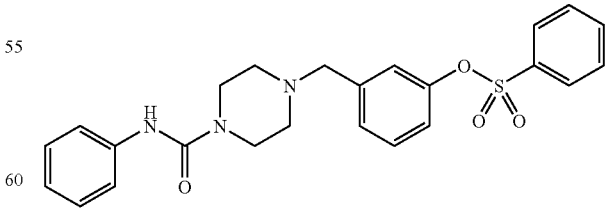

The title compound was prepared from benzenesulfonyl chloride. ¹H NMR (400 MHz, CDCl₃): 7.87-7.82 (m, 2H), 7.71-7.65 (m, 1H), 7.56-7.50 (m, 2H), 7.37-7.18 (m, 6H), 7.07-6.98 (m, 2H), 6.95-6.89 (m, 1H), 6.30 (s, 1H), 3.50-3.43 (m, 6H), 2.45-2.35 (m, 4H).

Example 139

4-Chloro-benzenesulfonic acid 3-(4-phenylcarbamoyl-piperazin-1-ylmethyl)-phenyl ester

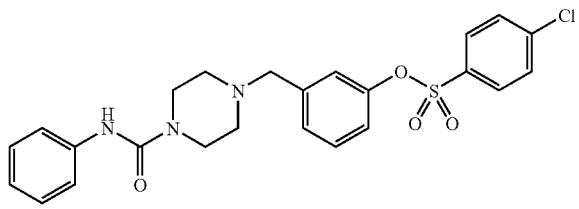 [SMILES: O=C(Nc1ccccc1)N1CCN(Cc2cccc(OS(=O)(=O)c3ccc(Cl)cc3)c2)CC1]

The title compound was prepared from 4-chloro-benzenesulfonyl chloride. $^1$H NMR (400 MHz, CDCl$_3$): 7.81-7.79 (m, 2H), 7.54-7.49 (m, 2H), 7.40-7.20 (m, 6H), 7.09-6.89 (m, 3H), 6.30 (s, 1H), 3.52-2.45 (m, 6H), 2.45-2.37 (m, 4H).

Example 140

2-[(4-Quinolin-3-ylmethyl-piperazine-1-carbonyl)-amino]-benzoic acid (potassium salt)

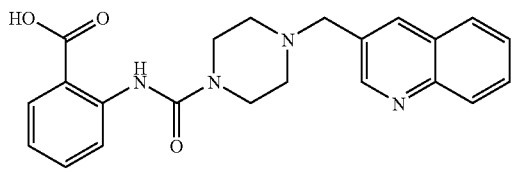 [SMILES: O=C(O)c1ccccc1NC(=O)N1CCN(Cc2cnc3ccccc3c2)CC1]

To a solution of 2-[(4-quinolin-3-ylmethyl-piperazine-1-carbonyl)-amino]-benzoic acid methyl ester (26 mg) in THF (0.5 mL) under N$_2$ was added potassium trimethyl silanoate (9 mg) in one portion and the mixture was stirred at rt for 14 h. The mixture was concentrated to give the title compound as a white amorphous solid (22 mg). $^1$H NMR (400 MHz, CD$_3$OD): 8.81 (d, J=2.1 Hz, 1H), 8.23-8.21 (m, 1H), 8.14 (dd, J=8.4, 0.9 Hz, 1H), 7.96-7.93 (m, 1H), 7.91 (dd, J=7.9, 1.6 Hz, 1H), 7.88-7.85 (m, 1H), 7.68 (ddd, J=8.4, 6.9, 1.4 Hz, 1H), 7.54 (ddd, J=8.1, 7.0, 1.1 Hz, 1H), 7.19-7.23 (m, 1H), 6.81-6.85 (m, 1H), 3.71 (s, 2H), 3.51-3.54 (m, 4H), 2.49-2.51 (m, 4H).

Example 141

3-[(4-Quinolin-3-ylmethyl-piperazine-1-carbonyl)-amino]-benzoic acid (potassium salt)

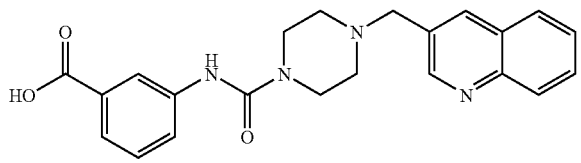 [SMILES: O=C(O)c1cccc(NC(=O)N2CCN(Cc3cnc4ccccc4c3)CC2)c1]

The title compound was prepared from 3-[(4-quinolin-3-ylmethyl-piperazine-1-carbonyl)-amino]-benzoic acid methyl ester in analogy with Example 140. $^1$H NMR (400 MHz, CD$_3$OD): 8.86 (d, J=2.0 Hz, 1H), 8.28 (s, 1H), 7.99 (d, J=8.4 Hz, 1H), 7.92 (d, J=8.2 Hz, 1H), 7.75-7.71 (m, 1H), 7.66 (m, 1H), 7.61-7.56 (m, 2H), 7.53 (d, J=8.0 Hz, 1H), 7.24-7.20 (m, 1H), 3.77 (s, 2H), 3.56-3.53 (m, 4H), 2.56-2.53 (m, 4H).

Example 142

4-Quinolin-3-ylmethyl-piperazine-1-carboxylic acid pyridin-3-ylamide

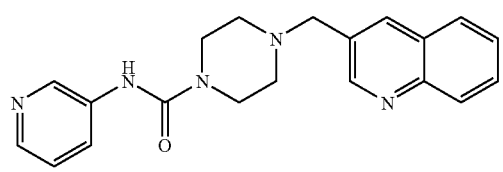 [SMILES: O=C(Nc1cccnc1)N1CCN(Cc2cnc3ccccc3c2)CC1]

A solution of pyridin-3-yl-carbamic acid phenyl ester (0.3 g) and 3-piperazin-1-ylmethyl-quinoline (0.32 g) in DMSO (0.5 mL) was heated in a microwave reactor at 100° C. for 0.5 h. The reaction mixture was partitioned between DCM and water. The combined organic layers were washed with brine (3×), dried (Na$_2$SO$_4$), and concentrated. The residue was purified by column chromatography to yield the title compound as a beige solid (80%). $^1$H NMR (400 MHz, CDCl$_3$): 8.92 (d, J=2.3 Hz, 1H), 8.72 (d, J=2.3 Hz, 1H), 8.28 (d, J=8.1 Hz, 1H), 8.23-8.21 (m, 1H), 8.13-8.10 (m, 2H), 7.84-7.82 (m, 1H), 7.74-7.70 (m, 1H), 7.59-7.55 (m, 1H), 7.37-7.34 (m, 2H), 3.77 (s, 2H), 3.64-3.62 (m, 4H), 2.62-2.59 (m, 4H).

Examples 143-145 were prepared from 3-piperazin-1-ylmethyl-quinoline and the specified phenyl carbamates in analogy with Example 142.

Example 143

4-Quinolin-3-ylmethyl-piperazine-1-carboxylic acid pyridin-2-ylamide

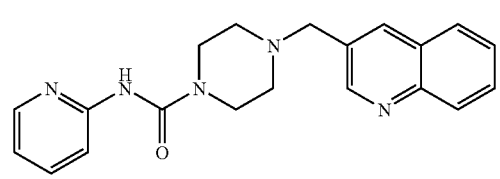 [SMILES: O=C(Nc1ccccn1)N1CCN(Cc2cnc3ccccc3c2)CC1]

The title compound was prepared from pyridin-2-yl-carbamic acid phenyl ester. $^1$H NMR (400 MHz, CDCl$_3$): 8.91 (d, J=2.3 Hz, 1H), 8.18-8.16 (m, 1H), 8.12-8.00 (m, 3H), 7.82-7.80 (m, 1H), 7.73-7.62 (m, 2H), 7.58-7.54 (m, 1H), 6.95-6.92 (m, 1H), 3.73 (s, 2H), 3.57-3.55 (m, 4H), 2.56-2.54 (m, 4H).

Example 144

4-Quinolin-3-ylmethyl-piperazine-1-carboxylic acid pyridin-4-ylamide

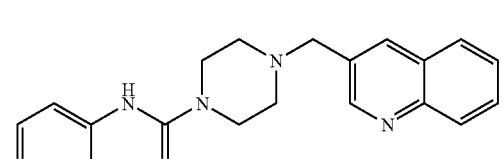

The title compound was prepared from pyridin-4-yl-carbamic acid phenyl ester. $^1$H NMR (400 MHz, CDCl$_3$): 8.88 (d, J=2.3 Hz, 1H), 8.36-8.34 (m, 2H), 8.10-8.05 (m, 2H), 7.82-7.79 (m, 1H), 7.73-7.68 (m, 1H), 7.58-7.54 (m, 1H), 7.40-7.38 (m, 2H), 3.71 (s, 2H), 3.57-3.54 (m, 4H), 2.52-2.49 (m, 4H).

Example 145

4-Quinolin-3-ylmethyl-piperazine-1-carboxylic acid pyrimidin-2-ylamide

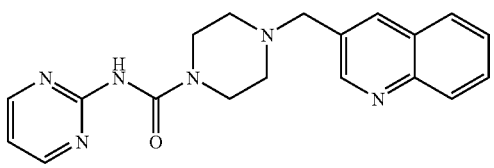 [SMILES: O=C(Nc1ncccn1)N1CCN(Cc2cnc3ccccc3c2)CC1]

Step 1; Pyrimidin-2-yl-carbamic acid phenyl ester. The title compound was prepared in analogy with Example 15 using 2-aminopyrimidine.

Step 2. The title compound was prepared from pyrimidin-2-yl-carbamic acid phenyl ester and 3-piperazin-1-ylmethyl-quinoline in analogy with Example 142. $^1$H NMR (400 MHz, CDCl$_3$): 8.72 (s, 1H), 8.10-8.02 (m, 1H), 8.43-8.41 (m, 2H), 7.69-7.66 (m, 2H), 7.50-7.40 (m, 2H), 6.82-7.70 (m, 1H), 3.81 (s, 2H), 3.42-3.38 (m, 4H), 2.41-2.36 (m, 4H).

Example 146

4-Benzo[1,3]dioxol-5-ylmethyl-piperazine-1-carboxylic acid pyridin-3-ylamide

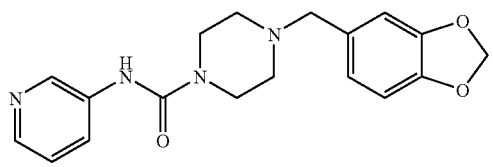 [SMILES: O=C(Nc1cccnc1)N1CCN(Cc2ccc3c(c2)OCO3)CC1]

Step 1; 4-Benzo[1,3]dioxol-5-ylmethyl-piperazine-1-carboxylic acid tert-butyl ester. The title compound was prepared from benzo[1,3]dioxole-5-carbaldehyde in analogy with Example 5.

Step 2; 1-Benzo[1,3]dioxol-5-ylmethyl-piperazine. The title compound was prepared from 4-benzo[1,3]dioxol-5-ylmethyl-piperazine-1-carboxylic acid tert-butyl ester in analogy with Example 6.

Step 3. The title compound was prepared from 1-benzo[1,3]dioxol-5-ylmethyl-piperazine and pyridin-3-yl-carbamic acid phenyl ester in analogy with Example 142. $^1$H NMR (400 MHz, CDCl$_3$): 8.44-8.43 (m, 1H), 8.19-8.17 (m, 1H), 7.98-7.95 (m, 1H), 7.18-7.16 (m, 1H), 6.83-6.80 (m, 2H), 6.70 (s, 1H), 5.89 (s, 2H), 3.55-3.52 (m, 4H), 3.47 (s, 2H), 2.51-2.48 (m, 4H).

Examples 147-149 were prepared in analogy with Example 142.

Example 147

4-Benzo[1,3]dioxol-5-ylmethyl-piperazine-1-carboxylic acid pyridin-4-ylamide

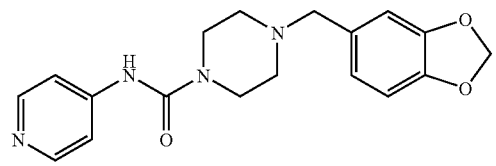 [SMILES: O=C(Nc1ccncc1)N1CCN(Cc2ccc3c(c2)OCO3)CC1]

The title compound was prepared from pyridin-4-yl-carbamic acid phenyl ester and 1-benzo[1,3]dioxol-5-ylmethyl-piperazine. $^1$H NMR (400 MHz, CDCl$_3$): 8.33 (d, J=5.3 Hz, 2H), 7.35-7.34 (m, 2H), 6.79 (s, 1H), 6.68-6.67 (m, 2H), 5.89 (s, 2H), 3.48-3.45 (m, 4H), 3.39 (s, 2H), 2.43-2.40 (m, 4H).

Example 148

4-Benzo[1,3]dioxol-5-ylmethyl-piperazine-1-carboxylic acid pyrimidin-2-ylamide

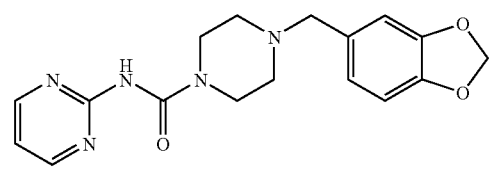

The title compound was prepared from pyrimidin-2-yl-carbamic acid phenyl ester and 1-benzo[1,3]dioxol-5-ylmethyl-piperazine. $^1$H NMR (400 MHz, CDCl$_3$): 8.46 (d, J=5.3 Hz, 2H), 7.31 (br s, 1H), 6.85-6.83 (m, 2H), 6.72-6.68 (m, 2H), 5.89 (s, 2H), 3.56 (br s, 4H), 3.45 (bs, 2H), 2.48 (br s, 4H).

Example 149

4-Benzo[1,3]dioxol-5-ylmethyl-piperazine-1-carboxylic acid pyridin-2-ylamide

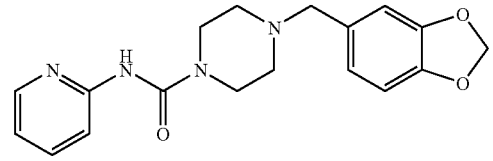

The title compound was prepared from pyridin-2-yl-carbamic acid phenyl ester and 1-benzo[1,3]dioxol-5-ylmethyl-piperazine. $^1$H NMR (400 MHz, CDCl$_3$): 8.18 (d, J=3.9 Hz, 1H), 7.67-7.64 (m, 1H), 6.66-6.64 (m, 2H), 6.54-6.51 (m, 3H), 5.94 (s, 2H), 3.80 (s, 2H), 3.53 (t, J=4.9 Hz, 4H), 2.36 (t, J=4.8 Hz, 4H).

Example 150

4-(2,2-Difluoro-benzo[1,3]dioxol-5-ylmethyl)-piperazine-1-carboxylic acid pyridin-3-ylamide

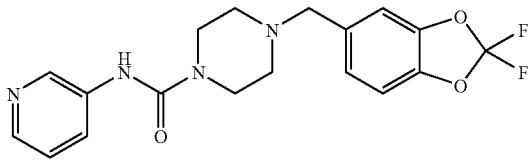 [SMILES: O=C(Nc1cccnc1)N1CCN(Cc2ccc3c(c2)OC(F)(F)O3)CC1]

Step 1; 4-(2,2-Difluoro-benzo[1,3]dioxol-5-ylmethyl)-piperazine-1-carboxylic acid tert-butyl ester. The title compound was prepared from 2,2-difluoro-benzo[1,3]dioxole-5-carbaldehyde in analogy with Example 5.

Step 2; 1-(2,2-Difluoro-benzo[1,3]dioxol-5-ylmethyl)-piperazine. The title compound was prepared from 4-(2,2-difluoro-benzo[1,3]dioxol-5-ylmethyl)-piperazine-1-carboxylic acid tert-butyl ester in analogy with Example 6.

Step 3. The title compound was prepared from pyridin-3-yl-carbamic acid phenyl ester and 1-(2,2-difluoro-benzo[1,3]dioxol-5-ylmethyl)-piperazine in analogy with Example 142. $^1$H NMR (400 MHz, CDCl$_3$): 8.46 (d, J=2.5 Hz, 1H), 8.23-8.21 (m, 1H), 7.99-7.96 (m, 1H), 7.22-7.19 (m, 2H), 7.11 (s, 1H), 6.99-6.98 (m, 2H), 3.54-3.52 (m, 4H), 3.49 (s, 2H), 2.46-2.44 (m, 4H).

Example 151

4-(2,2-Difluoro-benzo[1,3]dioxol-5-ylmethyl)-piperazine-1-carboxylic acid pyridin-4-ylamide

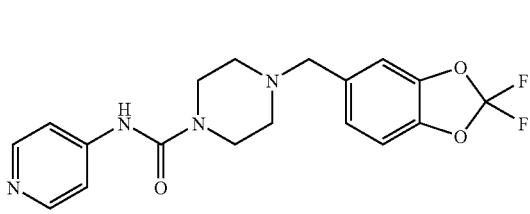 [SMILES: O=C(Nc1ccncc1)N1CCN(Cc2ccc3c(c2)OC(F)(F)O3)CC1]

The title compound was prepared from pyridin-4-yl-carbamic acid phenyl ester and 1-(2,2-difluoro-benzo[1,3]dioxol-5-ylmethyl)-piperazine in analogy with Example 142. $^1$H NMR (400 MHz, CDCl$_3$): 8.36-8.34 (d, J=6.8 Hz, 2H), 7.41-7.39 (d, J=5.8 Hz, 2H), 7.10 (s, 1H), 6.99 (s, 2H), 3.55-3.53 (m, 4H), 3.49 (s, 2H), 2.47-2.44 (m, 4H).

Example 152

4-Quinolin-3-ylmethyl-piperazine-1-carboxylic acid pyrimidin-4-ylamide

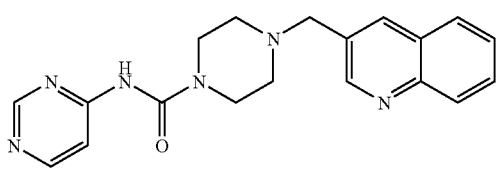 [SMILES: O=C(Nc1ccncn1)N1CCN(Cc2cnc3ccccc3c2)CC1]

Step 1; Pyrimidin-4-yl-carbamic acid phenyl ester. The title compound was prepared from pyrimidin-4-ylamine in analogy with Example 15.

Step 2. The title compound was prepared from pyrimidin-4-yl-carbamic acid phenyl ester and 3-piperazin-1-ylmethyl-quinoline in analogy with Example 142. $^1$H NMR (400 MHz, CDCl$_3$): 8.94 (d, J=2.0 Hz, 1H), 8.76 (s, 1H), 8.54 (d, J=6.1 Hz, 1H), 8.25 (s, 1H), 8.20 (d, J=8.8 Hz, 1H), 7.99 (d, J=5.8 Hz, 1H), 7.87 (d, J=7.8 Hz, 1H), 7.79-7.75 (m, 1H), 7.64-7.60 (m, 1H), 7.38 (br s, 1H), 3.85 (s, 2H), 3.64 (br s, 4H), 2.66 (bs, 4H).

Example 153

4-(2,2-Difluoro-benzo[1,3]dioxol-5-ylmethyl)-piperazine-1-carboxylic acid pyrimidin-4-ylamide

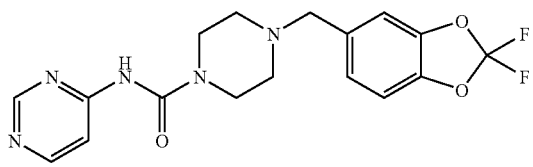

The title compound was prepared from pyrimidin-4-yl-carbamic acid phenyl ester and 1-(2,2-difluoro-benzo[1,3]dioxol-5-ylmethyl)-piperazine in analogy with Example 142. $^1$H NMR (400 MHz, CDCl$_3$): 8.76 (s, 1H), 8.54 (d, J=6.1 Hz, 1H), 7.97 (d, J=5.3 Hz, 1H), 7.65-7.39 (m, 2H), 7.19-7.01 (m, 2H), 4.03-3.55 (m, 6H), 2.91-2.49 (m, 4H).

Example 154

4-(3,4-Dibromo-benzyl)-piperazine-1-carboxylic acid pyrimidin-4-ylamide

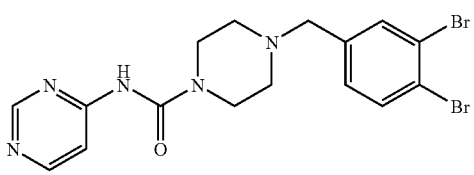

The title compound was prepared from pyrimidin-4-yl-carbamic acid phenyl ester and 1-(3,4-dibromo-benzyl)-piperazine in analogy with Example 142. $^1$H NMR (400 MHz, CDCl$_3$): 8.40 (s, 1H), 8.10-7.80 (m, 1H), 7.70-7.50 (m, 1H), 7.58-7.45 (m, 1H), 7.14-7.10 (m, 1H), 6.55-6.40 (m, 1H), 3.40 (s, 2H), 2.87 (t, J=4.8 Hz, 4H), 2.38 (t, J=4.8 Hz, 4H).

Example 155

4-[(4-Quinolin-3-ylmethyl-piperazine-1-carbonyl)-amino]-benzoic acid

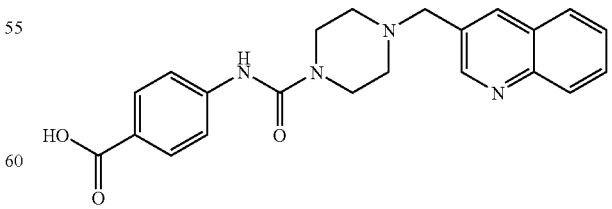

The title compound was prepared from 4-[(4-quinolin-3-ylmethyl-piperazine-1-carbonyl)-amino]-benzoic acid methyl ester in analogy with Example 140. $^1$H NMR (400 MHz, CD$_3$OD): 8.89 (d, J=1.8 Hz, 1H), 8.31 (d, J=1.3 Hz, 1H), 8.03 (d, J=8.8 Hz, 1H), 7.97-7.95 (m, 1H), 7.90-7.87 (m, 2H), 7.79-7.75 (m, 1H), 7.65-7.61 (m, 1H), 7.42-7.40 (m, 2H), 3.81 (s, 2H), 3.60-3.57 (m, 4H), 2.59-2.57 (m, 4H).

Example 156

4-Quinoxalin-2-ylmethyl-piperazine-1-carboxylic acid phenylamide

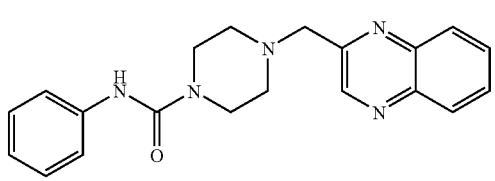 [SMILES: O=C(Nc1ccccc1)N1CCN(Cc2cnc3ccccc3n2)CC1]

The title compound was prepared from piperazine-1-carboxylic acid phenylamide and 2-quinoxaline-carboxaldehyde in analogy with Example 18. ¹H NMR (400 MHz, CDCl₃): 8.96 (s, 1H), 8.06-7.98 (m, 2H), 7.72-7.66 (m, 2H), 7.28-7.16 (m, 4H), 7.96-7.92 (m, 1H), 6.42 (s, 1H), 3.85 (s, 2H), 3.48-3.45 (m, 4H), 3.55-3.52 (m, 4H).

Example 157

4-(3,4-Dichloro-benzyl)-piperazine-1-carboxylic acid phenylamide

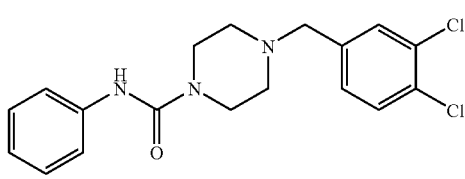 [SMILES: O=C(Nc1ccccc1)N1CCN(Cc2ccc(Cl)c(Cl)c2)CC1]

The title compound was prepared from piperazine-1-carboxylic acid phenylamide and 3,4-dichlorobenzaldehyde in analogy to Example 18. ¹H NMR (400 MHz, CDCl₃): 8.82-8.81 (m, 2H), 7.98-7.96 (m, 2H), 7.65-7.57 (m, 3H), 7.16-7.13 (m, 1H), 3.88-3.81 (m, 4H), 3.50 (s, 2H), 2.60-2.53 (m, 4H).

Example 158

4-Quinolin-3-ylmethyl-piperazine-1-carboxylic acid thiazol-2-ylamide

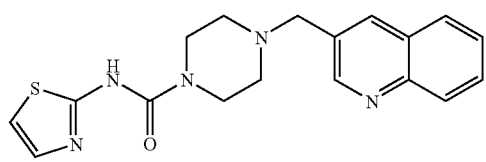 [SMILES: O=C(Nc1nccs1)N1CCN(Cc2cnc3ccccc3c2)CC1]

Step 1; Thiazol-2-yl-carbamic acid phenyl ester. The title compound was prepared in analogy with Example 15 using 2-aminothiazole.

Step 2. The title compound was prepared from thiazol-2-yl-carbamic acid phenyl ester and 3-piperazin-1-ylmethyl-quinoline in analogy with Example 142. ¹H NMR (400 MHz, CDCl₃): 9.03 (d, J=2.0 Hz, 1H), 8.24-8.20 (m, 2H), 7.94 (d, J=8.1 Hz, 1H), 7.86-7.81 (m, 1H), 7.70-7.66 (m, 1H), 7.43 (d, J=3.3 Hz, 1H), 6.98 (d, J=3.5 Hz, 1H), 3.87 (s, 2H), 3.73-3.69 (m, 4H), 2.68 (bs, 4H).

Example 159

4-Benzo[1,3]dioxol-5-ylmethyl-piperazine-1-carboxylic acid thiazol-2-ylamide

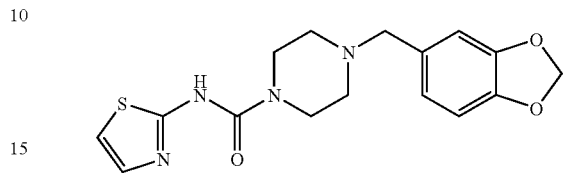

The title compound was prepared from 1-benzo[1,3]dioxol-5-ylmethyl-piperazine and thiazol-2-yl-carbamic acid phenyl ester in analogy with Example 142. ¹H NMR (400 MHz, CDCl₃): 7.30 (d, J=4.0 Hz, 1H), 6.89 (s, 1H), 6.85 (d, J=3.8 Hz, 1H), 6.77 (s, 2H), 5.97 (s, 1H), 5.96 (s, 2H), 3.62 (bs, 4H), 3.53 (s, 2H), 2.54 (bs, 4H).

Example 160

4-(3,4-Dibromo-benzyl)-piperazine-1-carboxylic acid methyl-phenyl-amide

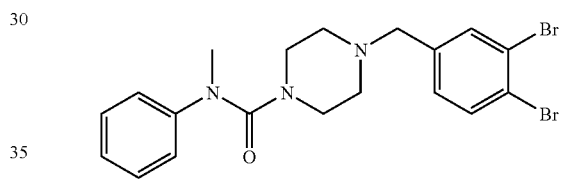

To a solution of 4-(3,4-dibromo-benzyl)-piperazine-1-carboxylic acid phenylamide (0.02 g) in DMF (0.6 mL) was added NaH (60% dispersion in oil; 3 mg) in one portion. The resulting mixture was allowed to stir for 30 min, then was treated with MeI (0.005 mL), and was stirred at rt for 12 h. The mixture was concentrated and the residue was purified by column chromatography (5% MeOH/DCM), giving the product as a white solid (0.015 g). ¹H NMR (400 MHz, CDCl₃): 7.54-7.50 (m, 2H), 7.33-7.31 (m, 2H), 7.12-7.05 (m, 4H), 3.34 (s, 2H), 3.22-3.20 (m, 6H), 2.23-2.21 (m, 4H), 1.63 (s, 3H).

Example 161

4-(5-Bromo-2-hydroxy-3-methoxy-benzyl)-piperazine-1-carboxylic acid phenylamide hydrochloride

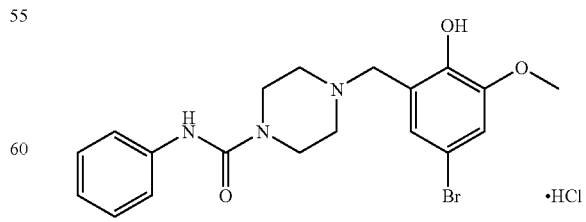

To a solution of 4-(5-bromo-2-hydroxy-3-methoxy-benzyl)-piperazine-1-carboxylic acid phenylamide (1.2 g) in Et₂O (16 mL) was added HCl (2 M in Et₂O, 3.5 mL). After 1 h, the mixture was concentrated to give the title compound as a white solid. ¹H NMR (400 MHz, CD₃OD): 7.40-7.20 (m, 6H), 7.10-7.05 (m, 1H), 4.37 (s, 2H), 3.94 (s, 3H).

The compounds in Examples 162-163 were prepared in analogy with Example 161.

Example 162

4-(3,4-Dibromo-benzyl)-piperazine-1-carboxylic acid phenylamide hydrochloride

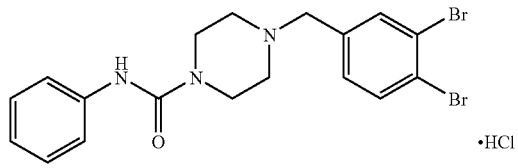 [SMILES: O=C(Nc1ccccc1)N1CCN(Cc2ccc(Br)c(Br)c2)CC1 ; Cl]

¹H NMR (400 MHz, CD₃OD): 7.93 (d, J=2.0 Hz, 1H), 7.85 (d, J=8.1 Hz, 1H), 7.45-7.42 (m, 1H), 7.73-7.34 (m, 2H), 7.30-7.25 (m, 2H), 7.07-7.02 (m, 1H), 4.30 (br s, 2H), 3.55-3.10 (br m, 8H).

Example 163

4-Quinolin-2-ylmethyl-piperazine-1-carboxylic acid phenylamide dihydrochloride

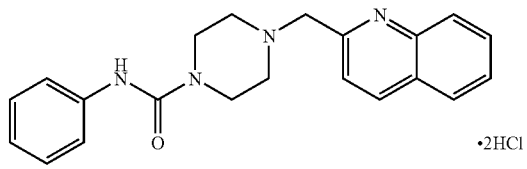 [SMILES: O=C(Nc1ccccc1)N1CCN(Cc2ccc3ccccc3n2)CC1 ; "·2HCl"]

¹H NMR (400 MHz, CD₃OD): 8.73 (s, 1H), 8.42 (d, J=8.4 Hz, 2H), 8.01-7.94 (m, 2H), 7.77-7.72 (m, 1.2H), 7.65-7.56 (m, 2H), 7.36-7.32 (m, 2H), 7.16-7.10 (m, 2H), 6.87-6.82 (m, 1H), 4.63 (s, 2H), 3.70 (br s, 4H).

The following compounds in Examples 164-167 may be prepared using methods analogous to those described in the preceding examples.

Example 164

4-(2-Methoxy-benzyl)-piperazine-1-carboxylic acid phenylamide

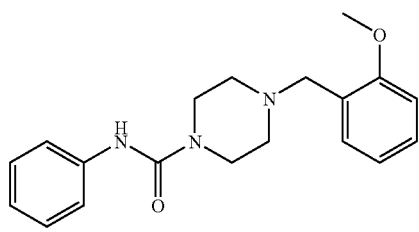 [SMILES: COc1ccccc1CN1CCN(C(=O)Nc2ccccc2)CC1]

Example 165

4-Benzofuran-2-ylmethyl-piperazine-1-carboxylic acid phenylamide

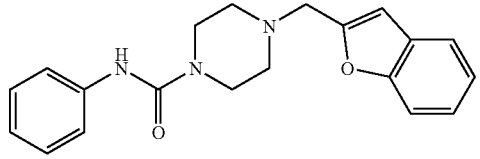

Example 166

4-(3,4-Dibromo-benzyl)-piperazine-1-carboxylic acid (4-nitro-phenyl)-amide

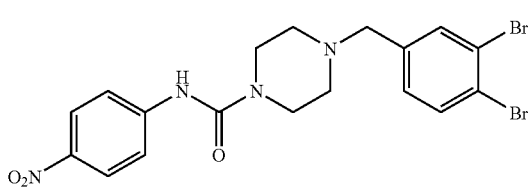 [SMILES: O=C(Nc1ccc([N+](=O)[O-])cc1)N1CCN(Cc2ccc(Br)c(Br)c2)CC1]

Example 167

4-(3,4-Dibromo-benzyl)-piperazine-1-carboxylic acid (4-trifluoromethyl-phenyl)-amide

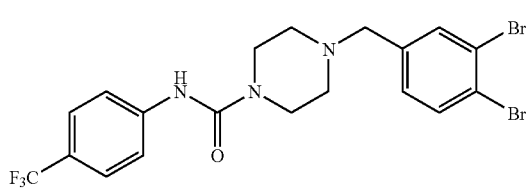 [SMILES: O=C(Nc1ccc(C(F)(F)F)cc1)N1CCN(Cc2ccc(Br)c(Br)c2)CC1]

The title compounds per se of Examples A through J are known and may be obtained from commercial sources. The compounds described in Examples K and L are provided for comparative purposes. All compounds in Examples A through L were prepared according to the general procedures described above.

Example A 4-(3-Iodo-benzyl)-piperazine-1-carboxylic acid phenylamide

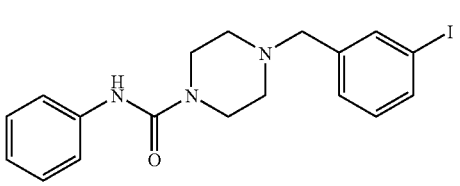 [SMILES: O=C(Nc1ccccc1)N1CCN(Cc2cccc(I)c2)CC1]

The title compound was prepared from piperazine-1-carboxylic acid phenylamide and 3-iodobenzaldehyde. ¹H NMR (400 MHz, CDCl$_3$): 7.71 (s, 1H), 7.62-7.60 (m, 1H), 7.36-7.26 (m, 5H), 7.09-7.01 (m, 2H), 6.33 (s, 1H), 3.52-3.48 (m, 6H), 2.49-2.46 (m, 4H).

Example B

4-Benzo[1,3]dioxol-5-ylmethyl-piperazine-1-carboxylic acid phenylamide

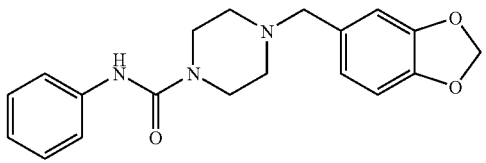 [SMILES: O=C(Nc1ccccc1)N1CCN(Cc2ccc3c(c2)OCO3)CC1]

The title compound was prepared from piperazine-1-carboxylic acid phenylamide and benzo[1,3]dioxole-5-carbaldehyde. $^1$H NMR (400 MHz, CDCl$_3$): 7.36-7.24 (m, 4H), 7.05-6.99 (m, 1H), 6.86 (br s, 1H), 6.77-6.72 (m, 2H), 6.43 (br s, 1H), 5.95 (s, 2H), 3.50-3.46 (m, 4H), 3.43 (s, 2H), 2.46-2.42 (m, 4H).

Example B1

The hydrochloride salt of the title compound was prepared in analogy with Example 161. $^1$H NMR (400 MHz, CD$_3$OD): 7.37-7.27 (m, 4H), 7.09-7.00 (m, 3H), 6.90 (d, J=7.8 Hz, 1H), 6.05 (s, 2H), 4.40-4.26 (br m, 2H), 4.25 (s, 2H), 3.50-3.38 (br m, 4H), 3.10-3.00 (br m, 2H).

Example C 4-(3-Bromo-benzyl)-piperazine-1-carboxylic acid phenylamide

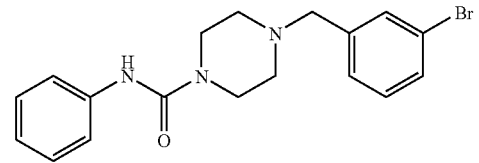 [SMILES: O=C(Nc1ccccc1)N1CCN(Cc2cccc(Br)c2)CC1]

The title compound was prepared from piperazine-1-carboxylic acid phenylamide and 3-bromobenzaldehyde. $^1$H NMR (400 MHz, CDCl$_3$): 7.50 (br s, 1H), 7.43-7.17 (m, 7H), 7.05-7.00 (m, 1H), 6.47 (br s, 1H), 3.52-3.45 (m, 6H), 2.48-2.42 (m, 4H).

Example D 4-(3,4-Dimethyl-benzyl)-piperazine-1-carboxylic acid phenylamide

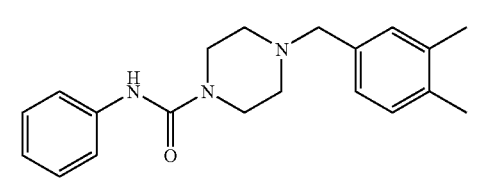 [SMILES: Cc1ccc(CN2CCN(C(=O)Nc3ccccc3)CC2)cc1C]

The title compound was prepared from piperazine-1-carboxylic acid phenylamide and 3,4-dimethylbenzaldehyde. $^1$H NMR (400 MHz, CDCl$_3$): 7.35-7.26 (m, 4H), 7.11-7.00 (m, 4H), 6.31 (s, 1H), 3.51-3.48 (m, 6H), 2.49-2.26 (m, 4H), 2.26 (d, J=3.8 Hz, 6H).

Example E 4-(4-Methyl-benzyl)-piperazine-1-carboxylic acid phenylamide

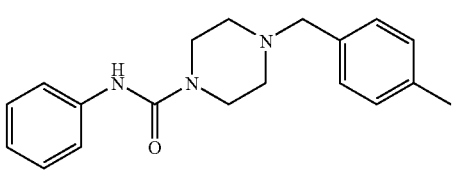 [SMILES: Cc1ccc(CN2CCN(C(=O)Nc3ccccc3)CC2)cc1]

The title compound was prepared from piperazine-1-carboxylic acid phenylamide and 4-methylbenzaldehyde. $^1$H NMR (400 MHz, CDCl$_3$): 7.35-7.00 (m, 9H), 6.32 (s, 1H), 3.50-3.48 (m, 6H), 2.49-2.46 (m, 4H), 2.35 (s, 3H).

Example F

4-Phenethyl-piperazine-1-carboxylic acid phenylamide

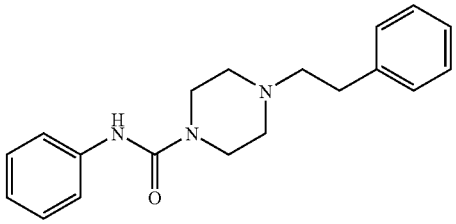 [SMILES: O=C(Nc1ccccc1)N1CCN(CCc2ccccc2)CC1]

The title compound was prepared from piperazine-1-carboxylic acid phenylamide and phenylacetaldehyde. $^1$H NMR (400 MHz, CDCl$_3$): 7.37-7.19 (m, 9H), 7.06-7.02 (m, 1H), 6.31 (s, 1H), 3.55-3.53 (m, 4H), 2.85-2.81 (m, 2H), 2.67-2.56 (m, 6H).

Example G

4-Benzo[1,3]dioxol-5-ylmethyl-piperazine-1-carboxylic acid (4-fluoro-phenyl)-amide

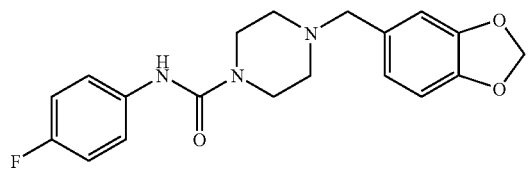 [SMILES: O=C(Nc1ccc(F)cc1)N1CCN(Cc2ccc3c(c2)OCO3)CC1]

The title compound was prepared from piperazine-1-carboxylic acid (4-fluoro-phenyl)-amide and piperonal. $^1$H NMR (400 MHz, CDCl$_3$): 7.29-7.24 (m, 2H), 6.98-6.92 (m, 2H), 6.85 (s, 1H), 6.77-6.71 (m, 2H), 6.56 (s, 1H), 5.95 (s, 2H), 3.50-3.45 (m, 6H), 2.45 (t, J=5.1 Hz, 4H).

Example H

4-Benzyl-piperidine-1-carboxylic acid phenylamide

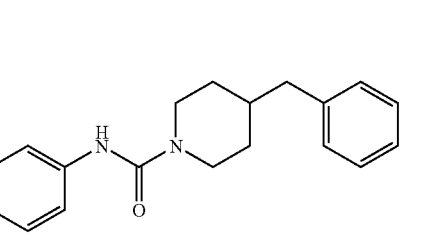

The title compound was prepared from 4-benzylpiperidine and phenyl isocyanate. $^1$H NMR (400 MHz, CDCl$_3$): 7.35-7.10 (m, 9H), 7.02-6.97 (m, 1H), 6.50 (br s, 1H), 4.07-4.00 (m, 2H), 2.77 (td, J=13, 2.4 Hz, 2H), 2.54 (d, J=6.8 Hz, 2H), 1.76-1.64 (m, 3H), 1.28-1.15 (m, 2H).

Example I 4-(3-Phenyl-propyl)-piperazine-1-carboxylic acid phenylamide

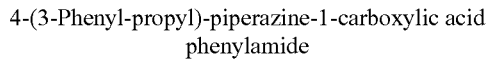

The title compound was prepared from piperazine-1-carboxylic acid phenylamide and 3-phenylpropionaldehyde. $^1$H NMR (400 MHz, CDCl$_3$): 7.36-7.16 (m, 9H), 7.05-7.00 (m, 1H), 6.40 (br s, 1H), 3.52-3.47 (m, 4H), 2.65 (t, J=7.6 Hz, 2H), 2.47-2.38 (m, 4H), 2.39 (t, J=7.4 Hz, 2H), 1.88-1.79 (m, 2H).

Example J

4-Benzyl-piperazine-1-carboxylic acid phenylamide

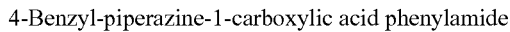

The title compound was prepared from 1-benzylpiperazine and phenyl isocyanate. $^1$H NMR (400 MHz, CDCl$_3$): 7.35-7.22 (m, 9H), 7.02-6.97 (m, 1H), 6.55 (br s, 1H), 3.56 (s, 2H), 3.48-3.45 (m, 4H), 2.45-2.41 (m, 4H).

Example K 4-(2-Benzyloxy-benzyl)-piperazine-1-carboxylic acid phenylamide

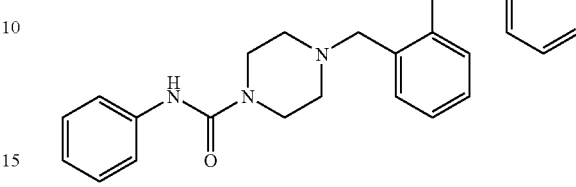

The title compound was prepared from piperazine-1-carboxylic acid phenylamide and 2-benzyloxybenzaldehyde. $^1$H NMR (400 MHz, CDCl$_3$): 7.49-7.20 (m, 11H), 7.05-6.92 (m, 3H), 6.41 (s, 1H), 5.08 (s, 2H), 3.65 (s, 2H), 3.51-3.45 (m, 4H), 2.55-2.49 (m, 4H).

Example L 4-(6-Bromo-1,2,3,4-tetrahydro-naphthalen-2-yl)-piperazine-1-carboxylic acid phenylamide

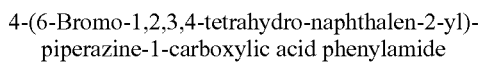

The title compound was prepared from piperazine-1-carboxylic acid phenylamide and 6-bromo-3,4-dihydro-1H-naphthalen-2-one. $^1$H NMR (400 MHz, CDCl$_3$): 7.37-7.21 (m, 6H), 7.06-7.02 (m, 1H), 6.96-6.94 (m, 1H), 6.33 (s, 1H), 3.55-3.53 (m, 4H), 2.94-2.64 (m, 9H), 2.12-2.08 (m, 1H), 1.69-1.61 (m, 1H).

Biological Methods

Assay Method 1

T84 frozen pellets (contents of 1-4×15 cm culture dishes) were homogenized in 300 mL of FAAH assay buffer (125 mM Tris, 1 mM EDTA, 0.2% glycerol, 0.02% Triton X-100, 0.4 mM Hepes, pH 9). The assay mixture was prepared from 50 μL of the cell homogenate, 10 μL of the test compound, and 40 μL of anandamide [1-$^3$H-ethanolamine] ($^3$H-AEA; Perkin-Elmer, 10.3 C$_i$/mmol), which was added last, for a final tracer concentration of 200 nM. The reaction mixture was incubated at rt for 1 hour (h). During the incubation, 96-well Multiscreen filter plates (catalog number MAFC-NOB50; Millipore, Bedford, Mass., USA) were loaded with 25 μL of activated charcoal (Multiscreen column loader, catalog number MACL09625, Millipore) and washed once with 100 μL of MeOH. Also during the incubation, 96-well DYNEX MicroLite plates (catalog number NL510410) were loaded with 100 μL of MicroScint40 (catalog number 6013641, Packard Bioscience, Meriden, Conn., USA). After the 1 h incubation, 60 μL of the reaction mixture were transferred to the charcoal plates, which were then assembled on top of the DYNEX plates using Centrifuge Alignment Frames (catalog number MACF09604, Millipore). The unbound, labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 1.

TABLE 1

| Ex. | $IC_{50}$ (nM) |
|---|---|
| 18 | 17 |
| 19 | 19 |
| 20 | 19 |
| 21 | 31 |
| 22 | 26 |
| 23 | 73 |
| 24 | 52 |
| 25 | 57 |
| 26 | 79 |
| 27 | 69 |
| 28 | 80 |
| 29 | 120 |
| 30 | 180 |
| 31 | 200 |
| 32 | 220 |
| 33 | 280 |
| 34 | 290 |
| 35 | 460 |
| 36 | 470 |
| 37 | 590 |
| 38 | 620 |
| 39 | 1100 |
| 40 | 1100 |
| 41 | 1300 |
| 42 | 2000 |
| 43 | 4000 |
| 44 | 4000 |
| 45 | >10000 |
| 46 | >10000 |
| 47 | >10000 |
| 48 | 3500 |
| 49 | 4500 |
| 50 | 3000 |
| 51 | 6000 |
| 52 | 87 |
| 53 | 230 |
| 54 | 170 |
| 55 | 28 |
| 56 | 9000 |
| 57 | 54 |
| 58 | 100 |
| 59 | 21 |
| 60 | 9 |
| 61 | 20 |
| 62 | 18 |
| 63 | 69 |
| 64 | 220 |
| 65 | 9 |
| 66 | 1600 |
| 67 | 8000 |
| 68 | 95 |
| 69 | 23 |
| 70 | 410 |
| 71 | 6000 |
| 72 | 110 |
| 73 | 29 |
| 74 | 2000 |
| 75 | 24 |
| 76 | 350 |
| 77 | 32 |
| 78 | 5000 |
| 79 | 8000 |
| 80 | 330 |
| 81 | 6000 |

TABLE 1-continued

| Ex. | $IC_{50}$ (nM) |
|---|---|
| 82 | 80 |
| 83 | 480 |
| 84 | 2500 |
| 85 | 19 |
| 86 | 21 |
| 87 | 48 |
| 88 | 100 |
| 89 | 22 |
| 90 | 75 |
| 91 | 130 |
| 92 | 240 |
| 93 | 460 |
| 94 | 470 |
| 95 | 500 |
| 96 | >10000 |
| 97 | 120 |
| 98 | 130 |
| 99 | 1600 |
| 100 | 200 |
| 101 | 360 |
| 102 | 540 |
| 103 | 6000 |
| 104 | 690 |
| 108 | 270 |
| 109 | 200 |
| 110 | 200 |
| 111 | 250 |
| 112 | 61 |
| 113 | 8000 |
| 114 | 2300 |
| 115 | 4000 |
| 116 | 240 |
| 117 | 360 |
| 118 | 27 |
| 119 | 1000 |
| 120 | 170 |
| 121 | 210 |
| 122 | 220 |
| 123 | 1500 |
| 124 | 1800 |
| 125 | 10000 |
| 126 | 2000 |
| 127 | 2000 |
| 128 | 2000 |
| 129 | 2000 |
| 130 | 160 |
| 131 | 33 |
| 132 | 3000 |
| 133 | 50 |
| 134 | 65 |
| 135 | 83 |
| 136 | 67 |
| 137 | 1000 |
| 138 | 59 |
| 139 | 380 |
| 161 | 210 |
| 162 | 38 |
| 163 | 23 |
| A | 120 |
| B | 350 |
| B1 | 1200 |
| C | 280 |
| D | 630 |
| E | 1300 |
| F | >10000 |
| G | 1600 |
| H | 270 |
| I | 1700 |
| J | 2000 |
| K | >10000 |
| L | 370 |

Assay Method 2

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled human FAAH cDNA (1 µg) was added to the cells and mixed. The voltage for the electroporation was set at 0.25 kV, and the capacitance was set at 960 µF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-$^3$H-ethanolamine] ($^3$H-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 2.

TABLE 2

| Ex. | $IC_{50}$ (nM) |
|---|---|
| 18 | 23 |
| 21 | 19 |
| 32 | 380 |
| 34 | 330 |
| 41 | 3000 |
| 52 | 100 |
| 59 | 16 |
| 98 | 220 |
| 105 | >10000 |
| 106 | 230 |
| 107 | 650 |
| 140 | >10000 |

TABLE 2-continued

| Ex. | $IC_{50}$ (nM) |
|---|---|
| 141 | 5000 |
| 142 | 4100 |
| 143 | 1800 |
| 144 | 2000 |
| 145 | 8000 |
| 146 | 380 |
| 147 | 3000 |
| 148 | >10000 |
| 149 | 4000 |
| 150 | 130 |
| 151 | 1700 |
| 152 | 4000 |
| 153 | 1000 |
| 154 | 282 |
| 155 | 8000 |
| 156 | 840 |
| 157 | 65 |
| 158 | >10000 |
| 159 | >10000 |
| 160 | >10000 |

Assay Method 3

A. Transfection of Cells with Rat FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled rat FAAH cDNA (1 µg) was added to the cells and mixed. The voltage for the electroporation was set at 0.25 kV, and the capacitance was set at 960 µF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-$^3$H-ethanolamine] ($^3$H-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount. Results for compounds tested in this assay are presented in Table 3.

TABLE 3

| Ex. | IC$_{50}$ (nM) |
|---|---|
| 18 | 265 |
| 19 | 350 |
| 21 | 180 |
| 22 | 1400 |
| 26 | 130 |
| 32 | 10000 |
| 34 | 410 |
| 41 | 10000 |
| 52 | 290 |
| 57 | 430 |
| 59 | 50 |
| 68 | 610 |
| 98 | 6500 |
| 105 | 10000 |
| 106 | 2000 |
| 107 | 8000 |
| 111 | 2000 |
| 112 | 370 |
| 140 | 10000 |
| 141 | 8000 |
| 142 | 4000 |
| 143 | 8000 |
| 144 | 10000 |
| 145 | 10000 |
| 146 | 6500 |
| 147 | 10000 |
| 148 | 10000 |
| 149 | 10000 |
| 150 | 290 |
| 151 | 2000 |
| 152 | 10000 |
| 153 | 60000 |
| 154 | 2000 |
| 155 | 10000 |
| 156 | 8000 |
| 157 | 350 |
| 158 | 10000 |
| 159 | 10000 |
| 160 | 10000 |
| 162 | 270 |
| B | 8000 |
| G | 10000 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:
1. A compound of Formula (I):

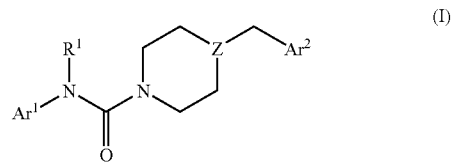

wherein:
Z is —N— or >CH;
$R^1$ is —H or —C$_{1-4}$alkyl;
Ar$^1$ is 2-thiazolyl, 2-pyridyl, 3-pyridyl, 4-pyridyl, 2-pyrimidinyl, 4-pyrimidinyl, 5-pyrimidinyl, each unsubstituted or substituted at a carbon ring member with one or two R$^a$ moieties;
where each R$^a$ moiety is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are each independently —H or —C$_{1-4}$alkyl; and
Ar$^2$ is:
(a) unsubstituted 1-naphthyl; or a phenanthrenyl, pyrenyl, fluorenyl, 2-naphthyl, or N—R$^d$-9H-carbazolyl moiety, wherein R$^d$ is selected from the group consisting of —H, —C$_{1-4}$alkyl, and phenyl, each said moiety unsubstituted or substituted with one, two, or three R$^e$ substituents, wherein each R$^e$ substituent is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined;
(b) phenyl fused at two adjacent ring carbon atoms to a group selected from the group consisting of —(CH$_2$)$_{3-5}$— having 0 or 1 double bonds, —OCH$_2$CH$_2$O—, and —OCF$_2$O— to form a fused ring structure; or phenyl substituted on adjacent ring carbon atoms with —OCH$_2$O— to form 4-benzo[1,3]dioxolyl; each phenyl moiety further unsubstituted or substituted with one, two, or three R$^e$ substituents as previously defined;
(c) Ar$^6$, where Ar$^6$ is a 6-membered monocyclic heteroaryl having carbon as a point of attachment, with one or two nitrogen heteroatoms, unsubstituted or substituted with one, two, or three R$^e$ substituents as previously defined;
(d) a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two, or three R$^e$ substituents as previously defined;
(e) phenyl substituted at the 3- or 4-position with R$^g$, and optionally further substituted with one, two, or three substituents R$^h$,
wherein each R$^g$ is independently selected from the group consisting of —C$_{2-8}$alkyl, —C$_{2-8}$alkenyl, —OC$_{3-8}$cycloalkyl, —OC$_{3-8}$heterocycloalkyl, and —O—C$_{2-10}$ alkyl optionally substituted with —NR$^i$R$^j$, wherein R$^i$ and R$^j$ are each independently —H or —C$_{1-8}$alkyl, or R$^i$ and R$^j$ are taken together with the nitrogen ring atom of attachment to form a 5-, 6-, or 7-membered heterocycloalkyl ring optionally having one additional carbon ring atom replaced with O, S, >NH, or >NC$_{1-4}$alkyl; and each R$^h$ substituent is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined;

(f) phenyl substituted at the 3- or 4-position with -L-Ar$^3$, wherein:

L is a linker selected from the group consisting of —(CH$_2$)$_{1-3}$—, —CH=CH—, —O—, —OCH$_2$—, —CH$_2$O—, —NH—, >NC$_{1-4}$alkyl, >S(=O)$_{0-2}$, —OSO$_2$—, —C≡C—, —C(=O)—, and a covalent bond; and Ar$^3$ is a moiety selected from the group consisting of:
(1) phenyl, naphthyl, and phenanthrenyl,
(2) Ar$^{6'}$, where Ar$^{6'}$ is a 6-membered monocyclic heteroaryl having carbon as a point of attachment, having one or two nitrogen heteroatoms,
(3) Ar$^{5'}$, where Ar$^{5'}$ is a 5-membered monocyclic heteroaryl having carbon as a point of attachment, with one heteroatom selected from the group consisting of O, S, >NH, and >NR$^f$, wherein R$^f$ is —C$_{1-8}$alkyl or —C$_{0-3}$phenalkyl, and having zero, one, two, or three additional nitrogen heteroatoms, and
(4) a 9- or 10-membered fused bicyclic heteroaryl, having one heteroatom selected from the group consisting of N, O, and S, with a carbon as point of ring attachment, and optionally having up to four additional carbon ring atoms replaced with nitrogen, said fused bicyclic heteroaryl having not more than five heteroatoms;

where each of the moieties (1) through (4) is optionally di-substituted on adjacent carbons with —OC$_{1-4}$alkyleneO—, —(CH$_2$)$_{2-3}$NH—, —(CH$_2$)$_{1-2}$NH(CH$_2$)—, —(CH$_2$)$_{2-3}$N(C$_{1-4}$alkyl)-, or —(CH$_2$)$_{1-2}$N(C$_{1-4}$alkyl)(CH$_2$)— to form a fused ring structure, and is optionally further substituted with one, two, or three substituents R$^k$, wherein each R$^k$ substituent is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined;

(g) 2-hydroxyphenyl or 2-methoxyphenyl, unsubstituted or substituted with one, two, or three substituents R$^l$, wherein each R$^l$ substituent is independently selected from the group consisting of —CH$_3$, 6-C$_{2-4}$alkyl, 6-C$_{2-4}$alkenyl, —OH, —OCH$_3$, 6-OC$_{2-6}$alkyl, halo, —CF$_3$, —OCF$_3$, —SCF$_3$, —SH, —SC$_{1-4}$alkyl, —SO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined;

(h) 4-halophenyl, unsubstituted or substituted with one, two, or three substituents R$^m$, wherein each R$^m$ substituent is independently selected from the group consisting of —CH$_3$, 2-C$_{2-4}$alkyl, 2-C$_{2-4}$alkenyl, 3-hydroxy, 4-hydroxy, —OCH$_3$, 2-OC$_{2-6}$alkyl, halo, —CF$_3$, —OCF$_3$, —SCF$_3$, —SH, —SC$_{1-4}$alkyl, —SO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined; or (i) 2-bromophenyl, 3-methylphenyl, 3-methoxyphenyl, 4-methoxyphenyl, or 3,4-dimethoxyphenyl;

or a pharmaceutically acceptable salt of such compound.

2. A compound as defined in claim 1, wherein R$^1$ is —H.

3. A compound as defined in claim 1, wherein Ar$^2$ is 2-methoxyphenyl, unsubstituted or substituted with one, two, or three substituents R$^l$.

4. A compound as defined in claim 1, wherein Ar$^1$ is 2-pyridyl, 3-pyridyl or 4-pyridyl.

5. A compound as defined in claim 1, wherein:

Z is —N— or >CH;

R$^1$ is —H or —C$_{1-4}$alkyl;

Ar$^1$ is 2-pyridyl, 3-pyridyl, 4-pyridyl, 2-pyrimidinyl, 4-pyrimidinyl, 5-pyrimidinyl, each unsubstituted or substituted at a carbon ring member with one or two R$^a$ moieties;

where each R$^a$ moiety is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are each independently —H or —C$_{1-4}$alkyl; and Ar$^2$ is:

(a) unsubstituted 1-naphthyl; or phenanthrenyl, pyrenyl, fluorenyl, 2-naphthyl, or N—R$^d$-9H-carbazolyl moieties, wherein R$^d$ is selected from the group consisting of —H, —C$_{1-4}$alkyl, and phenyl, each said moiety unsubstituted or substituted with one, two, or three R$^e$ substituents, wherein each R$^e$ substituent is independently selected from the group consisting of —C$_{1-4}$alkyl, —C$_{2-4}$alkenyl, —OH, —OC$_{1-4}$alkyl, halo, —CF$_3$, —OCF$_3$, —SCF$_3$, —SH, —S(O)$_{0-2}$C$_{1-4}$alkyl, —OSO$_2$C$_{1-4}$alkyl, —CO$_2$C$_{1-4}$alkyl, —CO$_2$H, —COC$_{1-4}$alkyl, —N(R$^b$)R$^c$, —SO$_2$NR$^b$R$^c$, —NR$^b$SO$_2$R$^c$, —C(=O)NR$^b$R$^c$, —NO$_2$, and —CN, wherein R$^b$ and R$^c$ are as previously defined;

(b) phenyl fused at two adjacent ring carbon atoms to a group selected from the group consisting of —(CH$_2$)$_{3-5}$— having 0 or 1 double bonds, —OCH$_2$CH$_2$O—, and —OCF$_2$O— to form a fused ring structure; or phenyl substituted on adjacent ring carbon atoms with —OCH$_2$O— to form 4-benzo[1,3]dioxolyl; each phenyl moiety further unsubstituted or substituted with one, two, or three R$^e$ substituents as previously defined;

(c) Ar$^6$, where Ar$^6$ is a 6-membered monocyclic heteroaryl having carbon as a point of attachment, with one or two nitrogen heteroatoms, unsubstituted or substituted with one, two, or three R$^e$ substituents as previously defined;

(d) a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two, or three $R^e$ substituents as previously defined;

(e) phenyl substituted at the 3- or 4-position with $R^g$, and optionally further substituted with one, two, or three substituents $R^h$, wherein each $R^g$ is independently selected from the group consisting of —$C_{2-8}$alkyl, —$C_{2-8}$alkenyl, —$OC_{3-8}$cycloalkyl, —$OC_{3-8}$heterocycloalkyl, and —O—$C_{2-10}$alkyl optionally substituted with —$NR^iR^j$, wherein $R^i$ and $R^j$ are each independently —H or —$C_{1-8}$alkyl, or $R^i$ and $R^j$ are taken together with the nitrogen ring atom of attachment to form a 5-, 6-, or 7-membered heterocycloalkyl ring optionally having one additional carbon ring atom replaced with O, S, >NH, or >$NC_{1-4}$alkyl; and each $R^h$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(f) phenyl substituted at the 3- or 4-position with -L-$Ar^3$, wherein:

L is a linker selected from the group consisting of —$(CH_2)_{1-3}$—, —CH=CH—, —O—, —$OCH_2$—, —$CH_2O$—, —NH—, >$NC_{1-4}$alkyl, >$S(=O)_{0-2}$, —$OSO_2$—, —C≡C—, —C(=O)—, and a covalent bond; and $Ar^3$ is a moiety selected from the group consisting of:
  (1) phenyl, naphthyl, and phenanthrenyl,
  (2) $Ar^{6'}$, where $Ar^{6'}$ is a 6-membered monocyclic heteroaryl having carbon as a point of attachment, having one or two nitrogen heteroatoms,
  (3) $Ar^{5'}$, where $Ar^{5'}$ is a 5-membered monocyclic heteroaryl having carbon as a point of attachment, with one heteroatom selected from the group consisting of O, S, >NH, and >$NR^f$, wherein $R^f$ is —$C_{1-8}$alkyl or —$C_{0-3}$-phenalkyl, and having zero, one, two, or three additional nitrogen heteroatoms, and
  (4) a 9- or 10-membered fused bicyclic heteroaryl, having one heteroatom selected from the group consisting of N, O, and S, with a carbon as point of ring attachment, and optionally having up to four additional carbon ring atoms replaced with nitrogen, said fused bicyclic heteroaryl having not more than five heteroatoms;

where each of the moieties (1) through (4) is optionally di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$-, or —$(CH_2)_{1-2}N(C_{1-4}alkyl)(CH_2)$— to form a fused ring structure, and is optionally further substituted with one, two, or three substituents $R^k$, wherein each $R^k$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(g) 2-hydroxyphenyl, unsubstituted or substituted with one, two, or three substituents $R^l$, wherein each $R^l$ substituent is independently selected from the group consisting of —$CH_3$, 6-$C_{2-4}$alkyl, 6-$C_{2-4}$alkenyl, —OH, —$OCH_3$, 6-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;

(h) 4-halophenyl, unsubstituted or substituted with one, two, or three substituents $R^m$, wherein each $R^m$ substituent is independently selected from the group consisting of —$CH_3$, 2-$C_{2-4}$alkyl, 2-$C_{2-4}$alkenyl, 3-hydroxy, 4-hydroxy, —$OCH_3$, 2-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined; or (i) 2-bromophenyl, 3-methylphenyl, 3-methoxyphenyl, 4-methoxyphenyl, or 3,4-dimethoxyphenyl;

or a pharmaceutically acceptable salt of such compound.

6. A compound as defined in claim 5, wherein Z is —N—.

7. A compound as defined in claim 6, wherein $R^1$ is —H.

8. A compound as defined in claim 6, wherein $Ar^2$ is phenanthren-9-yl, pyren-1-yl, 9H-fluoren-2-yl, 1-naphthyl, 2-naphthyl, 1-hydroxynaphthalen-2-yl, 6-methoxynaphthalen-2-yl, or 9-ethyl-9H-carbazol-3-yl, each unsubstituted or substituted with one, two, or three $R^e$ substituents as previously defined.

9. A compound as defined in claim 6, wherein $Ar^2$ is indanyl, indenyl, tetrahydronaphthyl, 2,3-dihydro-benzofuranyl, chromanyl, 2,3-dihydro-benzo[1,4]dioxinyl, or 2,2-difluoro-benzo[1,3]dioxolyl, each unsubstituted or substituted with one, two, or three $R^e$ substituents as previously defined.

10. A compound as defined in claim 6, wherein $Ar^2$ is phenyl-1H-pyrrolyl, 2-pyridyl, 3-pyridyl, 4-pyridyl, or 6-bromo-pyridin-2-yl, each unsubstituted or substituted with one, two, or three $R^e$ substituents as previously defined.

11. A compound as defined in claim 6, wherein $Ar^2$ is phenyl substituted at the 3- or 4-position with -L-$Ar^3$, where L is —CH=CH—, —O—, —$OCH_2$—, —$SO_2$—, —$OSO_2$—, or a covalent bond.

12. A compound as defined in claim 6, wherein $Ar^2$ is 2-hydroxyphenyl, 5-bromo-2-hydroxy-3-methoxyphenyl, or 5-bromo-2-hydroxyphenyl.

13. A compound as defined in claim 7, wherein $Ar^1$ is 2-pyridyl, 3-pyridyl, 4-pyridyl, 2-pyrimidinyl, or 4-pyrimidinyl, each unsubstituted or substituted at a carbon ring atom with one or two $R^a$ moieties as previously defined.

14. A compound as defined in claim 7, wherein $Ar^2$ is unsubstituted 2,2-difluoro-benzo[1,3]dioxolyl.

15. A compound as defined in claim 7, wherein $Ar^2$ is unsubstituted 4-benzo[1,3]dioxolyl.

16. A compound as defined in claim 7, wherein $Ar^2$ is 2-indolyl, 3-indolyl, 2-quinolinyl, 3-quinolinyl, or 2-quinoxalinyl, each unsubstituted or substituted with one, two, or three $R^e$ substituents as previously defined.

17. A compound as defined in claim 7, wherein $Ar^2$ is 2-quinolinyl or 3-quinolinyl.

18. A compound as defined in claim 7, wherein $Ar^2$ is 4-ethylphenyl, 4-isopropylphenyl, 3-vinylphenyl, 3-ethoxyphenyl, 4-ethoxyphenyl, 3-propoxyphenyl, 4-propoxyphenyl, 3-isobutoxyphenyl, 4-isopropoxyphenyl, 3-isobutoxyphenyl, 4-isobutoxyphenyl, 4-cyclohexyloxyphenyl, 3-(2-dimethylaminoethoxy)phenyl, 3-(2-piperidin-1-ylethoxy)phenyl, 3-(3-dimethylaminopropoxy)phenyl, or 3-(3-piperidin-1-ylpropoxy)phenyl.

19. A compound as defined in claim 7, wherein $Ar^3$ is 4-chlorophenyl, 3,4-dichlorophenyl, 4-methylphenyl, 4-t-butylphenyl, 3-trifluoromethylphenyl, 4-methoxyphenyl, 3,5-dichlorophenyl, 1-naphthyl, 2-naphthyl, 3-chlorophenyl, 9-phenanthrenyl, 4-carbomethoxylphenyl, 4-methanesulfonylphenyl, 3-methoxyphenyl, benzo[1,3]dioxol-5-yl, or unsubstituted phenyl.

20. A compound as defined in claim 7, wherein $Ar^2$ is 3,4-dibromophenyl, 3-bromo-4-fluorophenyl, or 4-chloro-3-trifluoromethyl.

21. A compound as defined in claim 7, wherein $Ar^2$ is 3,4-dibromophenyl.

22. A pharmaceutical composition comprising:
(a) therapeutically effective amount of an agent selected from the group consisting of compounds of Formula (I):

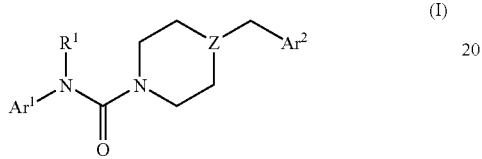

(I)

wherein:
Z is —N— or >CH;
$R^1$ is —H or —$C_{1-4}$alkyl;
$Ar^1$ is 2-thiazolyl, 2-pyridyl, 3-pyridyl, 4-pyridyl, 2-pyrimidinyl, 4-pyrimidinyl, 5-pyrimidinyl, each unsubstituted or substituted at a carbon ring member with one or two $R^a$ moieties;
where each $R^a$ moiety is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are each independently —H or —$C_{1-4}$alkyl; and
$Ar^2$ is:
(a) unsubstituted 1-naphthyl; or phenanthrenyl, pyrenyl, fluorenyl, 2-naphthyl, or N—$R^d$-9H-carbazolyl moieties, wherein $R^d$ is selected from the group consisting of —H, —$C_{1-4}$alkyl, and phenyl, each said moiety unsubstituted or substituted with one, two, or three $R^e$ substituents,
wherein each $R^e$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;
(b) phenyl fused at two adjacent ring carbon atoms to a group selected from the group consisting of —$(CH_2)_{3-5}$— having 0 or 1 double bonds, —$OCH_2CH_2O$—, and —$OCF_2O$— to form a fused ring structure; or phenyl substituted on adjacent ring carbon atoms with —$OCH_2O$— to form 4-benzo[1,3]dioxolyl; each phenyl moiety further unsubstituted or substituted with one, two, or three $R^e$ substituents as previously defined;
(c) $Ar^6$, where $Ar^6$ is a 6-membered monocyclic heteroaryl having carbon as a point of attachment, with one or two nitrogen heteroatoms, unsubstituted or substituted with one, two, or three $R^e$ substituents as previously defined;
(d) a 9- or 10-membered fused bicyclic heteroaryl having one heteroatom selected from the group consisting of N, O, and S, with a carbon atom as point of ring attachment, and optionally having up to four additional carbon ring atoms replaced with nitrogen, said fused bicyclic heteroaryl having not more than five heteroatoms, and unsubstituted or substituted with one, two, or three $R^e$ substituents as previously defined;
(e) phenyl substituted at the 3- or 4-position with $R^g$, and optionally further substituted with one, two, or three substituents $R^h$,
wherein each $R^g$ is independently selected from the group consisting of —$C_{2-8}$alkyl, —$C_{2-8}$alkenyl, —$OC_{3-8}$cycloalkyl, —$OC_{3-8}$heterocycloalkyl, and —O—$C_{2-10}$alkyl optionally substituted with —$NR^iR^j$, wherein $R^i$ and $R^j$ are each independently —H or —$C_{1-8}$alkyl, or $R^i$ and $R^j$ are taken together with the nitrogen ring atom of attachment to form a 5-, 6-, or 7-membered heterocycloalkyl ring optionally having one additional carbon ring atom replaced with O, S, >NH, or >$NC_{1-4}$alkyl; and
each $R^h$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(=O)NR^bR^c$, —$NO_2$, and —CN, wherein $R^b$ and $R^c$ are as previously defined;
(f) phenyl substituted at the 3- or 4-position with -L-$Ar^3$, wherein:
L is a linker selected from the group consisting of —$(CH_2)_{1-3}$—, —CH=CH—, —O—, —$OCH_2$—, —$CH_2O$—, —NH—, >$NC_{1-4}$alkyl, >$S(=O)_{0-2}$, —$OSO_2$—, —C≡C—, —C(=O)—, and a covalent bond; and
$Ar^3$ is a moiety selected from the group consisting of:
(1) phenyl, naphthyl, and phenanthrenyl,
(2) $Ar^{6'}$, where $Ar^{6'}$ is a 6-membered monocyclic heteroaryl having carbon as a point of attachment, having one or two nitrogen heteroatoms,
(3) $Ar^{5'}$, where $Ar^{5'}$ is a 5-membered monocyclic heteroaryl having carbon as a point of attachment, with one heteroatom selected from the group consisting of O, S, >NH, and >$NR^f$, wherein $R^f$ is —$C_{1-8}$alkyl or —$C_{0-3}$phenalkyl, and having zero, one, two, or three additional nitrogen heteroatoms, and
(4) a 9- or 10-membered fused bicyclic heteroaryl, having one heteroatom selected from the group consisting of N, O, and S, with a carbon as point of ring attachment, and optionally having up to four additional carbon ring atoms replaced with nitrogen, said fused bicyclic heteroaryl having not more than five heteroatoms;
where each of the moieties (1) through (4) is optionally di-substituted on adjacent carbons with —$OC_{1-4}$alkyleneO—, —$(CH_2)_{2-3}NH$—, —$(CH_2)_{1-2}NH(CH_2)$—, —$(CH_2)_{2-3}N(C_{1-4}alkyl)$-, or —$(CH_2)_{1-2}N(C_{1-4}alkyl)(CH_2)$— to form a fused ring structure, and is optionally further substituted with one, two, or three substituents $R^k$,
wherein each $R^k$ substituent is independently selected from the group consisting of —$C_{1-4}$alkyl, —$C_{2-4}$alkenyl, —OH, —$OC_{1-4}$alkyl, halo, —$CF_3$, —$OCF_3$, —$SCF_3$, —SH, —$S(O)_{0-2}C_{1-4}$alkyl, —$OSO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(\!\!=\!\!O)NR^bR^c$, —$NO_2$, and —CN, wherein $R^b$ and $R^c$ are as previously defined;

(g) 2-hydroxyphenyl or 2-methoxyphenyl, unsubstituted or substituted with one, two, or three substituents $R^l$, wherein each $R^l$ substituent is independently selected from the group consisting of —$CH_3$, 6-$C_{2-4}$alkyl, 6-$C_{2-4}$alkenyl, —OH, —$OCH_3$, 6-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(\!\!=\!\!O)NR^bR^c$, —$NO_2$, and —CN, wherein $R^b$ and $R^c$ are as previously defined;

(h) 4-halophenyl, unsubstituted or substituted with one, two, or three substituents $R^m$, wherein each $R^m$ substituent is independently selected from the group consisting of —$CH_3$, 2-$C_{2-4}$alkyl, 2-$C_{2-4}$alkenyl, 3-hydroxy, 4-hydroxy, —$OCH_3$, 2-$OC_{2-6}$alkyl, halo, —$CF_3$, —$OCF_3$, —$SCF_3$, —SH, —$SC_{1-4}$alkyl, —$SO_2C_{1-4}$alkyl, —$CO_2C_{1-4}$alkyl, —$CO_2H$, —$COC_{1-4}$alkyl, —$N(R^b)R^c$, —$SO_2NR^bR^c$, —$NR^bSO_2R^c$, —$C(\!\!=\!\!O)NR^bR^c$, —$NO_2$, and —CN, wherein $R^b$ and $R^c$ are as previously defined; or (i) 2-bromophenyl, 3-methylphenyl, 3-methoxyphenyl, 4-methoxyphenyl, or 3,4-dimethoxyphenyl;

and pharmaceutically acceptable salts thereof; and (b) a pharmaceutically acceptable excipient.

23. A pharmaceutical composition according to claim 22, further comprising: an analgesic selected from the group consisting of opioids and non-steroidal anti-inflammatory drugs.

24. A pharmaceutical composition according to claim 22, further comprising: an additional active ingredient selected from the group consisting of aspirin, acetaminophen, opioids, ibuprofen, naproxen, COX-2 inhibitors, gabapentin, pregabalin, and tramadol.

* * * * *